(12) United States Patent
Shore et al.

(10) Patent No.: US 9,682,232 B2
(45) Date of Patent: Jun. 20, 2017

(54) PERSONALIZED AUDITORY-SOMATOSENSORY STIMULATION TO TREAT TINNITUS

(71) Applicant: THE REGENTS OF THE UNIVERSITY OF MICHIGAN, Ann Arbor, MI (US)

(72) Inventors: Susan Shore, Ann Arbor, MI (US); David Martel, Ann Arbor, MI (US); Seth Koehler, Baltimore, MD (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/977,416

(22) Filed: Dec. 21, 2015

(65) Prior Publication Data
US 2016/0106975 A1 Apr. 21, 2016

Related U.S. Application Data

(62) Division of application No. 14/217,090, filed on Mar. 17, 2014, now Pat. No. 9,242,067.

(60) Provisional application No. 61/803,062, filed on Mar. 18, 2013, provisional application No. 61/800,607, filed on Mar. 15, 2013.

(51) Int. Cl.
| | |
|---|---|
| *A61N 1/36* | (2006.01) |
| *A61M 21/02* | (2006.01) |
| *H04R 25/00* | (2006.01) |
| *A61B 5/12* | (2006.01) |
| *A61M 21/00* | (2006.01) |

(52) U.S. Cl.
CPC ............... *A61N 1/36* (2013.01); *A61B 5/128* (2013.01); *A61M 21/02* (2013.01); *A61N 1/36032* (2013.01); *H04R 25/75* (2013.01); *A61M 2021/0027* (2013.01); *A61M 2021/0072* (2013.01); *A61N 1/361* (2013.01)

(58) Field of Classification Search
CPC ..................................................... A61N 1/361
See application file for complete search history.

(56) References Cited

U.S. PATENT DOCUMENTS

| | | | |
|---|---|---|---|
| 6,682,472 | B1 | 1/2004 | Davis |
| 7,520,851 | B2 | 4/2009 | Davis et al. |
| 7,613,519 | B2 | 11/2009 | De Ridder |
| 7,613,520 | B2 | 11/2009 | De Ridder |
| 7,736,297 | B2 | 6/2010 | Davis |
| 7,850,596 | B2 | 12/2010 | Davis et al. |

(Continued)

FOREIGN PATENT DOCUMENTS

| | | |
|---|---|---|
| DE | 10 2011 100065 A1 | 10/2012 |
| WO | WO-2006/047264 A1 | 5/2006 |

(Continued)

OTHER PUBLICATIONS

Abraham et al., Metaplasticity: the plasticity of synaptic plasticity, Trends Neurosci., 19(4):126-30 (1996).

(Continued)

*Primary Examiner* — Paula J Stice
(74) *Attorney, Agent, or Firm* — Marshall, Gerstein & Borun LLP

(57) ABSTRACT

Timed stimulation of both somatosensory system and auditory system is controlled, in such a manner, that an individual's brain activity is altered through spike-timing dependent plasticity, thereby reducing or removing tinnitus.

16 Claims, 31 Drawing Sheets

(56) References Cited

U.S. PATENT DOCUMENTS

| | | |
|---|---|---|
| 7,854,697 B2 | 12/2010 | Davis |
| 8,433,418 B2 | 4/2013 | DeRidder |
| 8,465,411 B2 | 6/2013 | Davis et al. |
| 9,124,979 B2 | 9/2015 | O'Grady et al. |
| 2007/0027504 A1 | 2/2007 | Barrett et al. |
| 2007/0230713 A1 | 10/2007 | Davis |
| 2010/0004705 A1 | 1/2010 | Kilgard et al. |
| 2010/0004717 A1 | 1/2010 | Kilgard et al. |
| 2010/0121411 A1 | 5/2010 | Hochmair et al. |
| 2010/0210896 A1 | 8/2010 | Davis |
| 2011/0040205 A1 | 2/2011 | Parra et al. |
| 2012/0203301 A1 | 8/2012 | Cameron et al. |
| 2013/0253258 A1 | 9/2013 | Davis et al. |
| 2014/0079251 A1 | 3/2014 | O'Grady et al. |
| 2015/0126802 A1 | 5/2015 | Lim et al. |
| 2015/0320966 A1 | 11/2015 | O'Grady et al. |

FOREIGN PATENT DOCUMENTS

| | | |
|---|---|---|
| WO | WO-2012/069429 A1 | 5/2012 |
| WO | WO-2015/028549 A1 | 3/2015 |

OTHER PUBLICATIONS

Abraham, Metaplasticity: tuning synapses and networks for plasticity, Nat. Rev. Neurosci., 9(5):387 (2008).

Adamchic et al., Linking the Tinnitus Questionnaire and the subjective Clinical Global Impression: Which differences are clinically important?, Health and Quality of Life Outcomes, 10:79 (2012).

Adamchic et al., Psychometric evaluation of visual analog scale for the assessment of chronic tinnitus, Am. J. Audiol., 21(2):215-25 (2012).

Aosaki et al., Acetylcholine-dopamine balance hypothesis in the striatum: an update, Geriatr. Gerontol. Int., 10 Suppl 1:S148-57 (2010).

Baizer et al., Understanding tinnitus: the dorsal cochlear nucleus, organization and plasticity, Brain Res., 1485:40-53 (2012).

Basura et al., Multi-sensory integration in brainstem and auditory cortex, Brain Res., 1485:95-107 (2012).

Bauer et al., Tinnitus and inferior colliculus activity in chinchillas related to three distinct patterns of cochlear trauma, J. Neurosci. Res., 86(11):2564-78 (2008).

Bertet et al., Design and evaluation of tinnitus synthesis methods: from spectral to spatial matching, Am. J. Otolaryngol., 34(2):121-32 (2013).

Bezerra Rocha et al., Myofascial trigger point:a possible way of modulating tinnitus, Audiol. Neurootol., 13(3):153-60 (2008).

Biesinger et al., The role of the cervical spine and the craniomandibular system in the pathogenesis of tinnitus. Somatosensory tinnitus, HNO, 56(7):673-7 (2008).

Brozoski et al., Bilateral dorsal cochlear nucleus lesions prevent acoustic-trauma induced tinnitus in an animal model, J. Assoc. Res. Otolaryngol., 13(1):55-66 (2012).

Brozoski et al., Elevated fusiform cell activity in the dorsal cochlear nucleus of chinchillas with psychophysical evidence of tinnitus, J. Neurosci., 22(6):2383-90 (2002).

Coelho et al., Reduction of tinnitus severity by the centrally acting muscle relaxant cyclobenzaprine: an open-label pilot study, Audiol. Neurootol., 17(3):179-88 (2012).

D'Elia, Sustained, high dose treatment with sodium salicylate disrupts the rat auditory brainstem response, Association for Research in Otolaryngology Conference, Poster 250 (2010).

Dahmen et al., Stimulus-timing-dependent plasticity of cortical frequency representation, J. Neurosci., 28(5):13629-39 (2008).

Davis et al., Effects of somatosensory and parallel-fiber stimulation on neurons in dorsal cochlear nucleus, J. Neurophysiol., 76(5):3012-24 (1996).

De Azevedo et al., A critical analysis of tinnitus measuring methods, Braz. J. Otorhinolaryngol., 73(3):418-23 (2007).

De Kleine et al., Somatosensory modulation of tinnitus, an FMRI study, Association for Research in Otolaryngology Conference, Poster 251 (2010).

De Ridder et al., Burst stimulation of the auditory cortex: a new form of neurostimulation for noise-like tinnitus suppression, J. Neurosurg., 112(6):1289-94 (2010).

De Ridder et al., Do tonic and burst TMS modulate the lemniscal and extralemniscal system differentially?, Int. J. Med. Sci., 4(5):242-6 (2007).

De Ridder et al., Dorsolateral prefrontal cortex transcranial magnetic stimulation and electrode implant for intractable tinnitus, World Neurosurg., 77(5-6):778-84 (2012).

De Ridder et al., EEG Driven tDCS Versus Bifrontal tDCS for Tinnitus, Front Psychiatry, 3:84 (2012).

De Ridder et al., Frontal cortex TMS for tinnitus, Brain Stimul., 6(3):355-61 (2013).

De Ridder et al., Phantom percepts: tinnitus and pain as persisting aversive memory networks, Proc. Natl. Acad. Sci. USA, 108(20):8075-80 (2011).

De Ridder et al., The Bayesian brain: Phantom percepts resolve sensory uncertainty, Neurosci. Biobehav. Rev., Apr. 11, 2012.

De Ridder et al., The distressed brain: a group blind source separation analysis on tinnitus, PLoS One, 6(10):e24273 (2011).

De Ridder et al., Theta, alpha and beta burst transcranial magnetic stimulation: brain modulation in tinnitus, Int. J. Med. Sci., 4(5):237-41 (2007).

De Ridder et al., Theta-gamma dysrhythmia and auditory phantom perception, J. Neurosurg., 114(4):912-21 (2011).

De Ridder et al., Transcranial magnetic stimulation and extradural electrodes implanted on secondary auditory cortex for tinnitus suppression, J. Neurosurg., 114(4):903-11 (2011).

De Ridder et al., Visualizing out-of-body experience in the brain, N. Engl. J. Med., 357(18):1829-33 (2007).

De Ridder, Should rTMS for tinnitus be performed left-sided, ipsilaterally or contralaterally, and is it a treatment or merely investigational?, Eur. J. Neurol., 17(7):891-2 (2010).

Dehmel et al., Cross-modal interactions of auditory and somatic inputs in the brainstem and midbrain and their imbalance in tinnitus and deafness, Am. J. Audiol., 17(2):S193-209 (2008).

Dehmel et al., Exploring multisensory integration using a three-dimensional silicon microelectrode array for simultaneous ventral and dorsal cochlear nucleus, Association for Research in Otolaryngology Conference, Poster 229 (2010).

Dehmel et al., Gap induced reduction of the acoustic startle response as a behavioural test for noise induced tinnitus in guinea pigs, Association for Research in Otolaryngology Conference, Poster 865 (2010).

Dehmel et al., Gap prepulse inhibition and auditory brainstem-evoked potentials as objective measures for tinnitus in guinea pigs, Front Syst. Neurosci., 6:42 (2012).

Dehmel et al., Noise overexposure alters long-term somatosensory-auditory processing in the dorsal cochlear nucleus—possible basis for tinnitus-related hyperactivity?, J. Neurosci., 32(5):1660-71 (2012).

Dohrmann et al., Tuning the tinnitus percept by modification of synchronous brain activity, Restor. Neurol. Neurosci., 25(3-4):371-8 (2007).

Doiron et al., Combined LTP and LTD of modulatory inputs controls neuronal processing of primary sensory inputs, J. Neurosci., 31(29):10579-92 (2011).

Elgoyhen et al., Pharmacological approaches to the treatment of tinnitus, Drug Discov. Today, 15(7-8):300-5 (2010).

Elgoyhen et al., The nicotinic receptor of cochlear hair cells: a possible pharmacotherapeutic target?, Biochem. Pharmacol., 78(7):712-9 (2009).

Elgoyhen et al., Tinnitus: network pathophysiology-network pharmacology, Front Syst. Neurosci., 6:1 (2012).

Engineer et al., Directing neural plasticity to understand and treat tinnitus, Hear Res., 295:58-66 (2013).

Figueiredo et al., Correlation analysis of the visual-analogue scale and the Tinnitus Handicap Inventory in tinnitus patients, Braz. J. Otorhinolaryngol., 75(1):76-9 (2009).

Figueiredo et al., Incidence of tinnitus in mp3 player users, Braz. J. Otorhinolaryngol., 77(3):293-8 (2011).

(56) References Cited

OTHER PUBLICATIONS

Fryatt et al., Ototrauma induces sodium channel plasticity in auditory afferent neurons, Mol. Cell Neurosci., 48(1):51-61 (2011).
Gambino et al., Spike-timing-dependent potentiation of sensory surround in the somatosensory cortex is facilitated by deprivation-mediated disinhibition, Neuron., 75(3):490-502 (2012).
Goble et al., Acute high-intensity sound exposure alters responses of place cells in hippocampus, Hear. Res., 253(1-2):52-9 (2009).
Gu et al., Auditory evoked potentials in people with tinnitus: a relationship to sound-level tolerance? Poster 252, Association for Research in Otolaryngology Conference (2010).
Gu et al., Brainstem Auditory Evoked Potentials Suggest a Role for the Ventral Cochlear Nucleus in Tinnitus, J. Assoc. Res. Otolaryngology, 13(6):819-33 (2012).
Gu et al., Tinnitus, diminished sound-level tolerance, and elevated auditory activity in humans with clinically normal hearing sensitivity, J. Neurophysiol., 104(6):3361-70 (2010).
Guo et al., Dark exposure extends the integration window for spike-timing-dependent plasticity, J. Neurosci., 32(43):15027-35 (2012).
Haenggeli et al., Projections from the spinal trigeminal nucleus to the cochlear nucleus in the rat, J. Comp. Neurol., 484(2):191-205 (2005).
Hall et al., Treatment options for subjective tinnitus: self reports from a sample of general practitioners and ENT physicians within Europe and the USA, BMC Health Serv. Res., 11:302 (2011).
Hartmann et al., "Investigating the neural correlates of percepts using magnetoencephalography and magnetic source imaging", pp. 51-64, in: Kraft et al. (eds.), Neural Correlates of Thinking, Springer-Verlag Berlin Heidelberg (2009).
Herraiz et al., Tinnitus retraining therapy: prognosis factors, Am. J. Otolaryngol., 28(4):225-9 (2007).
Hiseni et al., A nano power CMOS tinnitus detector for a fully implantable closed-loop neurodevice, IEEE Biomedical Circuits and Systems Conference, BioCAS 2011 (2012).
International Search Report and Written Opinion, corresponding International Application No. PCT/US2014/030765, mailed Jul. 21, 2014.
Jin et al., Effects of intense tone exposure on choline acetyltransferase activity in the hamster cochlear nucleus, Hear Res., 216-217:168-75 (2006).
Joos et al., Disentangling depression and distress networks in the tinnitus brain, PLoS One, 7(7):e40544 (2012).
Kahlbrock et al., Transient reduction of tinnitus intensity is marked by concomitant reductions of delta band power, BMC Biol., 6:4 (2008).
Kaltenbach et al., Activity in the dorsal cochlear nucleus of hamsters previously tested for tinnitus following intense tone exposure, Neurosci. Lett., 355(1-2):121-5 (2004).
Kaltenbach et al., Increases in Spontaneous Activity in the Dorsal Cochlear Nucleus Following Exposure to High Intensity Sound: A Possible Neural Correlate of Tinnitus, Aud. Neurosci., 3(1):57-78 (1996).
Kanold et al., Proprioceptive information from the pinna provides somatosensory input to cat dorsal cochlear nucleus, J. Neurosci., 21(19):7848-58 (2001).
Kanold et al., Somatosensory context alters auditory responses in the cochlear nucleus, J. Neurophysiol., 105(3):1063-70 (2011).
Kapoula et al., Eye movement abnormalities in somatic tinnitus: fixation, smooth pursuit and optokinetic nystagmus, Auris Nasus Larynx, 37(3):314-21 (2010).
Kapoula et al., Medio-lateral postural instability in subjects with tinnitus, Front Neurol., 2:35 (2011).
Khedr et al., One-year follow up of patients with chronic tinnitus treated with left temporoparietal rTMS, Eur. J. Neurol., 16(3):404-8 (2009).
Kleinjung et al., Curing tinnitus with a Cochlear Implant in a patient with unilateral sudden deafness: a case report, Cases J., 2:7462 (2009).
Kleinjung et al., Strategies for enhancement of transcranial magnetic stimulation effects in tinnitus patients, Int. Tinnitus J., 15(2):154-60 (2009).
Kleinjung et al., Transcranial magnetic stimulation: a new diagnostic and therapeutic tool for tinnitus patients, Int. Tinnitus J., 14(2):112-8 (2008).
Knudson et al., Auditory peripheral dysfunction in tinnitus subjects with clinically normal audiograms, Poster 667, Association for Research in Otolaryngology (2010).
Koehler et al., Somatosensory inputs modify auditory spike timing in dorsal cochlear nucleus principal cells, Eur. J. Neurosci., 33(3):409-20 (2011).
Koehler et al., Stimulus-timing dependent multisensory plasticity in the guinea pig dorsal cochlear nucleus, PLoS One, 8(3):e59828 (2013).
Komiya et al., Spontaneous firing activity of cortical neurons in adult cats with reorganized tonotopic map following pure-tone trauma, Acta. Otolaryngol., 120(6):750-6 (2000).
Kraus et al., Noise trauma impairs neurogenesis in the rat hippocampus, Neuroscience, 167(4):1216-26 (2010).
Kreuzer et al., Can Temporal Repetitive Transcranial Magnetic Stimulation be Enhanced by Targeting Affective Components of Tinnitus with Frontal rTMS? A Randomized Controlled Pilot Trial, Front Syst. Neurosci., 5:88 (2011).
Kreuzer et al., Mindfulness-and body-psychotherapy-based group treatment of chronic tinnitus: a randomized controlled pilot study, BMC Complement Altern. Med., 12:235 (2012).
Kreuzer et al., Transcutaneous vagus nerve stimulation: retrospective assessment of cardiac safety in a pilot study, Front Psychiatry, 3:70 (2012).
Kreuzer et al., Trauma-associated tinnitus: audiological, demographic and clinical characteristics, PLoS One, 7(9):e45599 (2012).
Kujawa et al., Adding insult to injury: cochlear nerve degeneration after "temporary" noise-induced hearing loss, J. Neurosci., 29(45):14077-85 (2009).
Landgrebe et al., Association of tinnitus and electromagnetic hypersensitivity: hints for a shared pathophysiology?, PLoS One, 4(3):e5026 (2006).
Landgrebe et al., Design of a placebo-controlled, randomized study of the efficacy of repetitive transcranial magnetic stimulation for the treatment of chronic tinnitus, BMC Psychiatry, 8:23 (2008).
Landgrebe et al., Neuronal correlates of symptom formation in functional somatic syndromes: a fMRI study, Neuroimage, 41(4):1336-44 (2008).
Landgrebe et al., Structural brain changes in tinnitus: grey matter decrease in auditory and non-auditory brain areas, Neuroimage, 46(1):213-8 (2009).
Langguth et al., Neuroimaging and neuromodulation: complementary approaches for identifying the neuronal correlates of tinnitus, Front Syst. Neurosci., 6:15 (2012).
Langguth et al., Transcranial magnetic stimulation for the treatment of tinnitus: effects on cortical excitability, BMC Neurosci., 8:45 (2007).
Leaver et al., Dysregulation of limbic and auditory networks in tinnitus, Neuron., 69(1):33-43 (2011).
Lee et al., Metaplasticity at single glutamatergic synapses, Neuron, 66(6):859-70 (2010).
Lehner et al., Multisite rTMS for the treatment of chronic tinnitus: stimulation of the cortical tinnitus network—a pilot study, Brain Topogr., 26(3):501-10 (2013).
Lehner et al., Predictors for rTMS response in chronic tinnitus, Front Syst. Neurosci., 6:11 (2012).
Levine et al., Somatosensory pulsatile tinnitus syndrome: somatic testing identifies a pulsatile tinnitus subtype that implicates the somatosensory system, Trends Amplif., 12(3):242-53 (2008).
Levine et al., Typewriter tinnitus: a carbamazepine-responsive syndrome related to auditory nerve vascular compression, ORL J. Otorhinolaryngol. Relat. Spec., 68(1):43-6, discussion 46-7 (2006).
Levine, Somatic (craniocervical) tinnitus and the dorsal cochlear nucleus hypothesis, Am. J. Otolaryngol., 20(6):351-62 (1999).
Lindblad et al., Noise-induced tinnitus: a comparison between four clinical groups without apparent hearing loss, Noise Health, 13(55):423-31 (2011).

(56) References Cited

OTHER PUBLICATIONS

Lobarinas et al., Baclofen and the role of GABA inhibition on salicylate and noise induced tinnitus, Poster 866, Association for Research in Otolaryngology (2010).
Lobarinas et al., Human brain imaging of tinnitus and animal models, Semin. Hear., 29(4):333-49 (2008).
Lobarinas et al., The gap-startle paradigm for tinnitus screening in animal models: limitations and optimization, Hear Res., 295:150-60 (2013).
Londero et al., Auditory and visual 3D virtual reality therapy for chronic subjective tinnitus: theoretical framework, Virtual Reality, 14:143-51 (2010).
Lopez-Gonzalez et al., Sudden deafness caused by lifestyle stress. Pathophysiological mechanisms and new therapeutic perspectives, Open Otorhinolaryngol. J., 3:1-4(2009).
Lorenz et al., Loss of alpha power is related to increased gamma synchronization—A marker of reduced inhibition in tinnitus?, Neurosci. Lett., 453(3):225-8 (2009).
Ma et al., Dorsal cochlear nucleus response properties following acoustic trauma: response maps and spontaneous activity, Hear Res., 216-217:176-88 (2006).
Mao et al., Blast-induced tinnitus and hearing loss in rats: behavioral and imaging assays, J. Neurotrauma, 29(2):430-44 (2012).
Masquelier et al., Spike timing dependent plasticity finds the start of repeating patterns in continuous spike trains, PLoS One, 3(1):e1377 (2008).
Meikle et al., The tinnitus functional index: development of a new clinical measure for chronic intrusive tinnitus, Ear Hear, 2011.
Melcher, A model for tinnitus generation based in the ventral, not dorsal, cochlear nucleus, Association for Research in Otolaryngology Conference, Poster 242 (2010).
Meredith et al., STDP and Mental Retardation: Dysregulation of Dendritic Excitability in Fragile X Syndrome, Front Synaptic Neurosci., 2:10 (2010).
Muehlmeier et al., Safety of intratympanic injection of AM-101 in patients with acute inner ear tinnitus, Audiol. Neurootol., 16(6):388-97 (2011).
Muhlnickel et al., Reorganization of auditory cortex in tinnitus, Proc. Natl. Acad. Sci. USA, 95(17):10340-3 (1998).
Muller et al., Lateralized auditory cortical alpha band activity and interregional connectivity pattern reflect anticipation of target sounds, Cereb. Cortex, 22(7)1604-13 (2012).
New evidence touch-sensing nerve cells may fuel ringing in the ears, University of Michigan Health System (Feb. 1, 2012).
Norena et al., Tinnitus-related neural activity: theories of generation, propagation, and centralization, Hear. Res., 295:161-71 (2013).
Norena, An integrative model of tinnitus based on a central gain controlling neural sensitivity, Neurosci. Biobehay. Rev., 35(5):1089-109 (2011).
Okamoto et al., Frequency-specific modulation of population-level frequency tuning in human auditory cortex, BMC Neurosci., 10:1 (2009).
Okamoto et al., Listening to tailor-made notched music reduces tinnitus loudness and tinnitus-related auditory cortex activity, Proc. Natl. Acad. Sci. USA, 107(3):1207-10 (2010).
Panford-Walsh et al., Midazolam reverses salicylate-induced changes in brain-derived neurotrophic factor and arg3.1 expression: implications for tinnitus perception and auditory plasticity, Mol. Pharmacol., 74(3):595-604 (2008).
Pantev et al., Tinnitus: the dark side of the auditory cortex plasticity, Ann. NY Acad. Sci., 1252:253-8 (2012).
Parra et al., Illusory percepts from auditory adaptation, J. Acoust. Soc Am., 121:1632 (2007).
Paul et al., Metabolic imaging of rat brain during pharmacologically-induced tinnitus, Neuroimage, 44(2):312-8 (2009).
Pawlak et al., Timing is not Everything: Neuromodulation Opens the STDP Gate, Front Synaptic Neurosci., 2:146 (2010).
Pilati et al., Mechanisms contributing to central excitability changes during hearing loss, Proc. Natl. Acad. Sci. USA, 109(21):8292-7 (2012).
Pinchoff et al., Modulation of tinnitus by voluntary jaw movements, Am. J. Otol., 19(6):785-9 (1998).
Pinto et al., The impact of gender, age and hearing loss on tinnitus severity, Braz. J. Otorhinolaryngol., 76(1):18-24 (2010).
Pridmore et al., Transcranial magnetic stimulation: potential treatment for tinnitus?, Psychiatry Clin. Neurosci., 60(2):133-8 (2006).
Ralli et al., Comparison of salicylate- and quinine-induced tinnitus in rats: development, time course, and evaluation of audiologic correlates, Otol. Neurotol., 31(5):823-31 (2010).
Rauschecker et al., Tuning out the noise: limbic-auditory interactions in tinnitus, Neuron., 66(6):819-26 (2010).
Roberts et al., A randomized, controlled study comparing the effects of vestipitant or vestipitant and paroxetine combination in subjects with tinnitus, Otol. Neurotol., 32(5):721-7 (2011).
Roberts et al., Design principles of sensory processing in cerebellum-like structures. Early stage processing of electrosensory and auditory objects, Biol. Cybern., 98(6):491-507 (2008).
Roberts et al., Residual inhibition functions overlap tinnitus spectra and the region of auditory threshold shift, J. Assoc. Res. Otolaryngol., 9(4):417-35 (2008).
Roberts et al., Ringing ears: the neuroscience of tinnitus, J. Neurosci., 30(45):14972-9 (2010).
Ruel et al., Salicylate enables cochlear arachidonic-acid-sensitive NMDA receptor responses, J. Neurosci., 28(29):7313-23 (2008).
Sanches et al., Influence of cochlear function on auditory temporal resolution in tinnitus patients, Audiol. Neurootol., 15(5):273-81 (2010).
Sanchez et al., Somatic modulation of tinnitus: test reliability and results after repetitive muscle contraction training, Ann. Otol. Rhinol. Laryngol., 116(1):30-5 (2007).
Sand et al., An Examination of KCNE1 Mutations and Common Variants in Chronic Tinnitus, Genes (Basel), 1(1):23-37 (2010).
Sand et al., GDNF and BDNF gene interplay in chronic tinnitus, Int. J. Mol. Epidemiol. Genet., 3(3):245-51 (2012).
Sand et al., Resequencing of the auxiliary GABA(B) receptor subunit gene KCTD12 in chronic tinnitus, Front Syst. Neurosci., 6:41 (2012).
Saul et al., Math5 expression and function in the central auditory system, Mol. Cell Neurosci., 37(1):153-69 (2008).
Sawtell et al., Adaptive processing in electrosensory systems: links to cerebellar plasticity and learning, J. Physiol. Paris, 102(4-6):223-32 (2008).
Sawtell, Multimodal integration in granule cells as a basis for associative plasticity and sensory prediction in a cerebellum-like circuit, Neuron., 66(4):573-84 (2010).
Schecklmann et al., Cluster analysis for identifying sub-types of tinnitus: a positron emission tomography and voxel-based morphometry study, Brain Res., 1485:3-9 (2012).
Schecklmann et al., Neural correlates of tinnitus duration and distress: a positron emission tomography study, Hum. Brain Mapp., 34(1):233-40 (2013).
Schecklmann et al., Relationship between Audiometric slope and tinnitus pitch in tinnitus patients: insights into the mechanisms of tinnitus generation, PLoS One, 7(4):e34878 (2012).
Schlee et al., "Unraveling the tinnitus distress network using single trial auditory steady-state responses", pp. 73-76 in: Cheyne et al. (eds.), International Congress Series, vol. 1300, New Frontiers in Biomagnetism, Proceedings of the 15th International Conference on Biomagnetism, Vancouver, Canada (2007).
Schlee et al., Abnormal resting-state cortical coupling in chronic tinnitus, BMC Neurosci., 10:11 (2009).
Schlee et al., Does tinnitus distress depend on age of onset?, PLoS One, 6(11):e27379 (2011).
Schlee et al., Mapping cortical hubs in tinnitus, BMC Biol., 7:80 (2009).
Schlee et al., Using auditory steady state responses to outline the functional connectivity in the tinnitus brain, PLoS One, 3(11):e3720 (2008).

(56) References Cited

OTHER PUBLICATIONS

Schonfeldt-Lecuona et al., Effect of 1 Hz repetitive transcranial magnetic stimulation over the auditory cortex on audiometry and otoacustic emissions, Brain Topogr., 25(3):241-7 (2012).
Searchfield et al., An adaptation level theory of tinnitus audibility, Front Syst. Neurosci., 6:46 (2012).
Shahin et al., Development of auditory phase-locked activity for music sounds, J. Neurophysiol., 103(1):218-29 (2010).
Shahin et al., Music training leads to the development of timbre-specific gamma band activity, Neuroimage, 41(1):113-22 (2008).
Shore et al, "Noise Overexposure Alters Long-Term Somatosensory-Auditory Processing in the Dorsal Cochlear Nucleus-Possible Basis for Tinnitus-Related Hyperactivity?", The Journal of Neuroscience, 35(5):1600-1671 (2012).
Shore et al., Dorsal cochlear nucleus responses to somatosensory stimulation are enhanced after noise-induced hearing loss, Eur. J. Neurosci., 27(1):155-68 (2008).
Shore, Multisensory integration in the dorsal cochlear nucleus: unit responses to acoustic and trigeminal ganglion stimulation, Eur. J. Neurosci., 21(12):3334-48 (2005).
Singer et al., Salicylate alters the expression of calcium response transcription factor 1 in the cochlea: implications for brain-derived neurotrophic factor transcriptional regulation, Mol. Pharmacol., 73(4):1085-91 (2008).
Smith et al., Co-activation of the somatosensory and auditory pathways to induce central auditory plasticity as a new approach for treating tinnitus, University of Minnesota Sonic Lab, Association for Research in Otolaryngology Poster (2013).
Smits et al., Lateralization of functional magnetic resonance imaging (fMRI) activation in the auditory pathway of patients with lateralized tinnitus, Neuroradiology, 49(8):669-79 (2007).
Song et al., Mapping tinnitus-related brain activation: an activation-likelihood estimation metaanalysis of PET studies, J. Nucl. Med., 53(10):1550-7 (2012).
Song et al., Transcranial direct current stimulation in tinnitus patients: a systemic review and meta-analysis, ScientificWorldJournal, 2012:427941 (2012).
Stabler et al., Temporal and mean rate discharge patterns of single units in the dorsal cochlear nucleus of the anesthetized guinea pig, J. Neurophyiol., 76(3):1667-88 (1996).
Stolzberg et al., Intracortical circuits amplify sound-evoked activity in primary auditory cortex following systemic injection of salicylate in the rat, J. Neurophysiol., 108(1):200-14 (2012).
Stolzberg et al., Salicylate toxicity model of tinnitus, Front Syst. Neurosci., 6:28 (2012).
Stolzberg et al., Salicylate-induced peripheral auditory changes and tonotopic reorganization of auditory cortex, Neuroscience, 180:157-64 (2011).
Stolzberg et al., Salicylate-induced tinnitus: alterations in neuronal activity in the inferior colliculus of tranquilized mice, Association for Research in Otolaryngology Conference, Poster 784 (2010).
Su et al., Altered neuronal intrinsic properties and reduced synaptic transmission of the rat's medial geniculate body in salicylate-induced tinnitus, PLoS One, 7(10):e46969 (2012).
Sun et al., Salicylate increases the gain of the central auditory system, Neuroscience, 159(1):325-34 (2009).
Tan et al., Tinnitus behavior and hearing function correlate with the reciprocal expression patterns of BDNF and Arg3.1/arc in auditory neurons following acoustic trauma, Neuroscience, 145(2):715-26 (2007).
Taranda et al., A point mutation in the hair cell nicotinic cholinergic receptor prolongs cochlear inhibition and enhances noise protection, PLoS Biol., 7(1):e18 (2009).
Trainor et al., Understanding the benefits of musical training: effects on oscillatory brain activity, Ann. NY Acad. Sci., 1169:133-42 (2009).
Turner et al., Gap detection deficits in rats with tinnitus: a potential novel screening tool, Behav. Neurosci., 120(1):188-95 (2006).
Turner et al., Time course of tinnitus development following noise exposure in mice, J. Neurosci. Res., 90(7):1480-8 (2012).
Tzounopoulos et al., Cell-specific, spike timing-dependent plasticities in the dorsal cochlear nucleus, Nat. Neurosci., 7(7):719-25 (2004).
Tzounopoulos et al., Coactivation of pre- and postsynaptic signaling mechanisms determines cell-specific spike-timing-dependent plasticity, Neuron, 54(2):291-301 (2007).
Vanneste et al., Bilateral dorsolateral prefrontal cortex modulation for tinnitus by transcranial direct current stimulation: a preliminary clinical study, Exp. Brain Res., 202(4):779-85 (2010).
Vanneste et al., Parietal double-cone coil stimulation in tinnitus, Exp. Brain Res., 221(3):337-43 (2012).
Vanneste et al., Prefrontal cortex based sex differences in tinnitus perception: same tinnitus intensity, same tinnitus distress, different mood, PLoS One, 7(2):e31182 (2012).
Vanneste et al., The auditory and non-auditory brain areas involved in tinnitus. An emergent property of multiple parallel overlapping subnetworks, Front Syst. Neurosci., 6:31 (2012).
Vanneste et al., The differences in brain activity between narrow band noise and pure tone tinnitus, PLoS One, 5(10):e13618 (2010).
Vanneste et al., The involvement of the left ventrolateral prefrontal cortex in tinnitus: a TMS study, Exp. Brain Res., 221(3):345-50 (2012).
Vanneste et al., Transcutaneous electrical nerve stimulation (TENS) of upper cervical nerve (C2) for the treatment of somatic tinnitus, Exp. Brain Res., 204(2):283-7 (2010).
Vermeire et al., Phase-shift tinnitus treatment: an open prospective clinical trial, B-ENT, 3 Suppl 7:65-9 (2007).
Vielsmeier et al., Temporomandibular joint disorder complaints in tinnitus: further hints for a putative tinnitus subtype, PLoS One, 7(6):e38887 (2012).
Vielsmeier et al., Tinnitus with temporomandibular joint disorders: a specific entity of tinnitus patients?, Otolaryngol. Head Neck Surg., 145(5):748-52 (2011).
Vollmann et al., When the ringing in the ears gets unbearable: Illness representations, self-instructions and adjustment to tinnitus, J. Psychosom. Res., 73(2):108-11 (2012).
Wang et al., Plasticity at glycinergic synapses in dorsal cochlear nucleus of rats with behavioral evidence of tinnitus, Neuroscience, 164(2):747-59 (2009).
Wei et al., Effects of sodium salicylate on spontaneous and evoked spike rate in the dorsal cochlear nucleus, Hear. Res., 267(1-2):54-60 (2010).
Wei et al., Salicylate-induced degeneration of cochlea spiral ganglion neurons-apoptosis signaling, Neuroscience, 168(1):288-99 (2010).
Weisz et al., Alpha rhythms in audition: cognitive and clinical perspectives, Front Psychol., 2:73 (2011).
Weisz et al., Formerly known as inhibitory: effects of 1-Hz rTMS on auditory cortex are state-dependent, Eur. J. Neurosci., 36(1):2077-87 (2012).
Weisz et al., The neural code of auditory phantom perception, J. Neurosci., 27(6):1479-84 (2007).
Wilson et al., Listening to filtered music as a treatment option for tinnitus: a review, Music Percept., 27(4):327-30 (2010).
Young et al., Somatosensory effects on neurons in dorsal cochlear nucleus, J. Neurophysiol., 73(2):743-65 (1995).
Zeman et al., Tinnitus assessment by means of standardized self-report questionnaires: psychometric properties of the Tinnitus Questionnaire (TQ), the Tinnitus Handicap Inventory (THI), and their short versions in an international and multi-lingual sample, Health Qual. Life Outcomes, 10:128 (2012).
Zeng et al., Cochlear damage changes the distribution of vesicular glutamate transporters associated with auditory and nonauditory inputs to the cochlear nucleus, J. Neurosci., 29(13):4210-7 (2009).
Zeng et al., Cuneate and spinal trigeminal nucleus projections to the cochlear nucleus are differentially associated with vesicular glutamate transporter-2, Neuroscience, 176:142-51 (2011).
Zeng et al., Somatosensory projections to cochlear nucleus are upregulated after unilateral deafness, J. Neurosci., 32(45):15791-801 (2012).
Zhang et al., Auditory cortex electrical stimulation suppresses tinnitus in rats, J. Assoc. Res. Otolaryngol., 12(2):185-201 (2011).

(56) References Cited

OTHER PUBLICATIONS

Zhao et al., Physiological activation of cholinergic inputs controls associative synaptic plasticity via modulation of endocannabinoid signaling, J. Neurosci., 31(9):3158-68 (2011).

Zhou et al., Impaired cochlear function correlates with the presence of tinnitus and its estimated spectral profile, Hear. Res., 277(1-2):107-16 (2011).

Zhou et al., Projections from the trigeminal nuclear complex to the cochlear nuclei: a retrograde and anterograde tracing study in the guinea pig, J. Neurosci. Res., 78(6):901-7 (2004).

Zhou et al., Sensitization to masked tones following notched-noise correlates with estimates of cochlear function using distortion product otoacoustic emissions, J. Acoust. Soc. Am., 127(2):970-6 (2010).

Zhou et al., Vessicular glutamate transporters 1 and 2 are differentially associated with auditory nerve and spinal trigeminal inputs to the cochlear nucleus, J. Comp. Neurol., 500(4):777-87 (2007).

Extended European search report from Application No. 14765204.4 dated Oct. 11, 2016.

Bimodal intervals (ms)

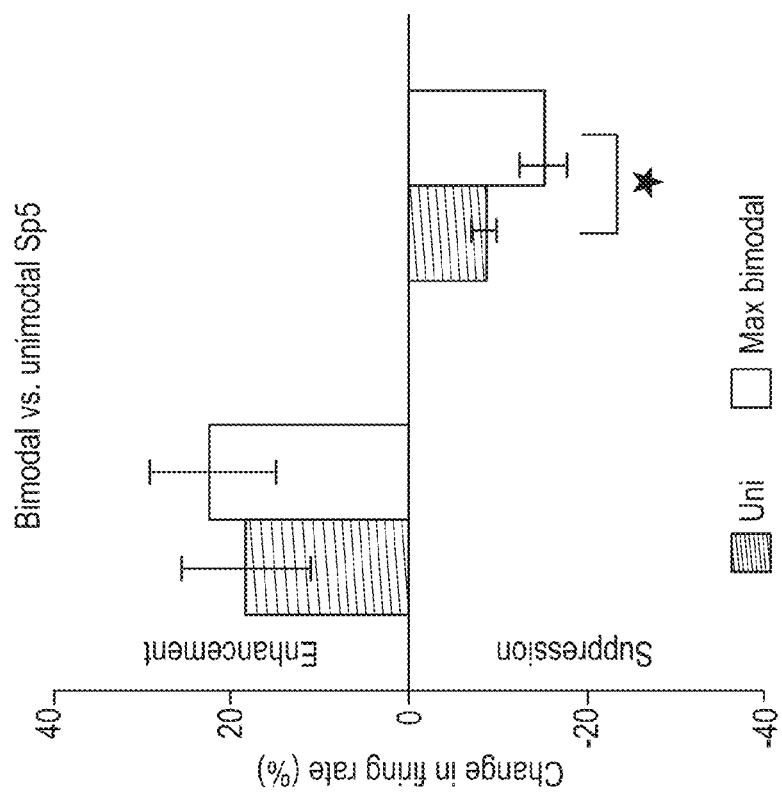
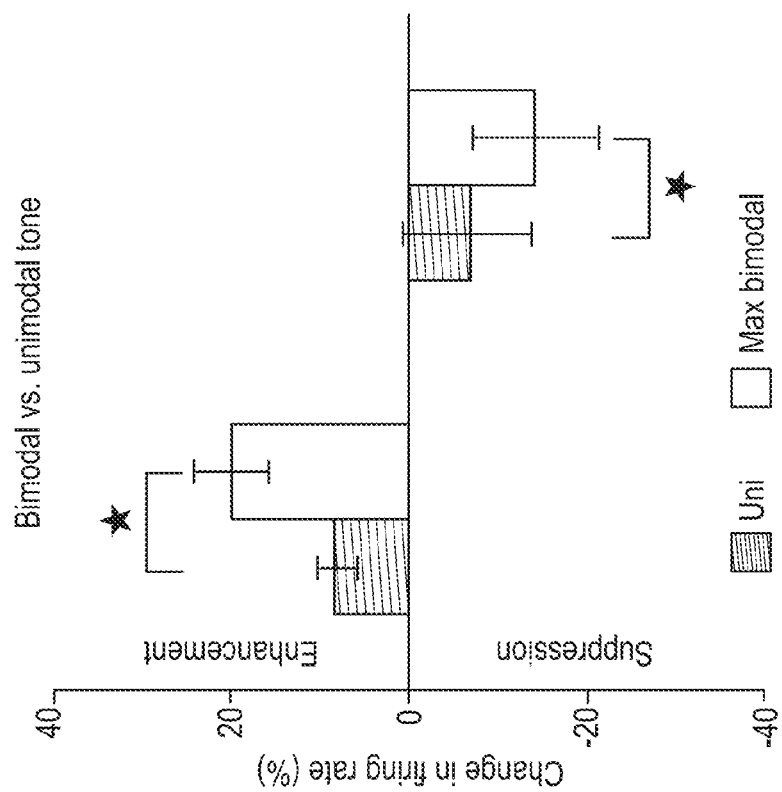

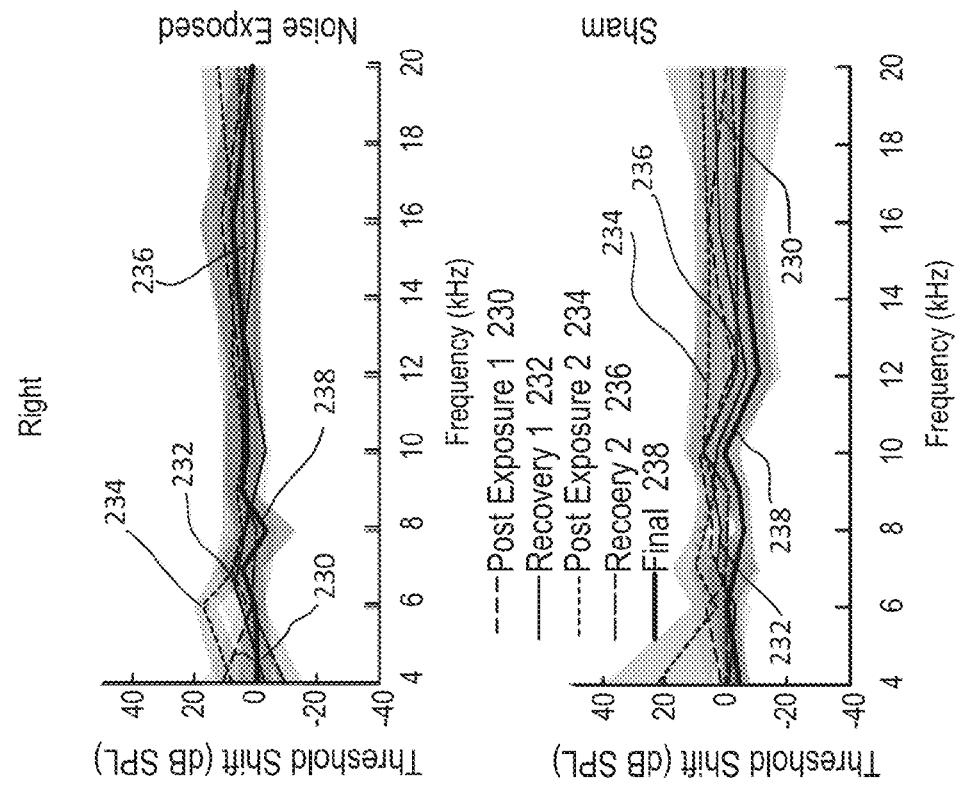
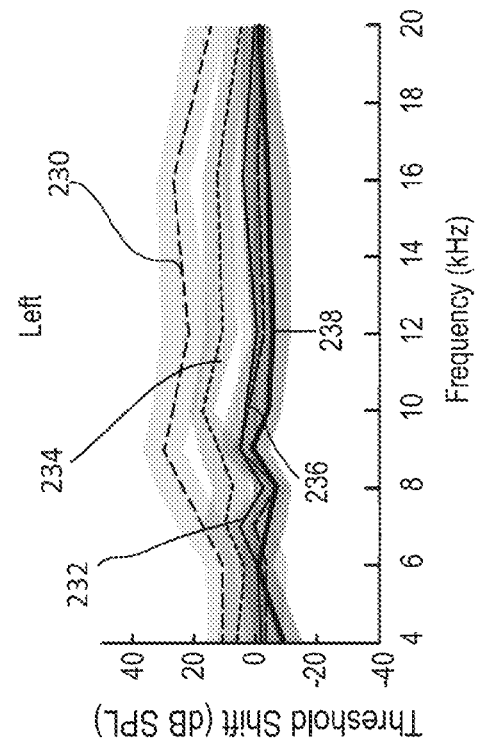
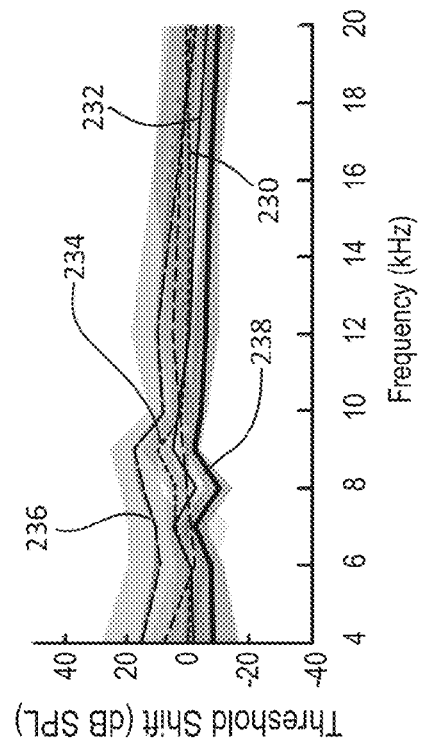
FIG. 11A  FIG. 11B  FIG. 11C  FIG. 11D

PERSONALIZED AUDITORY-SOMATOSENSORY STIMULATION TO TREAT TINNITUS

CROSS-REFERENCE TO RELATED APPLICATION

This application is a divisional of U.S. application Ser. No. 14/217,090, filed Mar. 17, 2014, entitled "Personalized Auditory-Somatosensory Stimulation to Treat Tinnitus," now U.S. Pat. No. 9,242,067, issued Jan. 26, 2016, which claims the benefit of U.S. Application No. 61/800,607, filed Mar. 15, 2013, entitled "Personalized Auditory-Somatosensory Stimulation to Treat Tinnitus" and U.S. Application No. 61/803,062, filed Mar. 18, 2013, entitled "Personalized Auditory-Somatosensory Stimulation to Treat Tinnitus," both of which are hereby incorporated by reference in their entirety.

GOVERNMENT SPONSORSHIP CLAUSE

This invention was made with government support under DC004825, DC005188 and DC000011 awarded by the National Institutes of Health. The government has certain rights in the invention.

BACKGROUND OF THE DISCLOSURE

Field of Technology

The present disclosure relates generally to treatment and tinnitus and, more particularly, to the use of a bimodal stimulation, with stimulation of the auditory and somatosensory systems, to treat tinnitus.

Background

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Tinnitus is the phantom perception of sound experienced in a subject's ear or head, when no actual sound is present. Tinnitus, considered subjective phenomenon, can vary in degrees of severity. One commonly referred to expression of tinnitus is "ringing in the ears"; but there are many different forms of tinnitus.

Tinnitus has been linked to somatosensory innervation of the auditory system. For example, both tinnitus patients and normal subjects report that somatosensory stimuli such as pressure on the face or movement of the jaw or neck can elicit or modulate the tinnitus perception. In terms of physiology, converging somatosensory and auditory inputs are integrated in the dorsal cochlear nucleus (DCN), an auditory brainstem nucleus receiving afferent input from the auditory nerve. It is believed that somatosensory input to this DCN plays a role in the induction of tonotopically-restricted hyperactivity in the DCN that has been correlated with tinnitus.

Unfortunately, present techniques for reducing tinnitus are inadequate. Some techniques, for example, are overly intrusive, requiring deep brain access through embedded probes, which makes these techniques undesirable for widespread use. Some techniques provide temporary relief from the tinnitus using external stimuli but fail to address the underlying causes of tinnitus in patients, leaving patient's susceptible to further tinnitus bouts, and often soon after treatment.

SUMMARY

The disclosure demonstrates stimulus timing dependent plasticity in vivo as a mechanism underlying multisensory integration. The timing rules and time course of the observed stimulus-timing dependent plasticity closely mimic those of spike-timing dependent plasticity that has been demonstrated in vitro in the dorsal cochlear nucleus (DCN). Spike-timing dependent plasticity is important for adaptive processing and is a mechanism for deemphasizing body-generated signals, such as vocalizations, by suppressing sound-evoked responses that are predicted by activation of somatosensory inputs. By manipulating spike timing dependent plasticity through unique multisensory stimulation, we have developed techniques capable of reducing and removing phantom sound perception or tinnitus, in which cross-modal plasticity is an underlying mechanism.

The disclosure provides techniques for controllably timed stimulation of both the somatosensory system and the auditory system, in such a manner, that an individual's brain activity is altered through spike-timing dependent plasticity, thereby reducing or removing tinnitus. We show that multisensory neurons in the DCN show long-lasting plasticity of sound-evoked responses and spontaneous activity when stimulated with combined somatosensory-auditory stimulation. By varying the intervals between sound and somatosensory stimuli, we show for the first time in vivo that this DCN bimodal plasticity is stimulus-timing dependent. The timing rules and time courses of the observed stimulus-timing dependent plasticity closely mimic those of spike-timing dependent plasticity that have been demonstrated in vitro at parallel-fiber synapses onto DCN principal cells. Furthermore, the degree of inhibition in neuron firing influences whether that neuron has Hebbian or anti-Hebbian timing rules. As demonstrated, anti-Hebbian timing rules reflect adaptive filtering, which in the DCN would result in suppression of sound-evoked responses that are predicted by activation of somatosensory inputs, leading to the suppression of body-generated signals such as self-vocalization.

In an embodiment, a method of treating tinnitus in a subject, includes: generating an audible stimulation signal having a first firing point and first firing period; generating a somatosensory stimulation signal to stimulate a somatosensory system of a subject, the somatosensory stimulation signal having a second firing point and second firing period; and establishing a timing order and timing difference between the first firing point and the second firing point to reduce the tinnitus, wherein the first firing period and the second firing period are to be maintained asynchronously to reduce tinnitus so that onset of the first firing period does not significantly overlap onset of the second firing period.

In another embodiment, a system for treating an auditory condition in a subject, comprises: a processor and a memory; and a bimodal stimulation system configured to, generate an audible stimulation signal having a first firing point and first firing period, stimulus onset, and/or duration, generate a somatosensory stimulation signal to stimulate a somatosensory system of a subject, the somatosensory stimulation signal having a second firing point and second firing period, stimulus onset, and/or duration, and establish a timing order and timing difference between the first firing point and the second firing point to reduce the tinnitus, wherein the first firing period and the second firing period are to be maintained asynchronously to reduce tinnitus so that the onset of the first firing period does not overlap the onset of the second firing period.

In yet another embodiment, a computer-readable storage medium having stored thereon a set of instructions, executable by a processor, for treating an auditory condition in a subject, the instructions comprises: instructions for generating an audible stimulation signal having a first firing point and first firing period, stimulus onset, and/or duration; instructions for generating a somatosensory stimulation signal to stimulate a somatosensory system of a subject, the somatosensory stimulation signal having a second firing point and second firing period, stimulus onset, and/or duration; and instructions for establishing a timing order and timing difference between the first firing point and the second firing point to reduce the tinnitus, wherein the first firing period and the second firing period are to be maintained asynchronously to reduce tinnitus so that the onset of the first firing period does not overlap the onset of the second firing period.

In another embodiment, a computer-readable storage medium having stored thereon a set of instructions, executable by a processor, for treating an auditory condition in the a subject, the instructions comprises: instructions for determining optimal parameter values for an audible stimulation signal and a somatosensory stimulation signal to alter firing rates for neurons in the auditory pathway, including but not limited to dorsal cochlear nucleus, ventral cochlear nucleus, inferior colliculus, auditory cortex, and/or other nuclei associated with tinnitus. More generally, the optimal parameter values may be determined to alter firing rates along any of the auditory and non-auditory pathways involved in the auditory condition (e.g., tinnitus).

In another embodiment, a method, for treating an auditory condition in the subject, the method comprises: determining optimal parameter values for an audible stimulation signal and a somatosensory stimulation signal to alter firing rates for neurons in the auditory pathway, including but not limited to dorsal cochlear nucleus, ventral cochlear nucleus, inferior colliculus, auditory cortex, and/or other nuclei associated with tinnitus. More generally, the optimal parameter values may be determined to alter firing rates along any of the auditory and non-auditory pathways involved in the auditory condition (e.g., tinnitus).

In some examples, the method includes increasing firing rates for the neurons in the auditory pathway, including but not limited to dorsal cochlear nucleus, ventral cochlear nucleus, inferior colliculus, auditory cortex, and/or other nuclei associated with tinnitus. More generally, the optimal parameter values may be determined to alter firing rates along any of the auditory and non-auditory pathways involved in the auditory condition (e.g., tinnitus).

In some examples, the method includes decreasing firing rates for the neurons in the auditory pathway, including but not limited to dorsal cochlear nucleus, ventral cochlear nucleus, inferior colliculus, auditory cortex, and/or other nuclei associated with tinnitus. More generally, the optimal parameter values may be determined to alter firing rates along any of the auditory and non-auditory pathways involved in the auditory condition (e.g., tinnitus).

In another embodiment, a system for treating an auditory condition in a subject, the system comprises: a processor and a memory; and a bimodal stimulation system configured to, determine optimal parameter values for an audible stimulation signal and a somatosensory stimulation signal to alter firing rates for neurons in the dorsal cochlear nucleus, ventral cochlear nucleus, and/or auditory cortex. More generally, the optimal parameter values may be determined to alter firing rates along any of the auditory and non-auditory pathways involved in the auditory condition (e.g., tinnitus).

In yet another embodiment, a method of treatment comprises: identifying, in a bimodal stimulation system, initial parameters for timing and intervals of a bimodal stimulation for a subject by identifying stimulation parameters that in the subject produce a reduction in objective measures of neural correlates of tinnitus assessed by any of an electroencephalography test, auditory brainstem response (ABR) test, or subjective measures of tinnitus perception assessed by any of a psychophysical tinnitus matching test or patient questionnaires.

In another embodiment, a system of treatment comprises: a processor and a memory; and a bimodal stimulation system configured to identify initial parameters for timing and intervals of a bimodal stimulation for a subject by identifying stimulation parameters that in a subject produce a reduction in objective measures of neural correlates of tinnitus assessed by any of an electroencephalography test, auditory brainstem response (ABR) test, or subjective measures of tinnitus perception assessed by any of a psychophysical tinnitus matching test or patient questionnaires.

In another embodiment, a computer-readable storage medium having stored thereon a set of instructions, executable by a processor, for treating an auditory condition in a subject, the instructions comprises: instructions for identifying initial parameters for timing and intervals of a bimodal stimulation for a subject by identifying stimulation parameters that in the subject produce a reduction in objective measures of neural correlates of tinnitus assessed by any of an electroencephalography test, auditory brainstem response (ABR) test, or subjective measures of tinnitus perception assessed by any of a psychophysical tinnitus matching test or patient questionnaires.

In some examples, the bimodal stimulation comprises an audible stimulation signal and a somatosensory stimulation signal.

BRIEF DESCRIPTION OF THE DRAWINGS

FIGS. 5A and 5B illustrate plots of change in firing rate for bimodal stimulation versus unimodal tone stimulation (FIG. 5A) and unimodal somatosensory stimulation (FIG. 5B), respectively.

FIG. 11A-11D illustrate plots of ABR threshold shift versus frequency for the left (exposed) and right (unexposed) ear for a noise-exposed group of subjects and for a sham group of subjects, in accordance with an example.

DETAILED DESCRIPTION

Generally, examples are described for providing multi-sensory stimuli to reduce or eliminate phantom sound perception or tinnitus. Stimulation of both the somatosensory system and the auditory system is achieved, but in a counterintuitive, timed manner, in which spacing between auditory and somatosensory stimuli is used to activate spike-timing dependent plasticity in target neurons in such a manner that spontaneous activity is reduced, thereby reducing or removing tinnitus.

Conventional bimodal stimulation techniques relied upon simultaneous stimulation of systems, with the belief that contemporaneous triggering of vagal nerve stimulation, to stimulate neuromodulatory inputs to auditory cortex from nucleus basalis, with sound stimulation would treat such conditions as tinnitus by triggering remapping of the cortical topographic frequency map. Recent studies have shown that cortical remapping is not necessary for tinnitus. To develop the present techniques, however, bimodal plasticity induction in the DCN was assessed in vivo in a different manner, by measuring sound-evoked and spontaneous firing rates before and after bimodal stimulation, and where, in these examples, the second system stimulated is the somatosensory system.

Figure 1A:
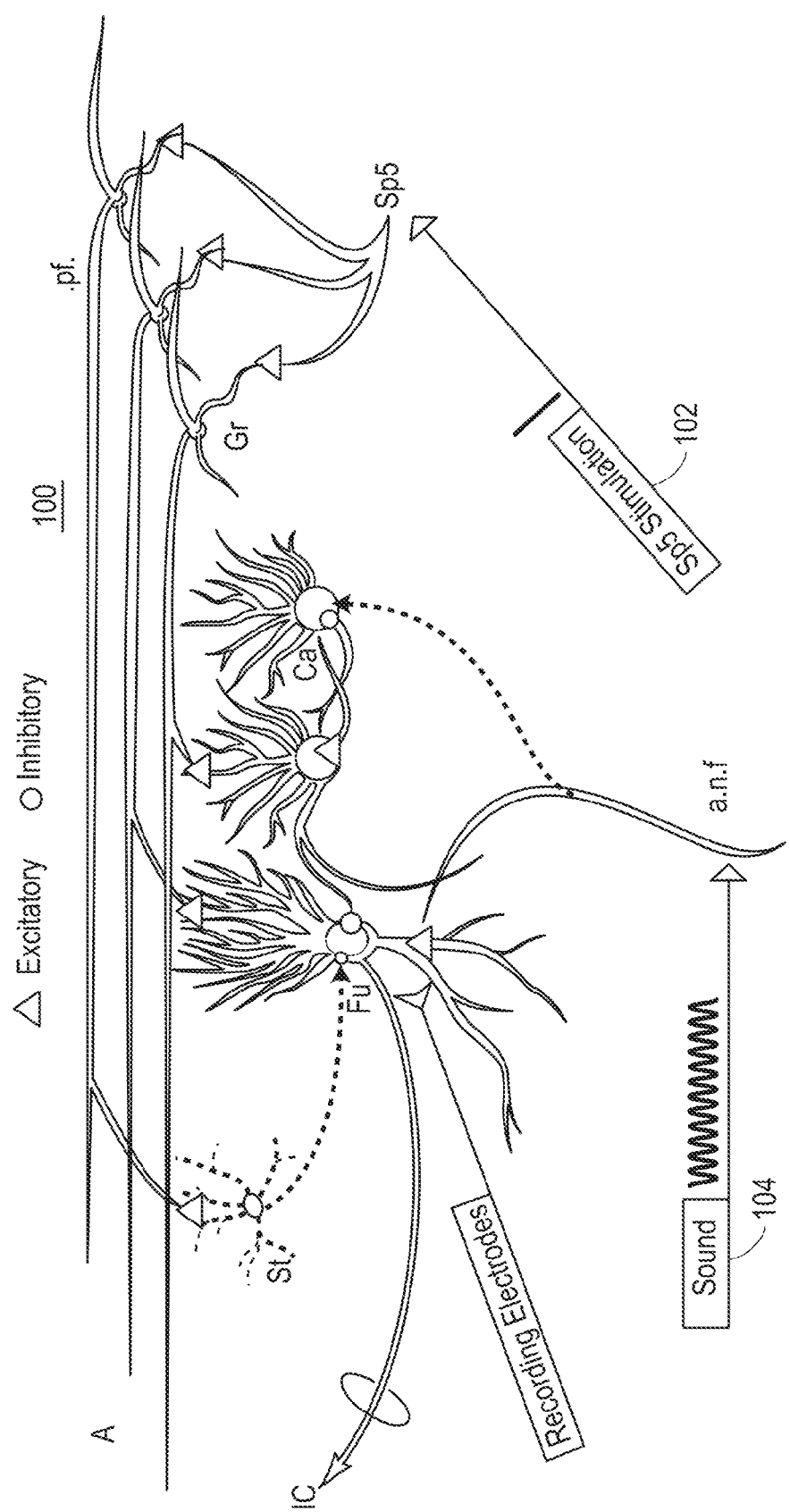
FIG. 1A is an example multisensory stimulation configuration 100 for bimodal stimulation of two different types of synapses.

FIG. 1A is an example multisensory stimulation configuration 100 for bimodal stimulation of two different types of synapses. FIG. 1A shows different cell types that connect with each other (Gr=granule cells; St=stellate cells). Stimulation of the somatosensory system is achieved through electrical pulses 102, in this example, delivered to 5p5 to activate parallel fiber-fusiform (Fu) (e.g., at the face and part of the somatosensory system—the parallel fibers connect the somatosensory system with the cochlear nucleus fusiform and cartwheel cells) and cartwheel cell (Ca) synapses (e.g., part of the cochlear nucleus), paired with a 50-ms tone burst 104 to the auditory system to elicit spiking activity in the fusiform (Fu) and cartwheel (Ca) cells. Dorsal cochlear nucleus unit responses to unimodal tones and spontaneous activity following bimodal stimulation were recorded with a multi-channel electrode 106 placed into the DCN using a standard protocol.

Figure 1B:
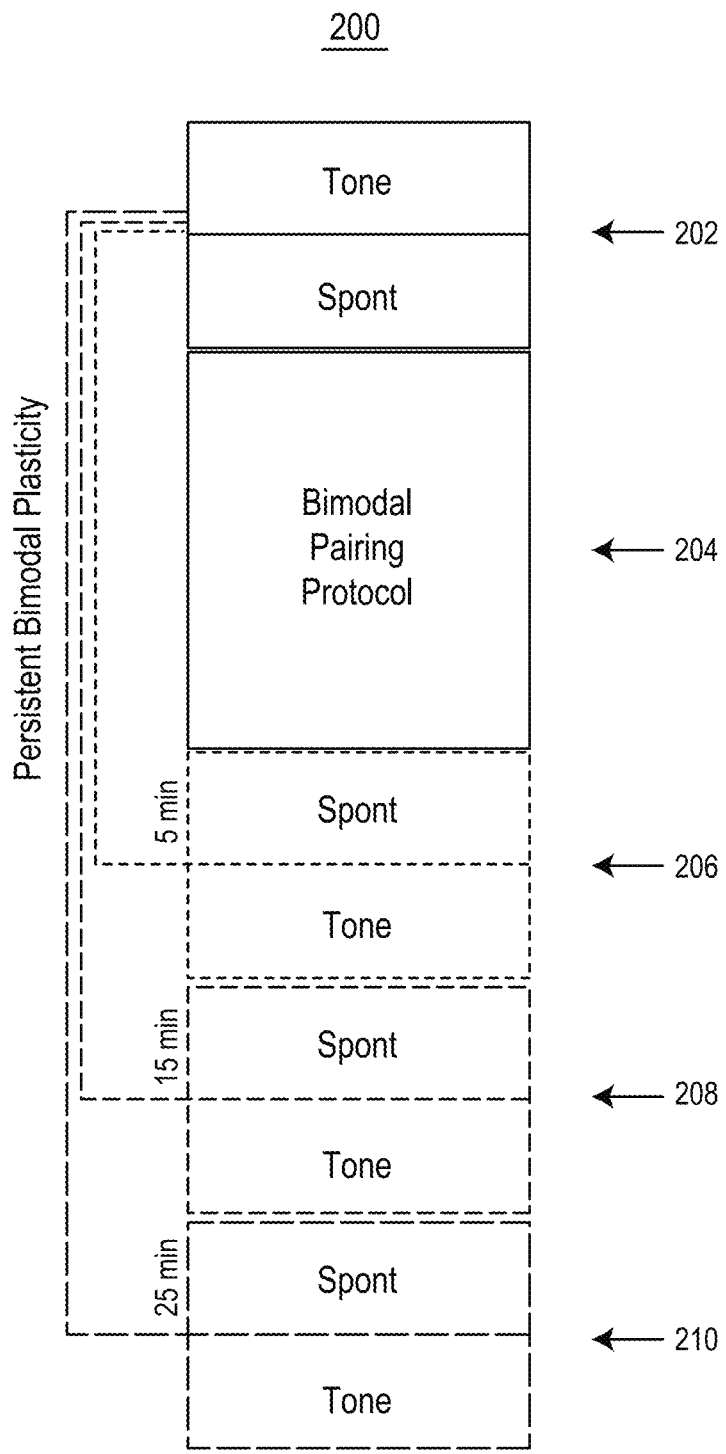
FIG. 1B illustrates an example protocol 200 for measuring the effect of bimodal stimulation on neurons, through the use of a bimodal pairing protocol, having 5 steps, in the illustrated example.
Figure 1C:
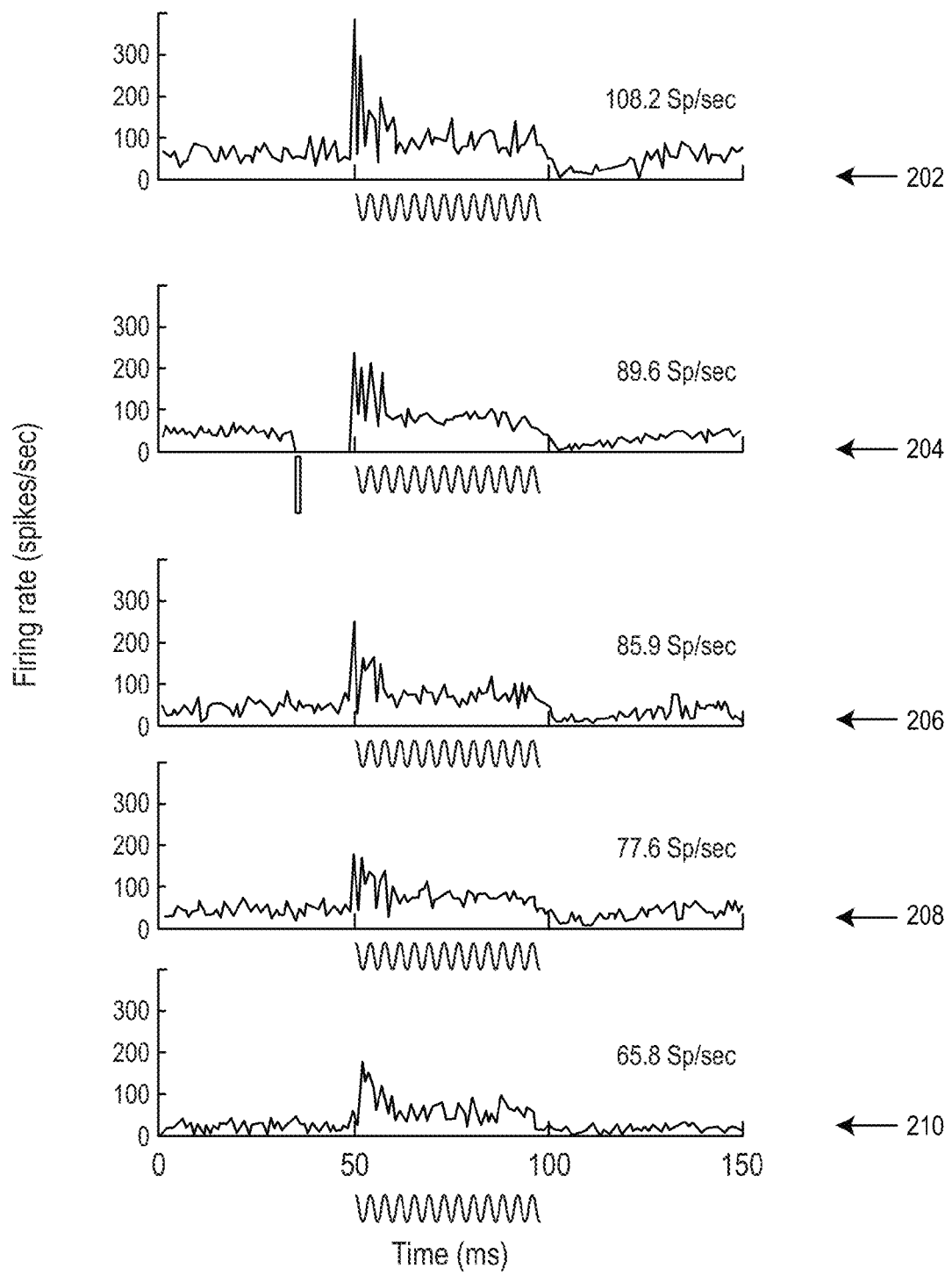
FIG. 1C illustrates five plots of firing rate versus time (a firing rate map), for each of the steps in FIG. 1B.

FIG. 1B illustrates an example protocol 200 for implementation of the bimodal stimulation, through the use of a bimodal pairing protocol. For each of the bimodal stimulation pairings in FIG. 1B a corresponding firing rate plots shown in FIG. 1C. As shown, the present techniques are able to suppress, in some examples, and enhance, in others, responses to sounds through bimodal stimulation. As represented in FIG. 1C, for example, bimodal stimulation, in particular the relative timing of such stimuli, has been adjusted such that the spontaneous activity and responses to tones (initially 202) were suppressed for 5 min (206), 15 min (208), and 25 (210) mins after bimodal stimulation (204), under different firing conditions. This resulted in the plots in FIG. 1C. Bimodal enhancement and suppression, in examples herein, were measured by comparing unimodal (auditory) response magnitudes at different times after bimodal stimulation to unimodal response magnitudes before bimodal stimulation. These are equivalent to the "late" or long-lasting changes previously described in Dehmel et al., 2012 that reflect plasticity. This "bimodal plasticity" contrasts with bimodal integration in which bimodal enhancement and suppression were measured by comparing responses during bimodal stimulation with unimodal (auditory) responses.

In any event, in some examples, the present techniques include stimulating with auditory and somatosensory stimuli and then waiting a time period to observe that the effects are still there. The results show the long-lasting effect necessary to induce long-lasting suppression of tinnitus and may be contrasted with immediate effects, which are less relevant to tinnitus suppression.

Figure 2A:
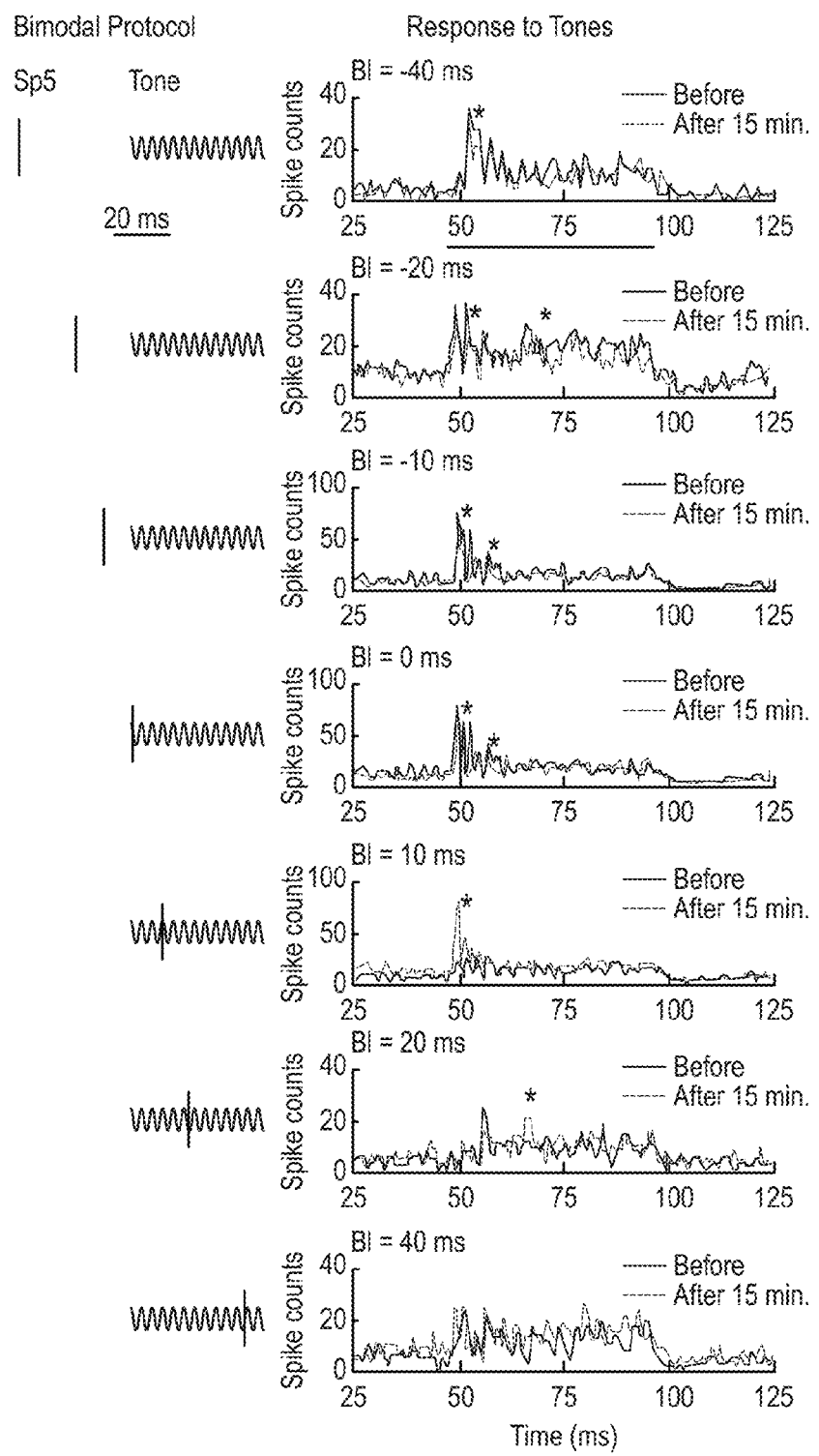
FIG. 2A illustrates plots of spike counts versus time for 7 (seven) different bimodal timing values, between a somatosensory stimulation and an auditory stimulation.

As we have shown, bimodal plasticity is stimulus-timing dependent. In vivo stimulus timing dependent plasticity has been shown to reflect underlying Hebbian and anti-Hebbian spike timing dependent plasticity (STDP). To assess stimulus-timing dependence for our techniques, in an example, the bimodal stimulation protocol (FIG. 1B) was repeated with varying bimodal intervals, e.g., 5p5 stimulation onset minus sound onset. As illustrated in the example of FIG. 2A, which shows plots of auditory response for different timings between the somatosensory stimulation and the auditory stimulation, the auditory response was suppressed after bimodal stimulation when somatosensory system stimulation (5p5) preceded the auditory stimulation, but the auditory response was enhanced if the auditory stimulation preceded the somatosensory stimulation. This corresponds to values for bimodal interval (BI) below 0 ms (e.g., −40 ms, −20 ms, −10 ms) and values for BI above 0 ms (10 ms, 20 ms, and 40 ms), respectively, i.e., where negative bimodal intervals indicate somatosensory stimulation precedes the auditory stimulation, and positive bimodal intervals indicate auditory preceding somatosensory stimulation. Bimodal plasticity was considered stimulus-timing dependent when the sound-evoked firing rates increased or decreased following bimodal stimulation at some, but not all, of the bimodal intervals tested. What we found was that all units in which responses to sound were modulated by the bimodal pairing protocol showed stimulus-timing dependence (i.e., the firing rate increased or decreased by at least 20% following at least one bimodal interval tested). The particular amount of increase or decrease in firing rate may be adjusted as discussed herein; of course, this particular amount is provided by way of example.

Figure 2B:
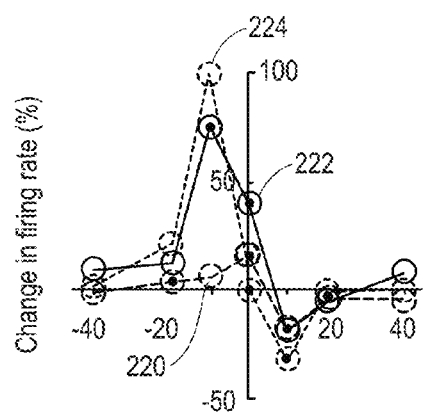
FIGS. 2B-2E each illustrate a plot of change in firing rates versus time for different times after bimodal stimuli (e.g., 5 mins, 15, mins, and 25 mins) corresponding to the protocol of FIG. 1B, for Hebbian-like (FIG. 2B), anti-Hebbian-like (FIG. 2C), enhanced (FIG. 2D), and suppressed (FIG. 2E) measurements.
Figure 2C:
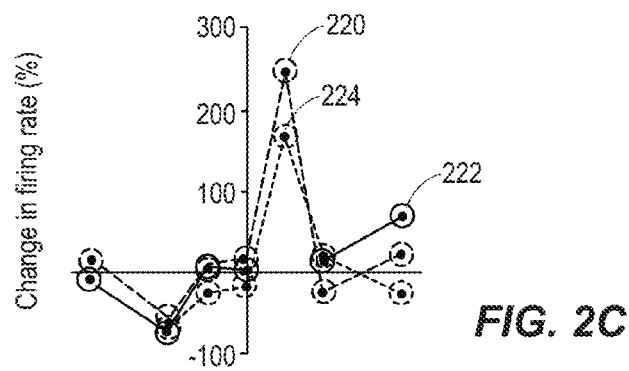
Figure 2D:
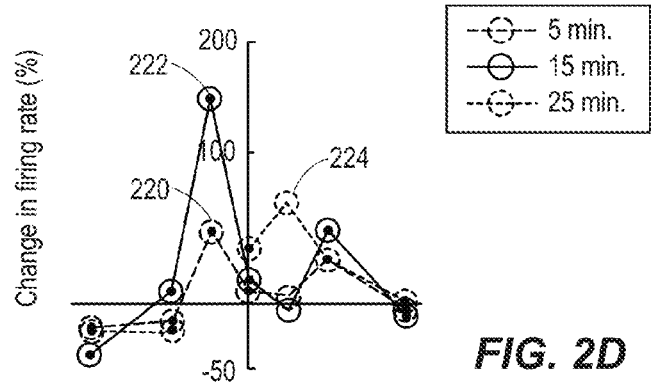
Figure 2E:
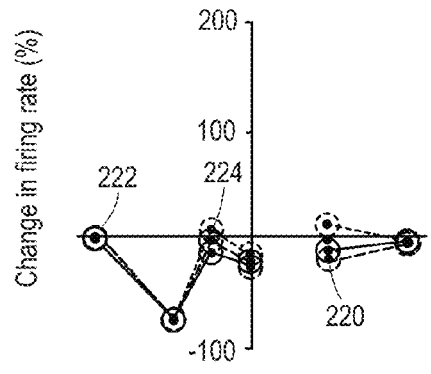
Figure 2F:
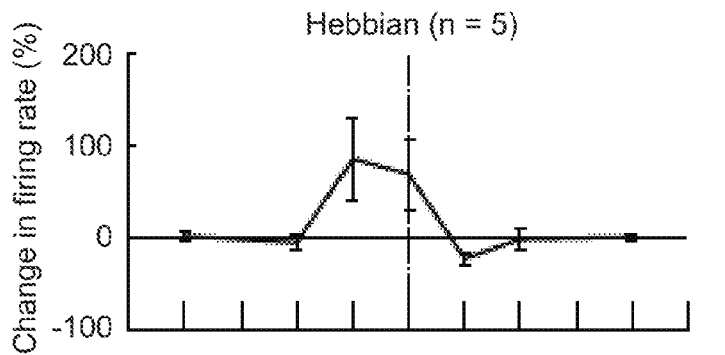
FIGS. 2F-2I each illustrate a plot of demonstrating the mean single unit timing rules for each group are shown in FIGS. 2B-2E, with corresponding identifies.
Figure 2G:
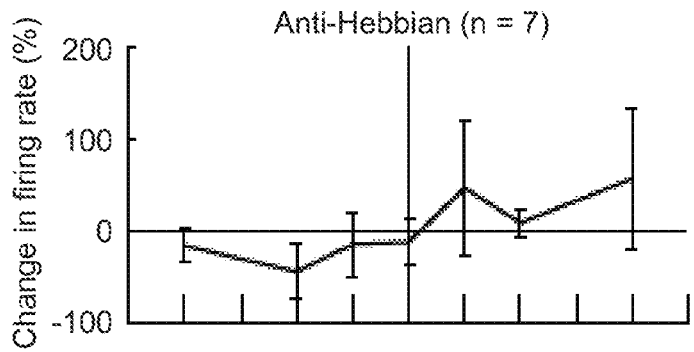
Figure 2H:
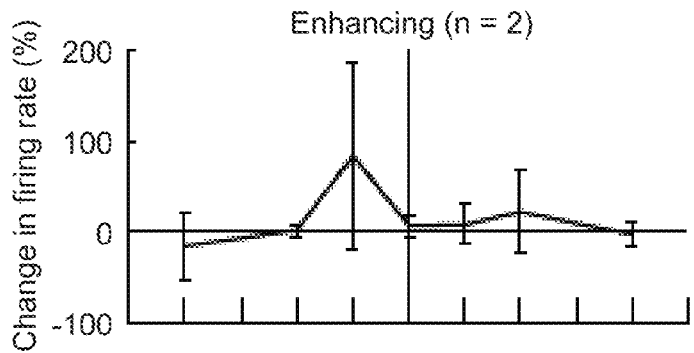
Figure 2I:
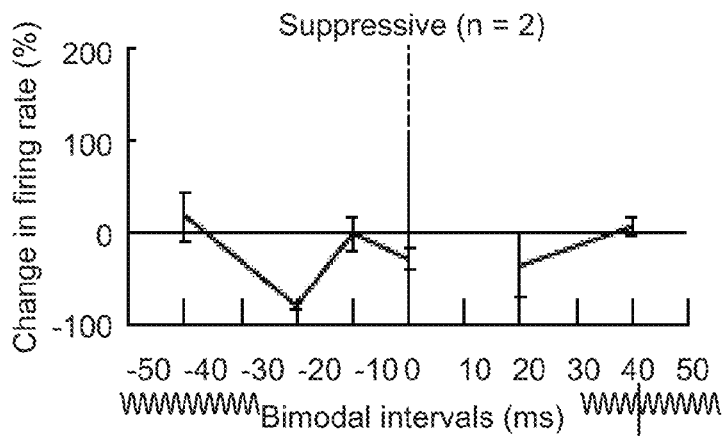

For each unit demonstrating stimulus-timing-dependent plasticity, a timing rule was constructed from the percent change in firing rate as a function of bimodal interval. The timing rules are illustrated in FIGS. 2B-2E, and correspond to those of FIG. 1B with plots for 5 mins (220), 15 mins (222), and 25 mins (224) after exposure to the bimodal stimulation. Timing rules were classified into Hebbian-like (FIG. 2B), anti-Hebbian-like (FIG. 2C), enhanced (FIG. 2D), and suppressed (FIG. 2E). Mean single unit timing rules for each group are shown in FIGS. 2F-2I, with corresponding identifies. As shown, Hebbian-like units were maximally enhanced when the somatosensory stimulation preceded auditory stimulation and maximally suppressed when auditory stimulation preceded somatosensory stimulation, likely reflecting Hebbian STDP at the parallel-fusiform cell synapse (n=5; FIGS. 2B and 2F). Anti-Hebbian-like units were maximally suppressed when somatosensory stimulation preceded auditory stimulation and maximally enhanced when auditory stimulation preceded somatosensory stimulation (n=7; FIG. 2C, 2G), likely reflecting a combination of Hebbian STDP at the parallel-fusiform cell synapse and anti-Hebbian STDP at the parallel-cartwheel synapse. Other units were either enhanced (n=2; FIGS. 2D, 2H) or suppressed (n=2; FIGS. 2E, 2I) by all bimodal pairing protocols. Although not shown, comparison of single and multi-unit clusters, meaning that with the present techniques we can record from one or more neurons using these electrodes and then we can separate some of them into single neuron (unit) responses using principal component analysis, indicated that the same Hebbian-like (n=25), anti-Hebbian-like (n=18), enhanced (n=18), suppressed (n=12) timing rules were observed in multi-unit clusters. Thirty three multi units showed a complex dependence of suppression and enhancement on the bimodal interval (not shown).

Figure 3A:
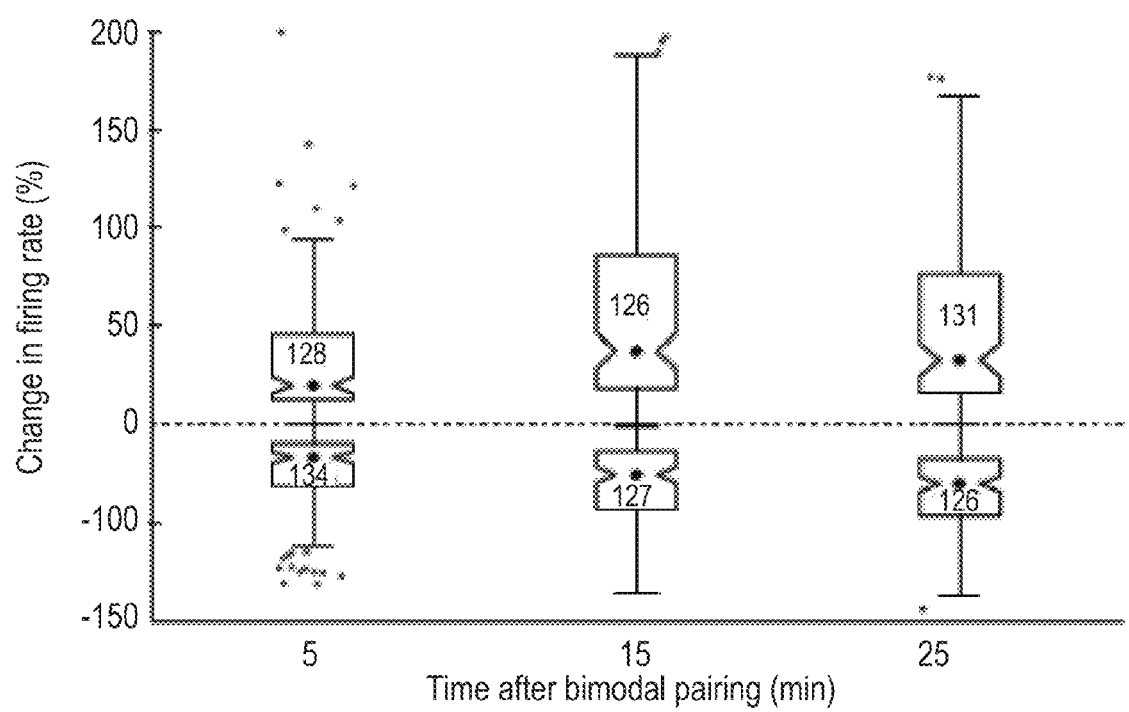
FIG. 3A illustrates a plot of a firing rate mapping, for different times after bimodal stimulation, showing maximal enhancement and suppression.
Figure 3B:
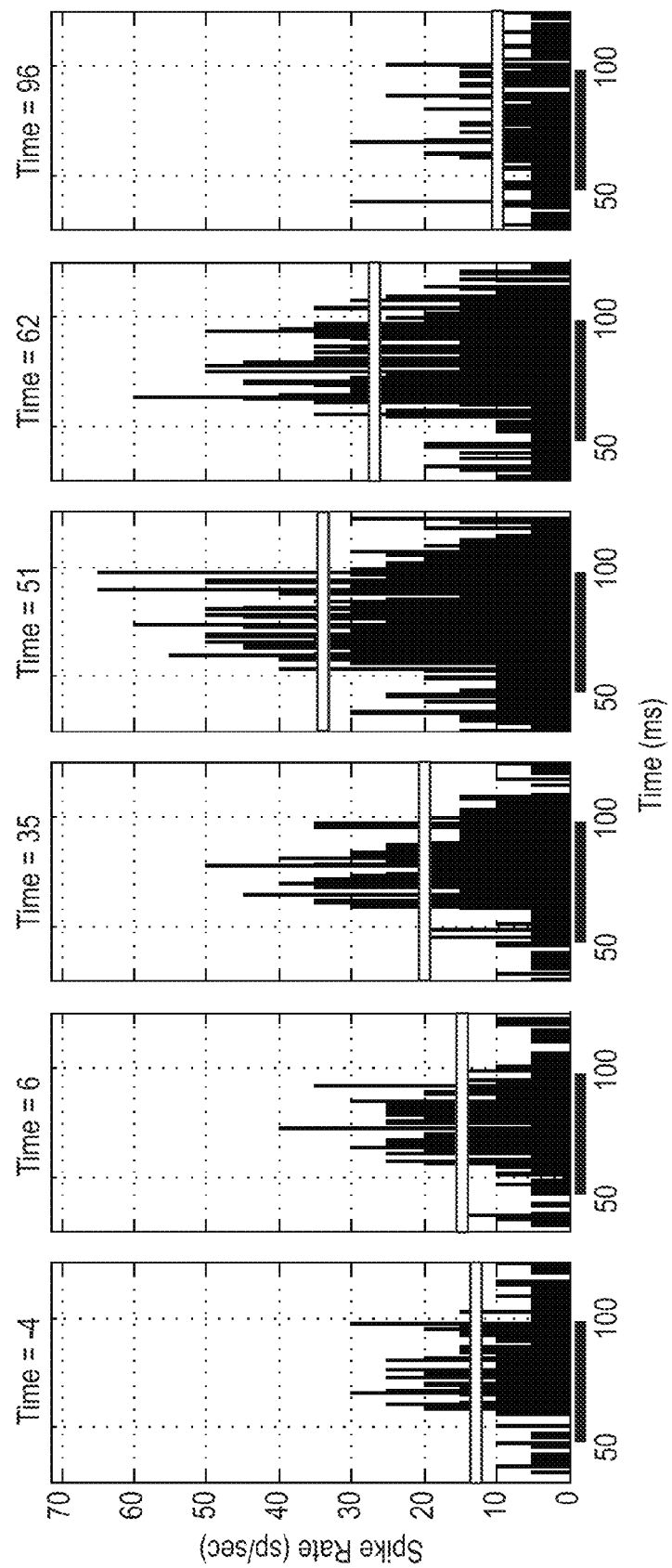
FIG. 3B illustrates a plot of spike rates for different, extended periods of time after bimodal stimulation.

Synaptic plasticity at parallel fiber synapses in the DCN develops over the course of several minutes. To compare the bimodal plasticity time course to synaptic plasticity time courses, bimodal plasticity was measured at 5, 15, and 25 minutes after bimodal stimulation, using the protocol of FIG. 1B, for both single and multi-units. The maximal enhancement and suppression and the bimodal interval that induced maximal enhancement and suppression were used to estimate the effect of bimodal stimulation on the DCN neural population. The change in firing rate following bimodal stimulation was often greater at 15 or 25 minutes than at 5 minutes after bimodal stimulation (see, e.g., FIG. 2B-E). Maximal bimodal enhancement plateaued 15 minutes following bimodal pairing and started to recover at 25 minutes, as shown in FIG. 3A (top). In contrast, maximal bimodal suppression continued to develop over 25 minutes as shown in FIG. 3A (bottom). Median maximal suppression was −28% (n=126) after 25 minutes while median maximal enhancement was 40% (n=126) by 25 minutes after bimodal pairing. These data indicate that tone responses began to recover towards baseline 25 minutes after application of the bimodal stimulus pairing. This performance is provided by way of example, however. In some examples, responses to tones recovered to baseline levels within 90 minutes after the bimodal pairing (see, e.g., FIG. 3B).

Figure 4:
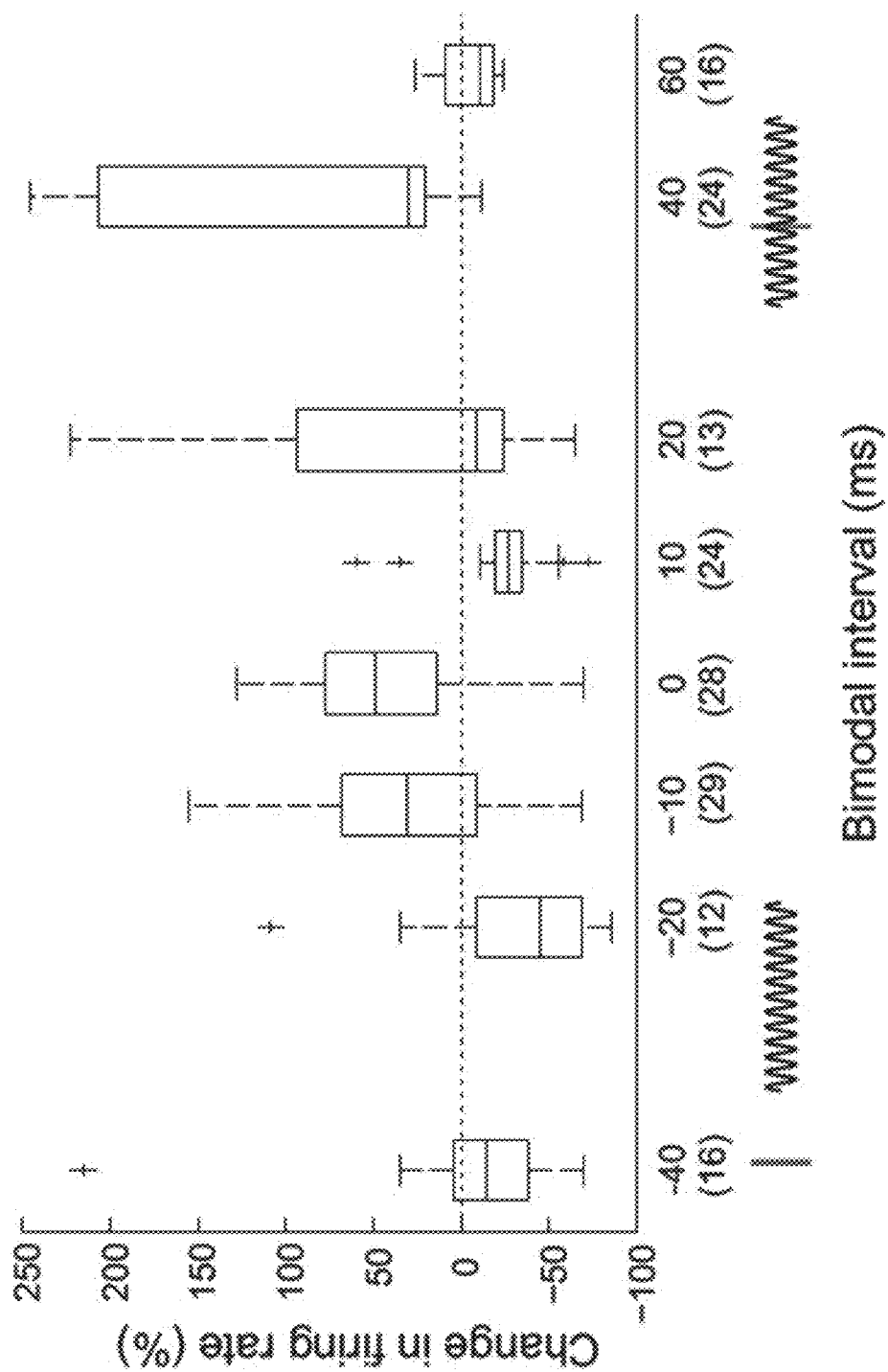
FIG. 4 illustrates a plot of change in firing rate versus bimodal interval to show a population estimate of the stimulus-timing dependence of bimodal plasticity, in accordance with an example.

To determine the proper timing and order of bimodal stimulation of the somatosensory and auditory systems, a firing rate mapping, like that of FIGS. 2F-2I and FIG. 3A, may be used to assess stimulus-timing dependent plasticity. In the illustrated example, the DCN neural population is dominated by anti-Hebbian-like stimulus-timing dependent plasticity. Having a technique to identify the maximum bimodal enhancement and suppression with corresponding bimodal intervals allowed a population estimate of the stimulus-timing dependence of bimodal plasticity in the DCN. An example is shown in FIG. 4. When the most effective bimodal pairing protocol (e.g., bimodal interval) consisted of Sp5 (somatosensory stimulation) following (auditory) tone stimulation by 20 or 40 ms, Sp5 synchronous with tone stimulation, or Sp5 preceding tone stimulation by 10 ms, bimodal stimulation was most likely to produce enhancement. In contrast, when the most effective bimodal stimulation protocol was Sp5 preceding the tone stimulation by 20 or 40 ms or following tones by 10 ms, induced bimodal suppression resulted.

We also found that our bimodal stimulation techniques induced stronger persistent effects than unimodal stimulation. Attendant to our proposed hypothesis that STDP underlies long-lasting bimodal plasticity is that paired auditory and somatosensory stimulation induce long-lasting suppression or enhancement of tone-evoked responses. To test this, changes in unimodal tone-evoked responses were measured during protocols in which the bimodal stimulus was replaced by a unimodal stimulus (i.e., with either sound or Sp5 stimulation alone). FIGS. 5A and 5B illustrate the change in firing rate for bimodal stimulation versus unimodal tone stimulation (FIG. 5A) and unimodal somatosensory stimulation (FIG. 5B), respectively. Maximal bimodal enhancement and suppression were significantly stronger than enhancement or suppression of the tone-evoked response following unimodal tone stimulation (FIG. 5A). However, only maximal suppression, and not enhancement, following bimodal stimulation was stronger than that following unimodal 5p5 stimulation (FIG. 5B). Thus, activation of both somatosensory and auditory inputs has a greater long-lasting effect on DCN unit responses than either activation of auditory or somatosensory inputs alone.

Figure 6A:
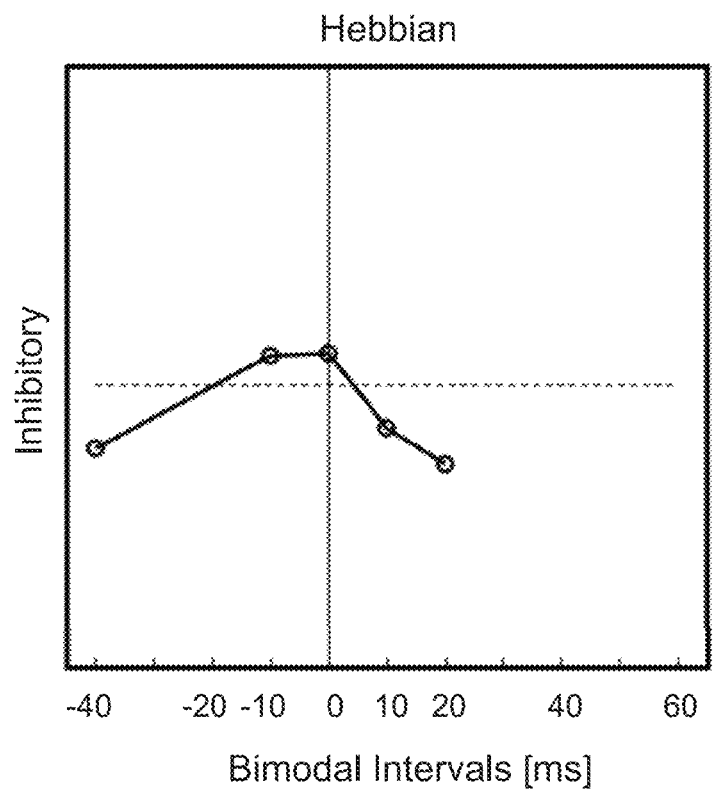
FIGS. 6A and 6B illustrate responses of six different neurons to 5p5 stimulation with either an inhibitory response (FIG. 6A) or an excitatory response (FIG. 6B), for Hebbian timing rules.
Figure 6B:
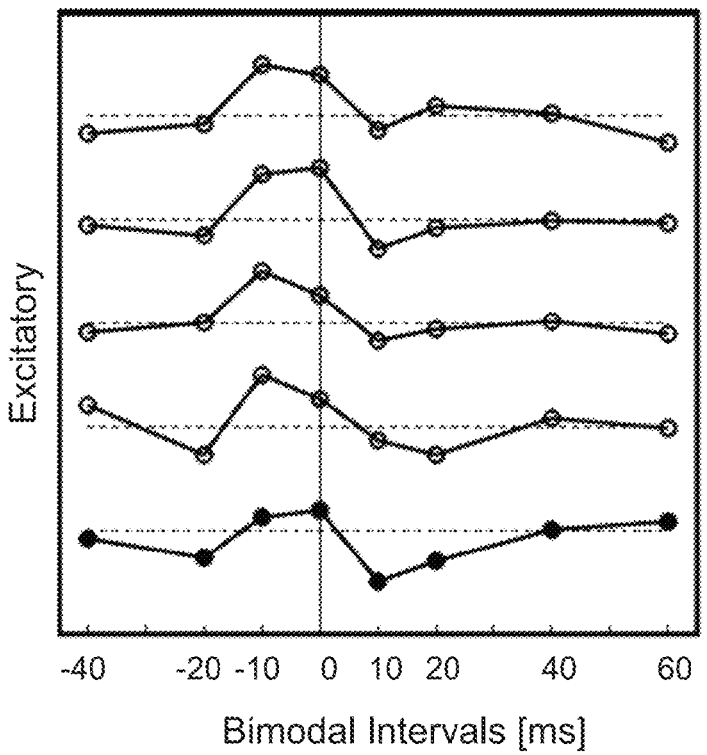
Figure 6C:
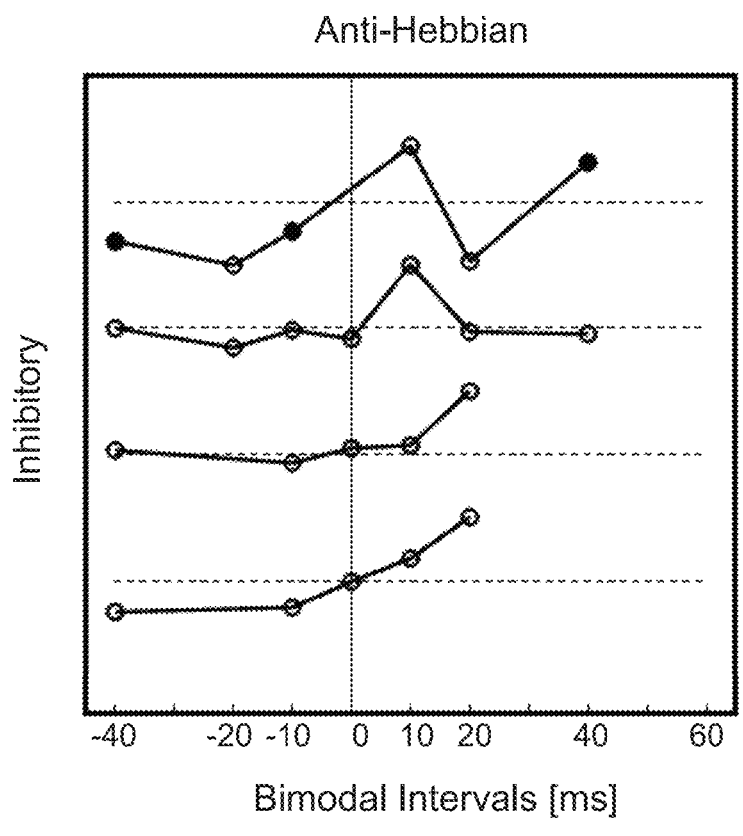
FIGS. 6C and 6D illustrate responses of six different neurons to 5p5 stimulation with either an inhibitory response (FIG. 6C) or an excitatory response (FIG. 6D), for Anti-Hebbian timing rules.
Figure 6D:
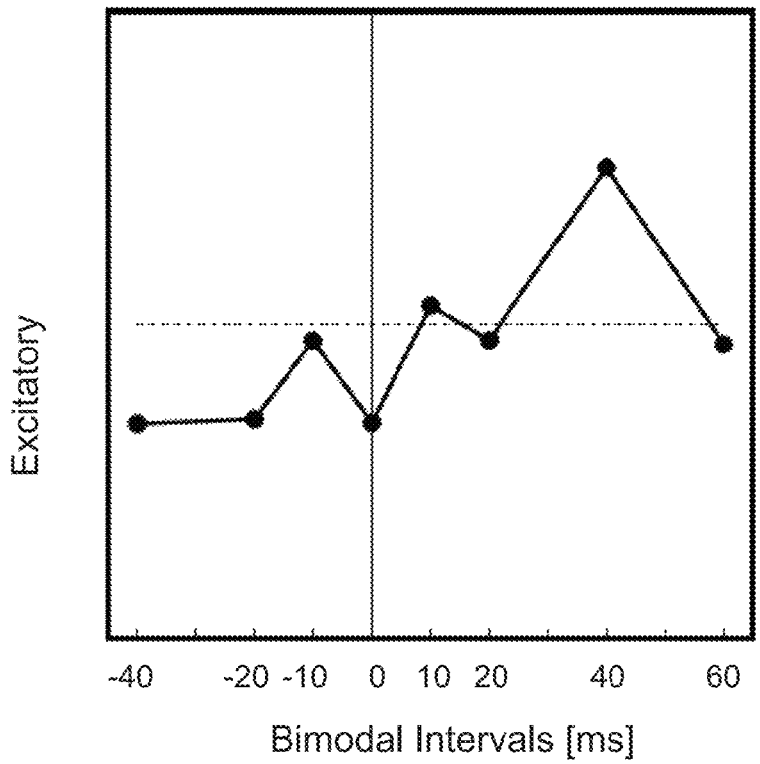

We found from our testing of variations to timing and ordering of bimodal stimuli, that units excited by Sp5 stimulation exhibited Hebbian timing rules while units inhibited by Sp5 stimulation exhibited anti-Hebbian timing rules. Activation of somatosensory neurons has previously been shown to elicit excitation, inhibition, or complex responses in DCN neurons. Somatosensory stimulation elicits either excitatory or inhibitory responses in a particular fusiform cell depending on whether input is conveyed to that fusiform cell directly from parallel fiber inputs or via inhibitory interneurons (cartwheel cells). Although 5p5 stimulation amplitude was selected to activate sub-threshold somatosensory inputs, eleven units had measurable excitatory or inhibitory responses to unimodal 5p5 stimulation and clearly defined Hebbian or anti-Hebbian timing rules. For example, in an example, we measured this by examining the effect of somatosensory stimulation on the sound-evoked response. If it affected the response but elicited no response on its own, this was defined as sub threshold. Five out of six units that responded to 5p5 stimulation with excitatory responses exhibited Hebbian timing rules, suggesting that Hebbian timing rules were driven by parallel fiber-to-fusiform cell synapses (FIGS. 6A and 6B). In contrast, four out of five units that responded to 5p5 stimulation with inhibition exhibited anti-Hebbian timing rules, suggesting anti-Hebbian dependence on parallel fiber-to-cartwheel cell synapses (FIGS. 6C and 6D). Units that did not show clear stimulus-timing dependency were just as likely to be excited or inhibited by 5p5 stimulation alone (not shown).

Figure 7A:
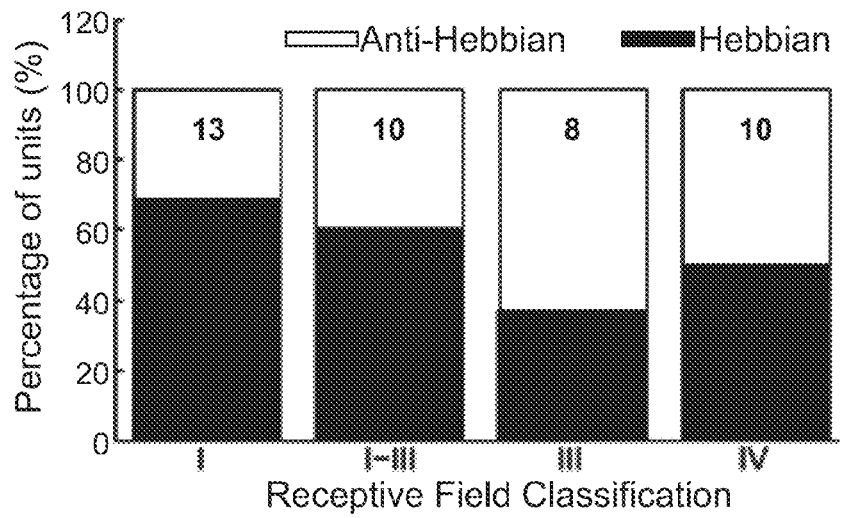
FIG. 7A illustrates a plot of percentage of neurons that experience Hebbian and anti-Hebbian-like units for types I, I-III, III, and IV, response map classifications.

We also found that bimodal stimulus timing rules correlated with inhibitory inputs, inhibitory inputs are those neural connections from other neurons that decrease the response rate of the neuron in question. To examine this, units were classified according to traditional physiological response schemes for a guinea pig by their frequency response maps (n=63 units; types 1, 11, 111, I-111, IV, and IV-T), where types refer to the amount of inhibition that is reflected in the response of the units to sound, and Type 1 has the least inhibition, Type IV has the most, and their temporal responses properties at a best frequency (n=66 units; buildup, pause-buildup, chopper, onset, and primary-like). These physiological response properties are linked to intrinsic, morphological, and network properties of DCN neurons, including their somatosensory innervation. We found that the proportion of units with Hebbian and anti-Hebbian-like timing rules correlated with the degree of inhibition reflected in their response areas. FIG. 7A, for example, shows the proportion of Hebbian and anti-Hebbian-like units for types I, I-III, III, and IV, response map classifications usually associated with fusiform or giant cells. Hebbian-like timing rules were more likely to be found in units with Type I response areas with no inhibition than in units with Type III or IV response areas with significant inhibition away from a best frequency or at high intensities. Thus, units with less inhibition tended to follow Hebbian rules and those with more inhibition tended to follow anti-hebbian rules.

Figure 7B:
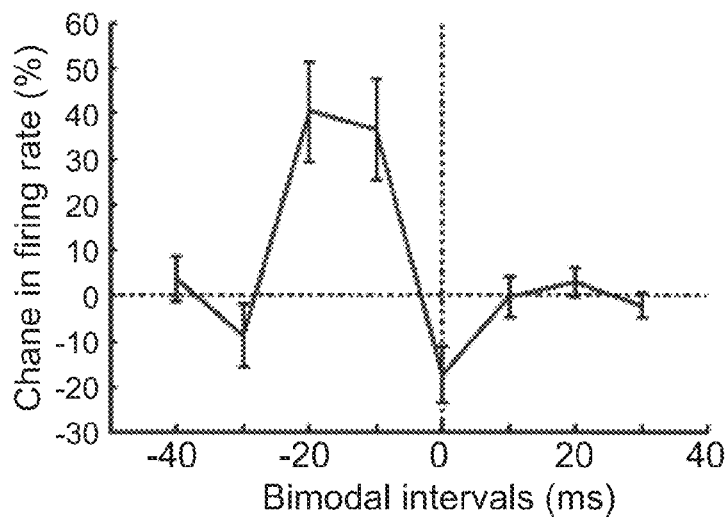
FIG. 7B illustrates a plot of changes in firing rate versus bimodal interval for buildup or pauser-buildup units with type I or type II response areas exhibiting Hebbian-like timing rules.
Figure 7C:
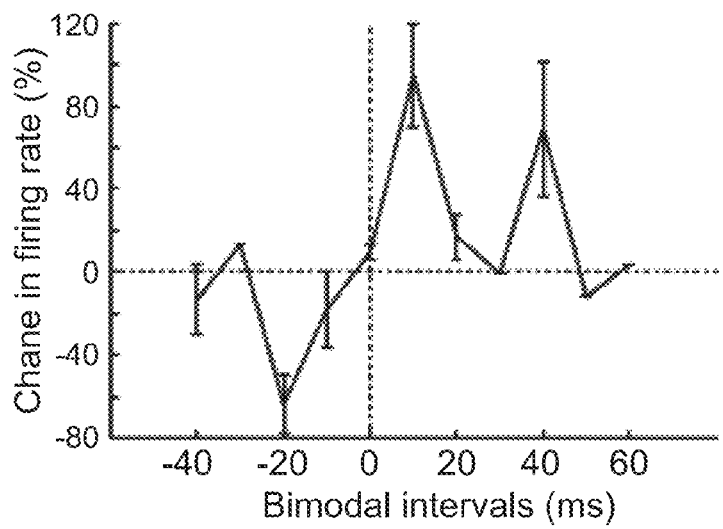
FIG. 7C illustrates a plot of changes in firing rate versus bimodal interval for buildup or pauser-buildup units with type IV or IV-T response maps exhibited only anti-Hebbian timing rules.

Timing rules and the strength of bimodal plasticity were also compared for groups of units with each combination of the temporal and receptive field response types. Two classes of neurons had consistent bimodal timing rules. Buildup or pauser-buildup units with type I or type II response areas exhibited clear Hebbian-like timing rules (FIG. 7B). In contrast, onset units with type IV or IV-T response maps exhibited only anti-Hebbian timing rules (FIG. 7C).

Figure 8:
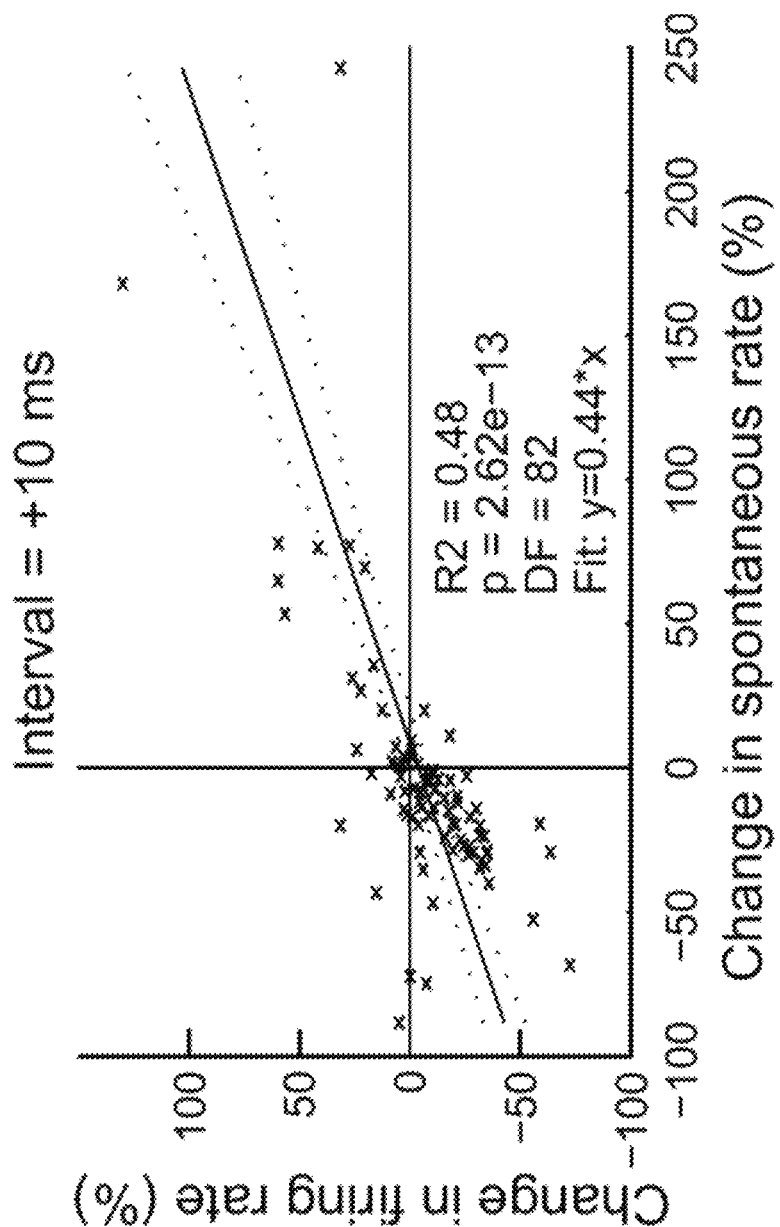
FIG. 8 is a plot of change in firing rate versus change in spontaneous rate and showing a linear regression analysis.

We also determined that spontaneous rate changes correlate with changes in sound-evoked firing rate. After bimodal stimulation the changes in sound-driven and spontaneous firing rates were significantly correlated for all bimodal intervals except for −20 ms (0.21<R2<0.48). The highest correlation in sound-driven and spontaneous firing rates was observed following the +10 ms bimodal interval (FIG. 8, linear regression analysis, DF=82; R2=0.48; p=2.62e−13). However, changes in sound-evoked and spontaneous firing rates were not significantly correlated following bimodal stimulation at an interval of −20 ms.

It is believed that part of the reasoning behind the unexpected results herein is the influence of network and intrinsic properties on bimodal plasticity. For example, the timing rule continuum, from Hebbian-like to anti-Hebbian-like to complex, developed herein seems to result from the variety of DCN neural types and suggests that intrinsic or network mechanisms act alongside STDP to control bimodal plasticity. We also believe that bimodal plasticity timing rules may also be influenced by cholinergic input from the superior olivary complex or the tegmental nuclei, which modulate STDP in the DCN, converting Hebbian LTP to anti-Hebbian LTD at parallel fiber-fusiform cell synapses.

Our determination that physiological classes of DCN neurons exhibit differing stimulus-timing dependencies implies that physiological (and likely morphological) subtypes of DCN neurons perform different functions with their multimodal inputs. Our data indicates that DCN neurons with less inhibitory influence (Type I receptive fields) are more likely to display Hebbian-like stimulus timing dependence while those with significant inhibitory influence (Type III and IV receptive fields) are more likely to display anti-Hebbian-like stimulus timing dependence. This may reflect inhibitory influences from vertical cell or cartwheel cells on post-synaptic spiking patterns which, in fusiform cells, are likely determined by long-lasting or pre-hyperpolarizing inhibition. The timing rules for STDP induction in other systems depend not only on the relative timing of pre-synaptic activity and post-synaptic spikes, but also on the number and pattern of post-synaptic spikes.

Alternatively, the source of sound-driven inhibition to DCN principal cells may also exhibit predominantly Hebbian-like stimulus-timing dependent plasticity, resulting in anti-Hebbian-like timing rules in recipient neurons. One source could be type II neurons, putative vertical cells. Type II neurons supply inhibition to fusiform and giant cells, are inhibited by somatosensory and parallel fiber input, and as we've found exhibit Hebbian-like stimulus-timing dependent plasticity.

Hebbian and anti-Hebbian STDP are important mechanisms for adaptive processing in cerebellar-like circuits. Neural responses to stimuli in these circuits exhibit long-lasting adaptation induced by correlations between primary sensory input and error signals supplied by motor control or secondary sensory inputs. We describe the first in vivo experiments evaluating mechanisms for multisensory adaptive processing in the DCN. Thus, we show that adaptive processing in the DCN is a mechanism to suppress responses to sound predicted by non-auditory signals, such as self-generated sound preceded by somatosensory input. While various techniques are described herein, including techniques for determining optimum ways to reduce tinnitus, hyperacusis, and the like, numerous variations are contemplated and will be apparent to persons of ordinary skill upon reading this disclosure. For example, the techniques may also adapt sound localization signals in the DCN to pinna or head position. A high proportion of DCN neurons exhibited anti-Hebbian-like timing rules, with responses to tones suppressed when 5p5 stimulation preceded the tone and enhanced when the tone preceded 5p5 stimulation. This observation is consistent with the hypothesis that DCN neurons cancel self-generated sounds predicted by preceding somatosensory activation.

Reports of elevated spontaneous firing rates in the DCN after tinnitus-inducing noise, implicates this structure as a site of phantom sound, or "tinnitus", generation in animal models of tinnitus. Because DCN neurons are more responsive to somatosensory stimulation following hearing damage, bimodal plasticity in DCN is believed to play a role in somatic tinnitus, i.e., the modulation of the pitch and loudness of a phantom sound perception by pressure or manipulation of the head and neck. In fact, as we've shown, the effect of bimodal stimulation, e.g., with 5p5 preceding tone stimulation, shifts from suppression in normal animals to enhancement in guinea pigs with behavioral evidence of tinnitus, which suggests that bimodal plasticity may contribute to DCN hyperactivity in tinnitus.

First Example Testing Protocols: The experimental procedures used for one set of example testing procedures, corresponding to FIGS. 1A-C, are now described. Animals: Male pigmented guinea pigs (n=5) from the University of Michigan colony (300-400 g; Ann Arbor, Mich.) were used. Surgical approach and electrode placement: Guinea pigs were anesthetized (S.D., ketamine and xylazine; 40 mg/kg, 10 mg/kg) and their heads fixed in a stereotaxic frame using a bite bar and hollow ear bars placed into the ear canals. Core temperature was maintained at 38° C. A left craniotomy was performed and a small amount of cerebellum was aspirated (leaving paraflocculus intact) to allow for visual placement of the recording electrode. Supplemental doses of ketamine and xylazine (I.M.) were administered at least hourly when indicated by response to a toe pinch. The guinea pig's condition was monitored by assessment of body temperature, respiration and heart rates, and unit thresholds.

A concentric bipolar stimulating electrode (FHC, Bowdoin, Me.) was dipped in fluorogold and placed stereotaxically into 5p5; −10 degrees below horizontal, 0.28+/−0.03 cm lateral from midline; 0.25+/−0.02 cm caudal from transverse sinus; 0.9+/−0.1 cm below surface of cerebellum. The location of the electrode was reconstructed post-mortem. A four-shank, thirty two-channel silicon-substrate electrode (site spacing=100 um, shank pitch=250 um, site area=177 um2, impedance=1-3 mOhms, available from NeuroNexus, Ann Arbor, Mich.) was placed at the DCN surface with each medial-to-lateral shank positioned within a different isofrequency layer. The electrode was then lowered 0.8-1.0 um into DCN until the uppermost site on each shank responded to sound. In one guinea pig, after completing the recording protocol the DCN electrode was moved to a more medial location and a new frequency was selected for stimulation while the 5p5 stimulating electrode remained in place.

Auditory and somatosensory stimulation: Neural activity in response to unimodal tones was recorded before and at 5, 15, and 25 minutes after the bimodal stimulation protocol (FIG. 1B). Tone signals (50 ms duration) gated with a cosine window (2 ms rise/fall time) were generated using Open Ex and an RX8 DSP (TDT, Alachula, Fla.) with 12 bit precision and sampling frequency set at 100 kHz. Sound was delivered to the left ear through the hollow ear bar by a shielded speaker (DT770, Beyer) driven by an HB7 amplifier (TDT, Alachula, Fla.). The system response was measured using a condenser microphone attached to the hollow earbar by a 'A' long tube approximating the ear canal. Sound levels were adjusted to account for the system response using a programmable attenuator (PAS, TDT, Alachula, Fla.) to deliver calibrated levels (dB SPL) at frequencies from 200 Hz to 24 kHz.

The bimodal stimulation protocol included 500 trials of the 50 ms tones combined with electrical activation of 5p5 locations known to project to DCN. Five biphasic (100 us/phase) current pulses at 1000 Hz were delivered to 5p5 through a concentric bipolar electrode using a custom isolated constant current source. The current amplitude was set to the highest level (range: 50-70 IA) that did not elicit movement artifact. The tone level (60-65 dB SPL) and frequency were fixed for the duration of the recording and were selected to reliably elicit responses to sound from most recording sites. The bimodal interval was defined as the onset of the 5p5 stimulus minus the onset of the tone, with negative values indicating 5p5-leading tone stimulation and positive values indicating tone-leading 5p5 stimulation. Varied bimodal intervals were used to assess stimulus-timing dependence of bimodal plasticity. During each recording session, the bimodal interval was randomly selected from the following intervals until all conditions were tested: −40, −20, −10, 0, +10, +20, +40, or +60 ms. For the unimodal control protocols, either the current amplitude was set to 0 uA or the sound level was set to 0 dB SPL.

Spike detection and sorting: Voltages recorded from the multi-channel recording electrode were digitized by a PZ2 preamp (Fs=12 kHz, TDT, available from Alachua, Fla., USA) and band-pass filtered (300 Hz-3 kHz) before online spike detection using a fixed voltage threshold set at 2.5 standard deviations above background noise (RZ2, TDT, Alachua, Fla., USA). Spike waveform snippets and timestamps were saved to a PC using Open Explorer (TDT, Alachua, Fla., USA). Waveform snippets were sorted using principal components of the waveform shape and K-means cluster analysis with fixed variance (95%) and 5 clusters (OpenSorter, TDT, Alachua, Fla., USA). Clusters with a J2 value above Ie-5 were not considered well isolated and were combined. Single units were identified by consistency of waveform shape and amplitude. Spikes up to 15 ms after the onset of the current stimulation were contaminated by electrical artifacts and ringing and excluded from all analyses. While multi-unit clusters could not be identified as isolated single units, the waveform shapes, amplitudes, and response properties were consistent over the duration of the recording.

Experimental design: To characterize unit responses to sound according to standard classification schemes, tone stimuli were presented before any 5p5 stimulation. Tone levels (0-85 dB SPL; 5 dB steps) and frequencies were varied (200 Hz-23 kHz; 0.1 octave steps) between trials (200 ms trial; 50 ms tone) with each condition repeated 10-20 times. The current amplitude for 5p5 stimulation was set at the highest amplitude that did not elicit ipsilateral facial twitches (60-80 IA). At the current amplitude presented, few units showed supra-threshold responses to somatosensory stimulation, but clearly sub-threshold responses were elicited, as evidenced by the bimodal effects.

Unimodal trials were recorded at four time points: before, and 5, 15, and 25 minutes after the bimodal stimulation protocol (FIG. 1B). Responses were recorded to unimodal tones (TONE) presented at the same level (60-65 dB SPL) as in the bimodal stimulation protocol (200 trials, 5 trials per second). Two minutes of spontaneous activity (SPONT) was also recorded at each time point before and after the bimodal stimulation protocol. All unimodal tones and rate level functions were at the same frequency used for bimodal stimulation. The entire recording block in FIG. 1B (the combined pairs 202-210) lasted for 30-35 minutes with unimodal recordings at each time point lasting for 5-7 minutes and the bimodal stimulation protocol lasting for 4-5 minutes. The recording block in FIG. 1B was repeated randomly for each bimodal interval tested (−40, −20, −10, 0, 10, 20, 40, or 60 ms). In one guinea pig, control recording blocks were repeated in which unimodal tone or Sp5 stimuli replaced the bimodal stimuli. After the final recording block, the responses to unimodal tones were measured every 15-30 minutes for as long as possible to assess recovery after bimodal stimulation.

Unit characterization: All units were characterized by best frequency, threshold, frequency response map and temporal response patterns at best frequency. Response maps were constructed by computing the sound-evoked firing rate during the 50 ms tone minus spontaneous firing rate measured during the last 50 ms of each trial. Excitation or inhibition was considered significant when the firing rate was greater than 2.5 standard deviations above or below the mean spike rate of all trials with no sound. Post-stimulus time histograms were constructed for each unit from 50-200 trials with the tone level 10-30 dB above threshold and frequency within 0.1 octave of the identified best frequency. Unit classification by receptive field and post-stimulus time histogram provide indirect evidence for the synaptic drive and intrinsic processing, respectively, of individual neurons in DCN.

FIGS. 9-16 result from other example testing that we performed to use stimulus-timing dependent bimodal plasticity to asses STDP metaplasticity in a guinea pig model of tinnitus. We found that bimodal plasticity timing rules were broader and more likely to be anti-Hebbian in guinea pigs with tinnitus than in sham guinea pigs or those without tinnitus after noise damage, which suggests that tinnitus may be linked to metaplasticity of STDP in the DCN.

As discussed further below, in this example protocol testing, guinea pigs were exposed to a narrowband noise that produced a temporary shift in auditory brainstem response thresholds known to produce tinnitus. Sixty percent of guinea pigs developed tinnitus according to behavioral testing by gap-induced prepulse inhibition of the acoustic startle. Following noise-exposure and tinnitus induction, stimulus-timing dependent plasticity was measured by comparing responses to sound before and after paired somatosensory and auditory stimulation with varying intervals and orders. What we found was that timing rules in animals with verified tinnitus were broader and more likely to be anti-Hebbian than timing rules in sham animals or noise-exposed animals that did not develop tinnitus. Furthermore, exposed animals with tinnitus had weaker suppressive responses than either sham animals or exposed animals without tinnitus. Broader timing rules combined with weaker bimodal suppression in animals with tinnitus suggested that somatosensory inputs to the DCN have a strengthened, enhancing effect in tinnitus. These results suggested that tinnitus development was linked to DCN spike-timing dependent plasticity, and thus provided further confirmation of what we described above that the present techniques provide potential tinnitus therapies.

As demonstrated, STDP in animals with tinnitus is compared to those animals without tinnitus. That these further experiments further demonstrated that the techniques herein, such as ways in which one can change the firing rate in the DCN using bimodal stimulation based on the ordering and spacing, can be used to find the specific orders and intervals of bimodal stimulation that lead to a decrease in firing rate of the majority of neurons that send the signal to the auditory cortex. Thus these further experiments provide additional examples in neurons that may be contributing to the tinnitus percept of specific timing rules and techniques for determining timing rules that create increases or decreases in such firing rates. From these timing rules, we can take those rules that decrease the firing rates to treat tinnitus. For example, the role of bimodal STDP in the DCN is to identify spatiotemporal patterns in auditory nerve activity correlated with somatosensory inputs. In the normal system, narrow STDP timing rules heighten or suppress the responsivity of DCN neurons to auditory nerve inputs that are tightly correlated with somatosensory events. Broader timing rules in tinnitus animals would increase the likelihood of a somatosensory event triggering anti-Hebbian or Hebbian plasticity, leading to heightened responsivity to spontaneous, as well as driven, auditory nerve spiking patterns. The resulting hyperactivity could be a neural representation of tinnitus. This mechanism may act cooperatively with the decreases in granule cell resistance observed after noise exposure that further enhance the strength of somatosensory inputs. Furthermore, the corresponding decrease in bimodal suppression in tinnitus animals would further enhance the hyperactivity. The tinnitus-associated changes in bimodal stimulus-timing dependent plasticity suggest that somatosensory inputs have a greater influence on DCN neural activity in animals that developed tinnitus than in those that did not. A similar process is found in visual cortex, where broadened STDP timing rules after visual deprivation cause long-term potentiation of spontaneous inputs to visual cortex at lower spontaneous firing rates than in the normal visual cortex.

From this example, we noticed a number of effects from endemic to shifts in bimodal stimulation effects over certain frequency ranges, which is particular useful as the frequency range for a patients tinnitus sensitivity will vary from patient to patient, making identifying useful operating ranges of bimodal stimulation important.

We demonstrated that narrow-band noise exposure centered at 7 kHz induced temporary threshold shifts between 7 and 16 kHz. Noise exposure induced a TTS as demonstrated by auditory brainstem response (ABR) thresholds. For example, ABR thresholds in the exposed ear (FIG. 11A) but not the unexposed ear (FIG. 11B) were elevated immediately after exposure and recovered to baseline by 1 week after noise exposure. Maximum threshold elevation was 35 dB (mean) +/−3.5 dB (s.d.) at 9 kHz after the first exposure and 19 dB (mean) +/−2.1 dB (s.d.) at 10 kHz after the second exposure with thresholds elevated in a band from the exposure frequency to 2 octaves above the exposure frequency. ABR thresholds in sham-exposed guinea pigs were not elevated above baseline in either ear (FIG. 11C and FIG. 11D). Data for post exposure 1 (230), recovery 1 (232), post exposure 2 (234), and recovery 2 (236), and final (238) are all shown.

Figure 12A:
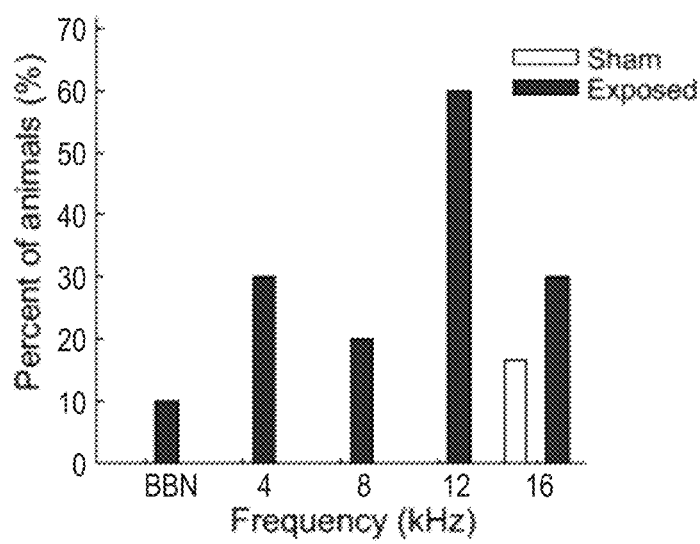
FIG. 12A illustrates percent of sham (white bars) and exposed (black bars) guinea pigs that show evidence for tinnitus in different frequency bands.

We also demonstrated that exposure to narrowband noise induced tinnitus in the 12-14 kHz band in 60% of guinea pigs. Gap-induced prepulse inhibition of acoustic startle (GPIAS) was used to assess each guinea pig for evidence of a frequency specific tinnitus percept. During baseline startle testing, all guinea pigs exhibited normal gap detection with smaller startle responses when there was a gap than when there was no gap. All guinea pigs exhibited normalized startle responses below 0.5 during baseline, with the normalized startle response defined as the ratio of the startle response amplitude with gap prepulse (AG) to the startle response amplitude without gap (ANG). Impaired gap detection, which was considered evidence for tinnitus, was identified by significantly elevated normalized startle responses. Following the TTS-inducing noise exposure, 60 percent of exposed guinea pigs were identified as having tinnitus in the 12-14 kHz band, half of which also showed evidence for tinnitus in either the 4-8 kHz, 8-10 kHz, or 16-18 kHz bands (FIG. 12A). Guinea pigs with evidence for tinnitus in the 12-14 kHz bands were thus placed into the Exposed with Tinnitus (ET) group. The remaining 40% of exposed guinea pigs that showed no evidence for tinnitus in any tested frequency band were placed into the Exposed with No Tinnitus (ENT) group, while the sham animals were considered as a separate group (Sham).

Figure 12B:
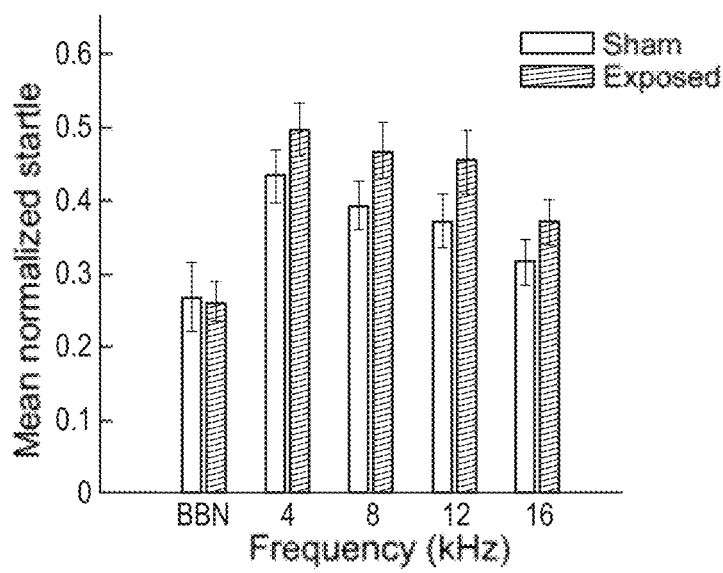
FIG. 12B illustrates a normalized startle response amplitudes in each frequency band for exposed animals (black bars) compared to sham animals (white bars).
Figure 12C:
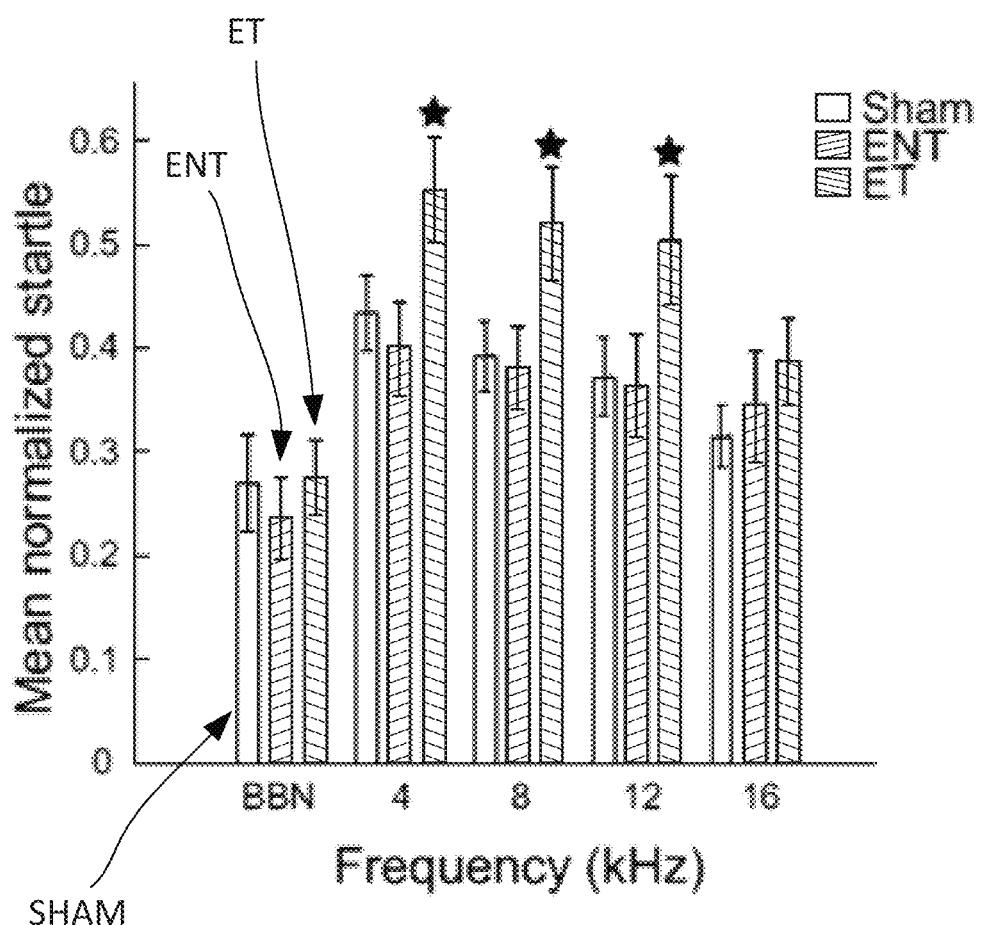
FIG. 12C illustrates a normalized startle response amplitudes in each frequency band for tinnitus animals (ET) compared to animals without tinnitus (ENT) and sham animals.

To validate the ET and ENT groupings, gap detection ability was compared between all exposed and sham guinea pigs (FIG. 12B), and between the ET, ENT and sham guinea pigs (FIG. 12C). The normalized startle response was not significantly elevated for any frequency band in all exposed guinea pigs (FIG. 12B). However, normalized startle responses were significantly elevated, indicating impaired gap detection ability, for the 4-6, 8-10, and 12-14 kHz bands in the ET group but not in the ENT group (FIG. 12C). The normalized startle response was not significantly elevated for the BBN background signal or the 16-18 kHz background signal either in the ET group or the ENT group (FIG. 12C).

We found that bimodal plasticity timing rules were predominantly anti-Hebbian and suppressing in noise-exposed animals. We measured the stimulus-timing dependence of bimodal plasticity and demonstrated predominantly Hebbian-like timing rules in normal animals. In order to separate noise-exposure driven changes in neural mechanisms from those associated with tinnitus, stimulus-timing dependent bimodal plasticity was first compared between principal cell units from Sham (n=100 units) and Exposed (n=288 units) guinea pigs and then between exposed animals that developed tinnitus (ET) or did not develop tinnitus (ENT). Bimodal plasticity was assessed by identifying significant changes in sound-evoked average firing rates 15 minutes after bimodal stimulation. The dependence of bimodal plasticity on stimulus timing was confirmed by repeatedly measuring bimodal plasticity using the protocol in FIG. 1A and varying the bimodal interval (10, 20, and 40 ms) and order (Sp5 or tone leading) in the bimodal pairing protocol. Bimodal intervals were classified as eliciting significant bimodal plasticity if the firing rates before and 15 minutes after were significantly different (t-test, $p<0.05$).

Figure 13A:
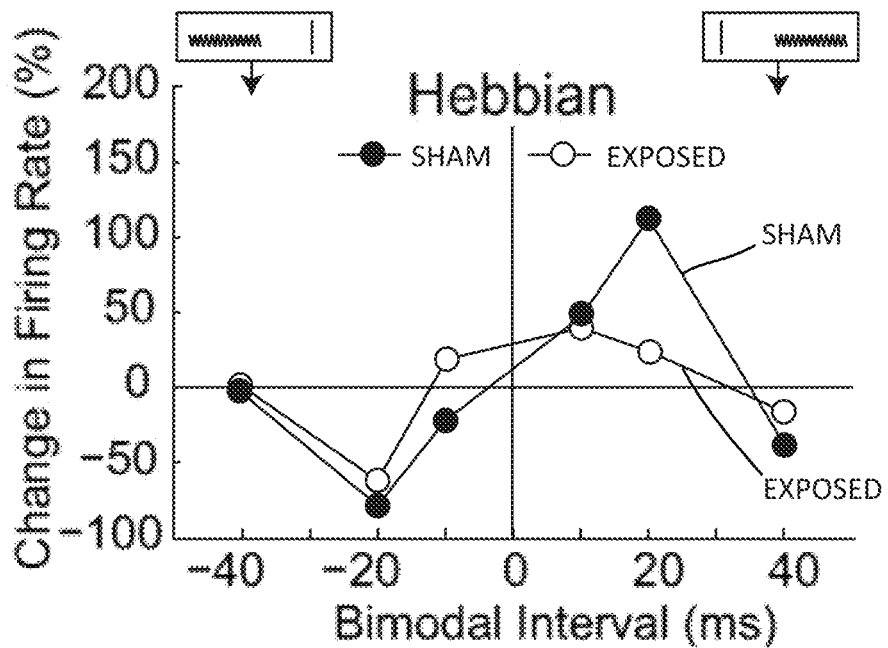
FIG. 13A illustrates two examples of single-unit Hebbian timing rules, one from a sham and one from a noise-exposed guinea pig. A cartoon at the top of the panel demonstrates the relative order of Sp5 and sound stimuli. A vertical line in the cartoon represents the Sp5 stimulus and the sinusoid represents the tone stimulus.

Timing rules were constructed for each unit by plotting the change in sound-evoked firing rates observed 15 minutes after various bimodal pairing orders and intervals. These timing rules were classified as Hebbian-like (n=132; examples from sham and noise-exposed animals shown in FIG. 13A), anti-Hebbian-like (n=69; examples from sham and noise-exposed animals shown in FIG. 13B), enhancing (n=44), or suppressing (n=143). In units with Hebbian-like timing rules, sound-evoked firing rates increased after bimodal stimulation when Sp5 stimulation preceded tone onset and decreased after bimodal stimulation when Sp5 stimulation followed tone onset (FIG. 13A). Note that the temporal window for enhancing bimodal plasticity is broader in this unit from a noise-exposed animal from the ET group, with enhancement observed after bimodal intervals of −10, 10, and 20 ms. In contrast, in the unit from the sham animal enhancement is only observed with bimodal intervals of 10 and 20 ms. In units with anti-Hebbian-like timing rules, sound-evoked firing rates increased 15 minutes after Sp5 stimulation followed tone onset and decreased 15 minutes after Sp5 stimulation preceded tone onset (FIG.

13B). Responses in the remaining units were only enhanced or suppressed following bimodal stimulation at the tested bimodal intervals (individual units not shown).

Figure 13B:
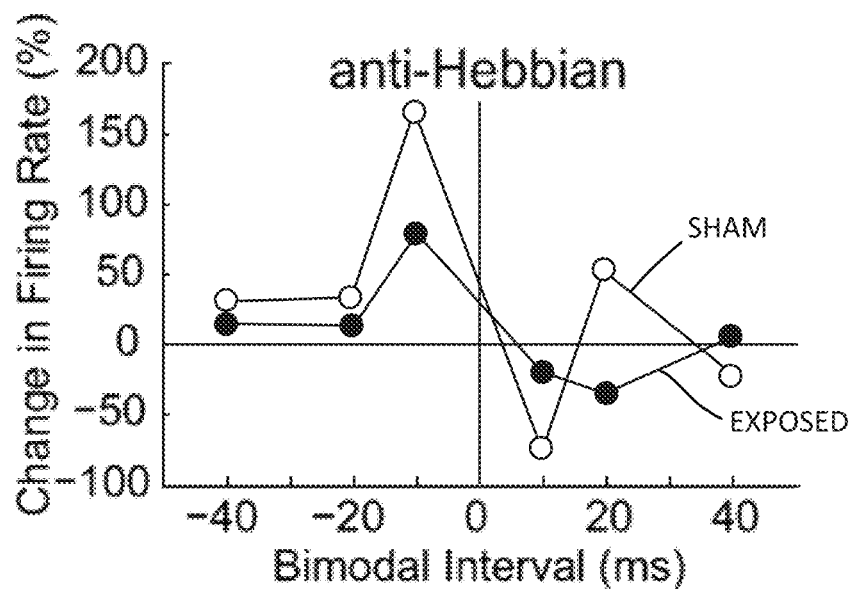
FIG. 13B illustrates two examples of single unit anti-Hebbian timing rules, one from a sham and one from a noise-exposed guinea pig.
Figure 13C:
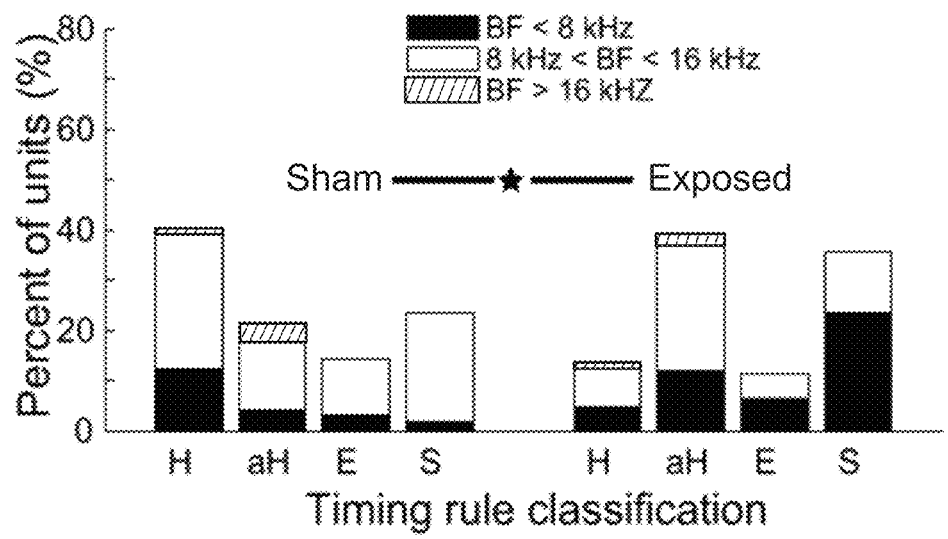
FIG. 13C illustrates the percent of principal units that showed Hebbian-like (H), anti-Hebbian-like (aH), enhancing (E) and suppressing (S) timing rules from sham (left) and noise-exposed (right) animals. Stacked bars indicate units from below (black), within (white), and above (grey) the damaged frequency region.

Units from sham animals were distributed among the timing rule classes in proportions similar to normal animals, with most units showing Hebbian-like timing rules (FIG. 13C, left column). In contrast, after noise exposure, units with anti-Hebbian and suppressive timing rules were significantly more prevalent (Chi Squared proportion test; Sham vs. Exposed; DF=3; $Chi^2$=25.2564; $p<0.0001$) than Hebbian or enhancing units (FIG. 13C, right column). Further breakdown of units into those with BFs within the TTS frequency region (8-16 kHz) and those outside these regions (below 8 kHz and above 16 kHz) reveal that units within the TTS frequency region comprised the highest percentages of units in the anti-Hebbian class.

Figure 13D:
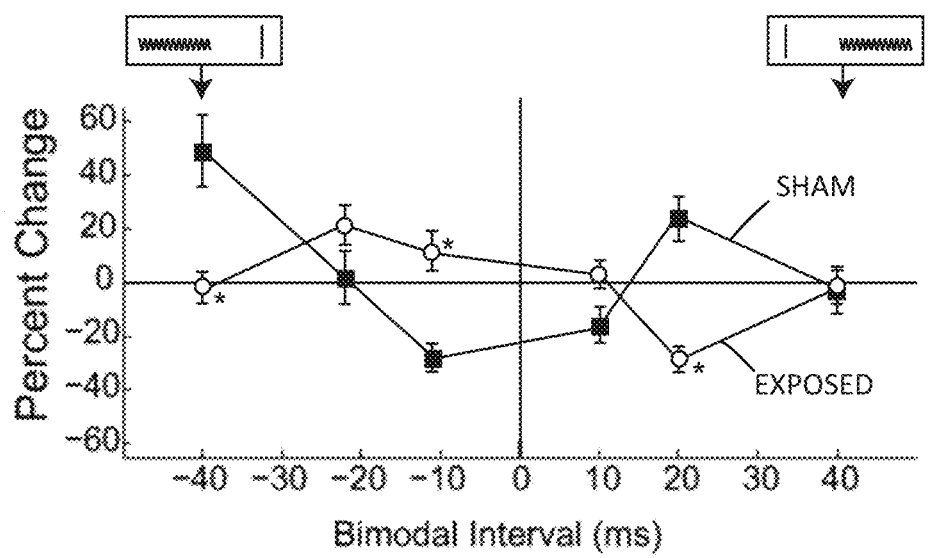
FIG. 13D illustrates timing rules shifted from Hebbian in sham animals to anti-Hebbian in exposed animals. Mean timing rules showing bimodal plasticity of sound-evoked firing rates for units from sham and exposed guinea pigs.

Mean timing rules estimate the effect of somatosensory-auditory pairing at specific intervals on DCN population activity. Mean population timing rules from all sham and exposed units 15 minutes after bimodal stimulation revealed a shift in the population timing rules from Hebbian-like to anti-Hebbian-like in the noise-exposed animals (FIG. 13D). In sham animals, the mean population timing rule was Hebbian-like, with enhancement of sound-evoked firing rates when Sp5 preceded sound stimulation (positive values) and suppression when Sp5 stimulation followed sound stimulation (negative values; FIG. 13D, sham). In noise-exposed animals, the reverse occurred, with suppression of sound-evoked firing rates for Sp5 preceding sound stimulation and enhancement with Sp5 following sound stimulation (FIG. 13D, exposed). A two-way ANOVA with exposure group (Group) and bimodal interval (BI) revealed a significant main effect of bimodal interval and a significant interaction between bimodal interval and exposure group (Group–F(1)=1.38, p=0.240; BI–F(5)=5.37, $p<0.001$; Exposure Group×Bimodal Interval–F(5)=14.47, $p<0.001$). Bimodal intervals for which there were significant differences between exposure groups according to Tukey-Kramer's post-hoc tests are designated in FIG. 13D by stars.

Figure 14A:
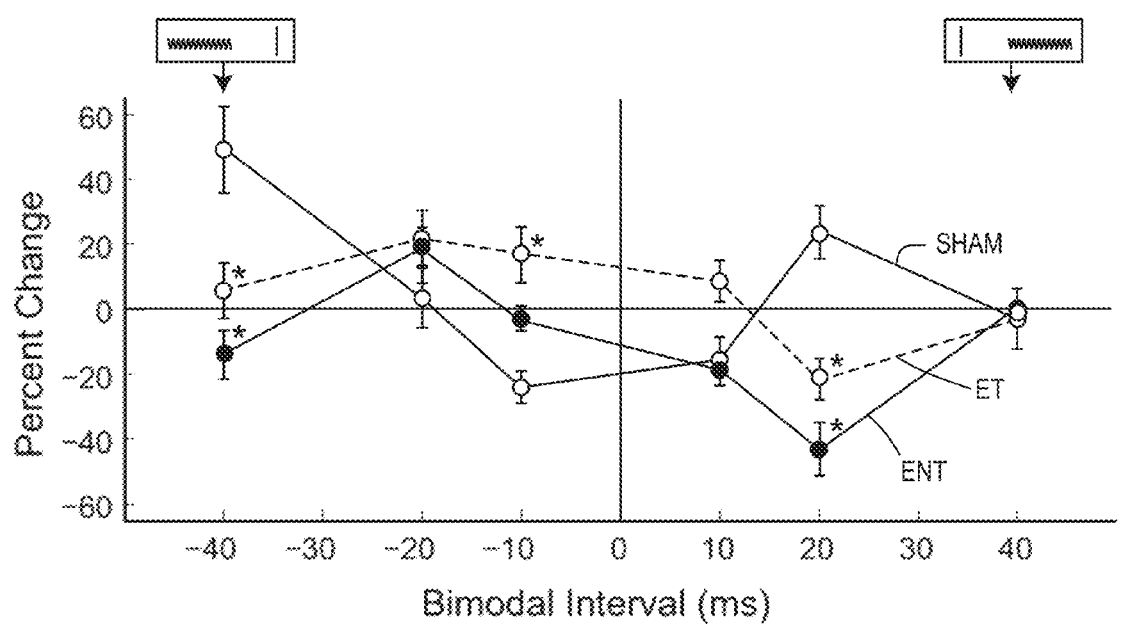
FIG. 14A illustrates mean timing rules showing bimodal plasticity of sound-evoked firing rates for units from sham, ENT, and ET guinea pigs. A cartoon at the top of the panel demonstrates the relative order of Sp5 and sound stimuli, where a vertical line represents the Sp5 stimulation and the sinusoid represents the tone stimulus.

We found that anti-Hebbian bimodal enhancement was broader in guinea pigs exhibiting tinnitus, while suppressive bimodal plasticity was broader in animals without tinnitus. To establish tinnitus-specific differences in bimodal stimulus-timing dependent plasticity, we compared responses between Sham (n=100 units), ENT (n=63 units), and ET (n=225 units) guinea pigs before and 15 minutes after bimodal stimulation of varying orders and intervals. Mean population timing rules for ET, ENT, and sham units revealed that bimodal plasticity was converted from Hebbian-like to anti-Hebbian-like timing rules in both the ET and ENT groups (FIG. 14A). In the ET animals there were more bimodal intervals at which enhancement occurred (−40, −20, −10, and 10 ms) than in the ENT group (only −20 ms), revealing a broadening of the timing rules for the enhancement phase of the curve in the ET animals. While firing rate suppression was observed at +20 ms for both ET and ENT animals, there was a broadening of the suppressive phase of the curve in the ENT animals, with suppression at both +10 and +20 ms as compared to only +20 ms in the ET animals (FIG. 14A). The broadening of the timing rules in the enhancement phase in ET animals and in the suppressive phase in ENT animals was in contrast to narrow, Hebbian-like timing rules in sham animals, in which maximal enhancement and suppression were found at bimodal intervals of +20 ms and −10 ms respectively. A two-way ANOVA with tinnitus group (TG) and bimodal interval (BI) revealed significant main effects of tinnitus group and bimodal interval and a significant interaction between bimodal interval and exposure group (TG–F(2)=4.02, p=0.018; BI–F(5)=4.72, $p<0.001$; TG×BI–F(10)=7.34, $p<0.001$). Bimodal intervals for which there were significant differences between tinnitus groups according to Tukey-Kramer's post-hoc tests are shown as stars in FIG. 14A.

Figure 14B:
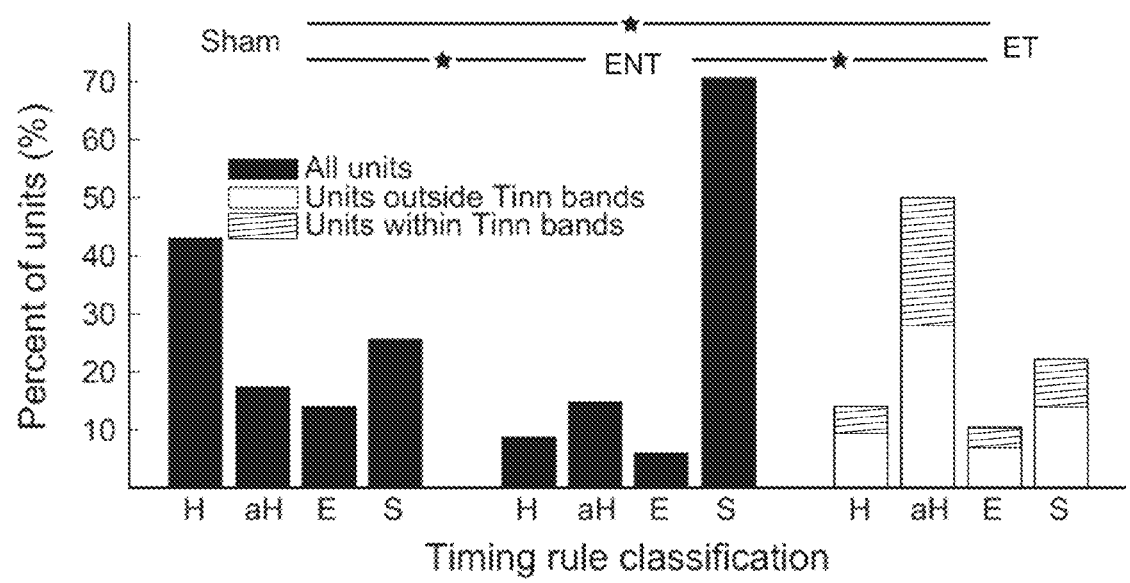
FIG. 14B illustrates the percent of units that showed Hebbian-like (H), anti-Hebbian-like (aH), enhancing (E) and suppressing (S) timing rules from sham (left), ENT (middle) and ET (right) animals.

Corresponding with the shifts in population timing rules, anti-Hebbian-like units were most common in ET animals while suppressive units were predominant in ENT animals (FIG. 14B; $Chi^2$=52.82; DF=11; $p<0.001$, stars in FIG. 14B). The shift towards anti-Hebbian-like units in ET animals was more prominent in units within the tinnitus frequency bands.

We also demonstrated that timing rules were broader and anti-Hebbian in noise-exposed animals. Above, we measured the stimulus-timing dependence of bimodal plasticity to reveal the contribution of spike-timing dependent synaptic plasticity to bimodal plasticity. In these examples, we recorded responses from Sham (n=100 units), ENT (n=63 units), and ET (n=225 units) guinea pigs before, 3 and 15 minutes after bimodal stimulation with varying orders and intervals (FIG. 13A).

Mean population timing rules from all sham and noise-exposed units 3 and 15 minutes after bimodal stimulation revealed that noise exposure shifts the population timing rule from Hebbian-like to anti-Hebbian-like in noise-exposed animals (FIG. 13B). In sham animals, both 3 and 15 minutes after bimodal stimulation, the mean population timing rule was Hebbian-like, with enhancement of sound-evoked firing rates when Sp5 preceded sound stimulation and suppression when Sp5 stimulation followed sound stimulation (FIG. 13B, labeled 302). In noise-exposed animals, the reverse occurred, with suppression of sound-evoked firing rates for Sp5 preceding sound stimulation and enhancement with Sp5 following sound stimulation (FIG. 13B, labeled 306).

We also demonstrated that timing rules were broadest in noise-exposed animals with tinnitus compared to those without tinnitus. Mean population timing rules for ET, ENT, and sham units revealed that long-lasting bimodal plasticity 15 minutes after bimodal stimulation was converted from Hebbian-like to anti-Hebbian-like timing rules in both the ET and ENT groups, but were broader in only the ET group (FIG. 13C). Additionally, in ENT animals, maximal enhancement and suppression were found at bimodal intervals of −20 ms and +20 ms respectively, similar to what was observed in sham guinea pigs with maximal enhancement and suppression observed at 10 ms and −20 ms respectively. However, in ET animals, maximal enhancement and suppression were observed at the broadest bimodal intervals tested (+40 and −40 ms), suggesting that bimodal plasticity timing rules broaden in association with tinnitus.

We found that anti-Hebbian bimodal plasticity was dominant in animals exhibiting tinnitus, while suppressive bimodal plasticity was dominant in animals without tinnitus. Timing rules were constructed for individual units from responses 15 minutes after bimodal stimulation and were classified following the scheme previously described as Hebbian-like (n=132), anti-Hebbian-like (n=69), suppressing (n=143), or enhancing (n=44) timing rules. Units from sham animals were distributed among the timing rule classes similarly to units from normal animals but after noise exposure, anti-Hebbian-like units were most common in ET animals while suppressive units were predominant in ENT animals (FIG. 14A). This corresponds with the shift in the population timing rule from Hebbian-like to anti-Hebbian-like (FIG. 13C).

Mean timing rules are shown for Hebbian, anti-Hebbian, and suppressive units from sham and ET animals in FIGS. 14B-G. Hebbian-like timing rules were similar and highly variable in both sham and ET animals (FIG. 14B-C). Additionally, bimodal suppression was weaker in ET animals than in sham animals (FIG. 14F-G).

Figure 15A:
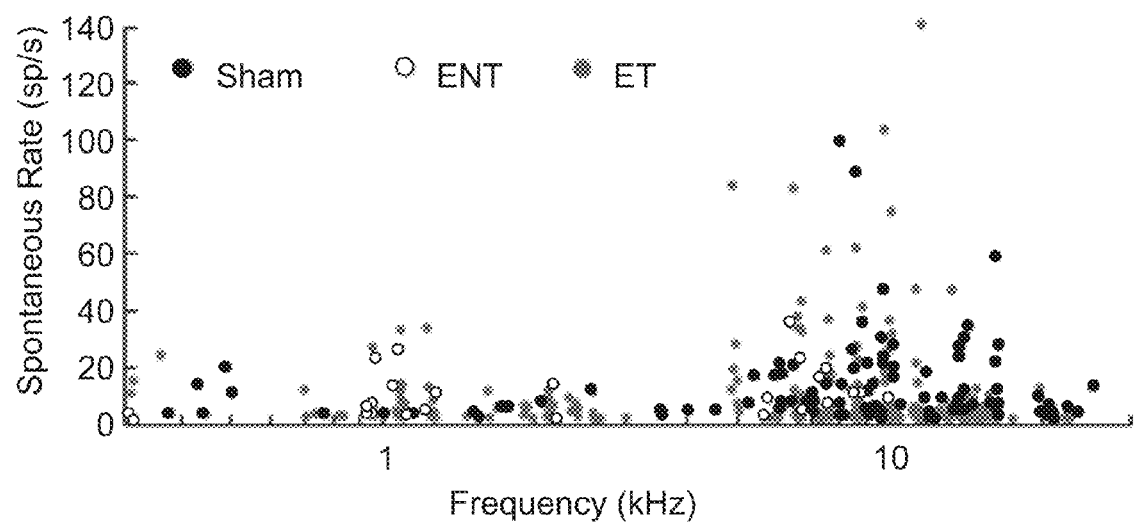
FIG. 15A illustrates spontaneous firing rates before any bimodal stimulation for each unit as a function of each unit's best frequency for sham, ENT, and ET units.
Figure 15B:
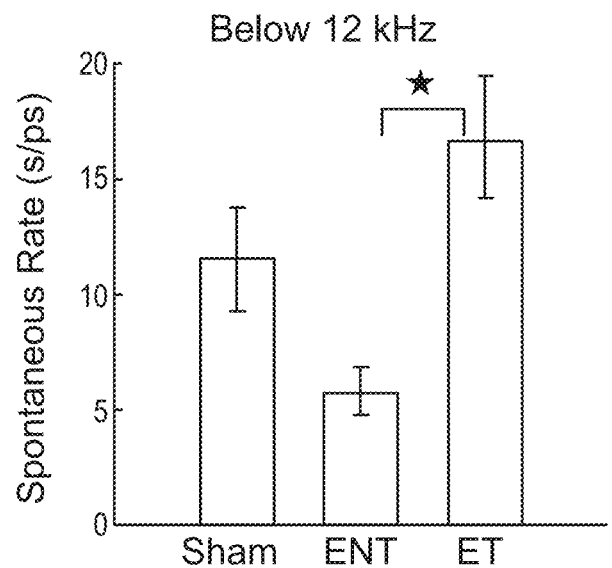
FIG. 15B illustrates mean spontaneous rates for units with best frequencies below 12 kHz.
Figure 15C:
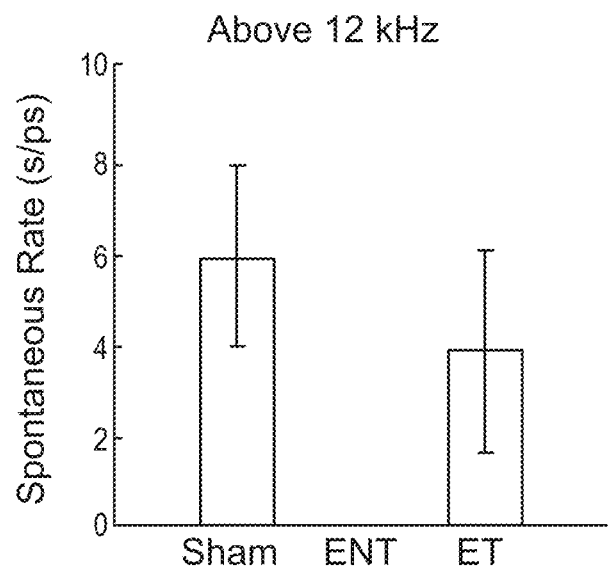
FIG. 15C illustrates mean spontaneous rates for units with best frequencies above 12 kHz.
Figure 15D:
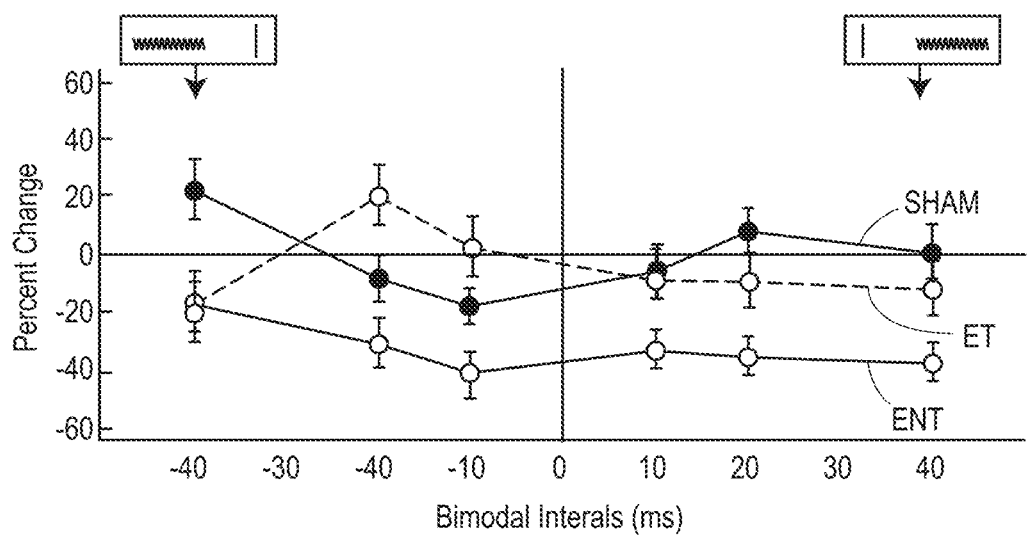
FIG. 15D illustrates a mean timing rules show bimodal plasticity of spontaneous firing rates for units from sham, ENT, and ET guinea pigs.

We also found that anti-Hebbian bimodal plasticity of spontaneous rates was dominant in noise-exposed guinea pigs exhibiting tinnitus, while suppressive bimodal plasticity of spontaneous rates was dominant in animals without tinnitus. Tinnitus is associated with spontaneous hyperactivity in the DCN and other auditory structures. Spontaneous firing rates measured before any bimodal stimulation revealed elevated spontaneous firing rates in the ET group in frequency regions with threshold shifts and evidence for tinnitus (below 12 kHz; FIGS. 15A and 15B) but not above 12 kHz (FIGS. 15A and 15C). It is therefore important to assess the influence of bimodal stimulation on subsequent spontaneous activity in sham, ENT, and ET animals. FIG. 15D plots the change in spontaneous activity observed in DCN neurons 15 minutes after various bimodal pairing orders and intervals in the three groups. These timing rules constructed from changes in spontaneous rates in units from ENT animals were generally suppressive. In contrast, units from ET animals exhibited anti-Hebbian-like timing rules with enhancement at the −20 ms intervals and less suppression at all positive intervals than the ENT animals. A two-way ANOVA with tinnitus group (TG) and bimodal interval (BI) revealed significant main effects of tinnitus group and a significant interaction between bimodal interval and exposure group (TG–$F(2)=14.06$, $p<0.0001$; BI–$F(5)=1.12$, $p=0.35$; TG×BI–$F(10)=2.41$, $p=0.008$).

Figure 16:
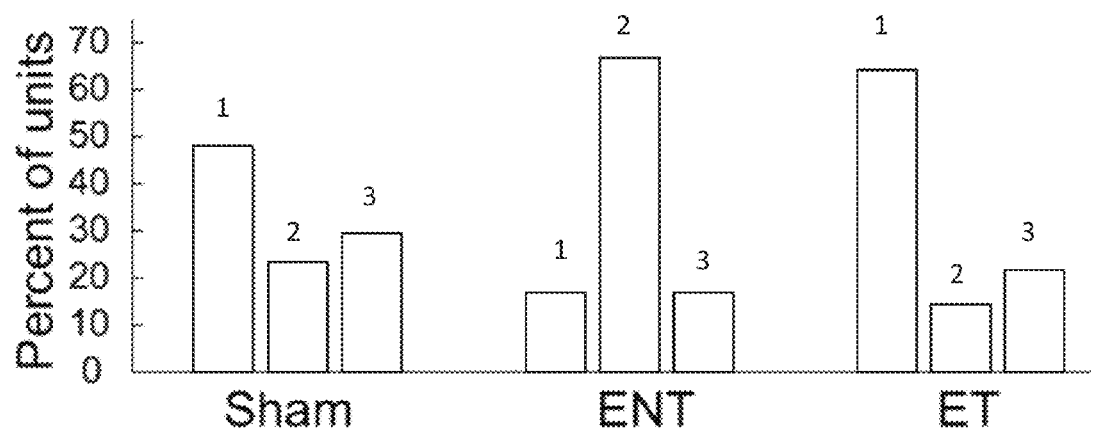
FIG. 16 is a plot of a distribution of responses to Sp5 stimulation for different test groups (sham, ET, and ENT), in accordance with an example.

Further still, we demonstrated that exposed with tinnitus animals had more excitatory responses to Sp5 stimulation, over animals that were not exposed with tinnitus. Responses to Sp5 stimulation alone were recorded to identify whether the distribution of excitatory, inhibitory, and complex unimodal Sp5 responses differed with TTS-inducing noise exposure and with tinnitus (FIG. 16). Data plot 1 is the excitatory, unimodal response case. Data plot 2 is the mixed response case. Data plot 3 is the inhibitory unimodal response case. Unimodal Sp5 responses were more likely to be excitatory and less likely to be inhibitory in ET animals than in sham animals. In contrast, unimodal responses were more likely to be complex (E/In) in ENT animals.

Thus, as shown, to identify changes in stimulus-timing dependence associated with noise-exposure, bimodal plasticity timing rules were compared between sham and all noise-exposed animals. We observed three significant noise-exposure associated changes: 1) timing rules were more likely to be anti-Hebbian than Hebbian, 2) timing rules were broader, and 3) timing rules were more likely to be suppressive than enhancing. To identify changes specifically associated with noise-exposure induced tinnitus, we compared timing rules from noise-exposed animals with tinnitus to timing rules from noise-exposed animals without tinnitus and sham animals. There were two striking differences in bimodal plasticity in tinnitus animals: 1) Timing rules were more likely to be governed by Hebbian or anti-Hebbian timing rules than suppressive or enhancing timing rules, and 2) Anti-Hebbian timing rules were broader. These results likely represent underlying changes in STDP, suggesting a potential role for STDP in generating tinnitus.

The role of bimodal STDP in the DCN is to identify spatiotemporal patterns in auditory nerve activity that are correlated with somatosensory inputs. In a normal system, narrow STDP timing rules heighten or suppress the responsivity of DCN neurons to auditory nerve inputs that are tightly correlated with somatosensory events. The broader timing rules in tinnitus animals would increase the likelihood of a somatosensory event triggering anti-Hebbian or Hebbian plasticity, leading to heightened responsivity to spontaneous, as well as driven, auditory nerve spiking patterns. The resulting hyperactivity could be a neural representation of tinnitus. This mechanism could act cooperatively with the decreases in granule cell resistance observed after noise exposure that further enhance the strength of somatosensory inputs. Furthermore, the corresponding decrease in bimodal suppression in tinnitus animals would further enhance the hyperactivity. The tinnitus-associated changes in bimodal stimulus-timing dependent plasticity suggest that somatosensory inputs have a greater influence on DCN neural activity in animals that developed tinnitus than in those that did not.

We believe that noise-exposure and tinnitus are associated with STDP metaplasticity that is likely driven by a combination of redistribution of somatosensory innervation and reduced influence of glycinergic cartwheel cells, cholinergic neuromodulation, and potentially changes in NMDAR and PKC-mediated signaling cascades.

Thus, these results confirm that metaplasticity of STDP in the DCN is new neural correlate of tinnitus. The specific combination of STDP changes in DCN after noise exposure may drive spontaneous neural activity toward spiking patterns that represent tinnitus in DCN and higher auditory structures in the auditory system. The influence of metaplasticity in higher centers could further drive spontaneous activity towards perceptual awareness. In the end, these experiments further demonstrate the particular and unexpected advantages of this technique in the treatment of tinnitus.

Figure 9:
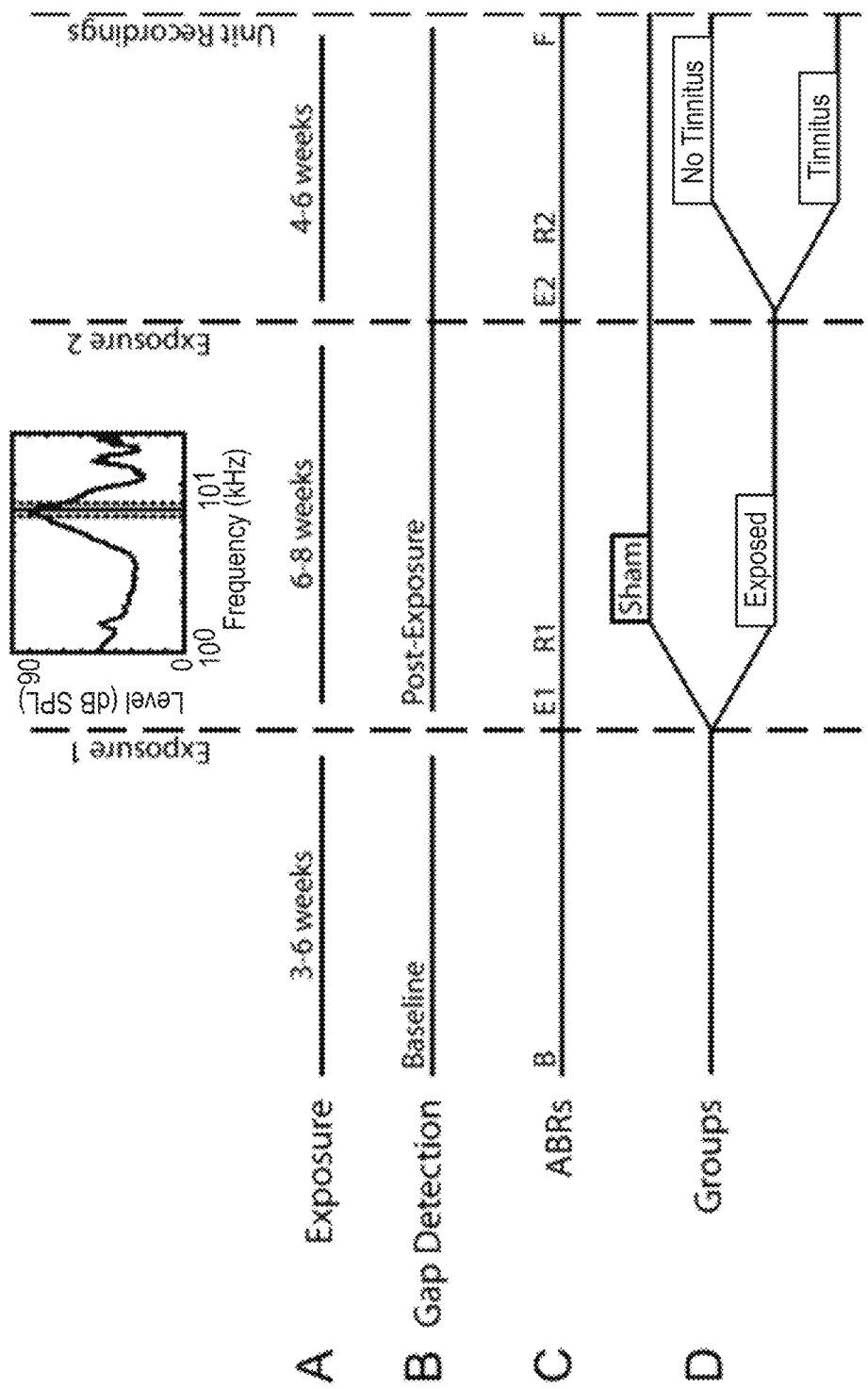
FIG. 9 illustrates multiple plots of noise exposure, gap detection testing for tinnitus, auditory brainstem response threshold measurements, and partition of guinea pigs into sham, exposure, and tinnitus regions, in accordance with an example.

The experimental procedures used for a second set of example testing procedures, corresponding to FIGS. 9-16, were as follows. Animals: Female pigmented guinea pigs (n=16) from the Elm Hill colony (300-400 g; Ann Arbor, Mich.) were used in this study. Experimental design: This study was designed to assess the effect of noise-exposure induced tinnitus on stimulus-timing dependent bimodal plasticity of sound-evoked responses and spontaneous activity. Sixteen female guinea pigs (Elm Hill, 10 noise-exposed and 6 sham-exposed) were behaviorally tested semiweekly before and after a two hour noise exposure (FIG. 9, plot "A": 97 dB noise with ¼ octave band centered at 7 kHz) using an acoustic startle-based gap detection assay for tinnitus (FIG. 9, plot "B"). Ten guinea pigs were first exposed to the narrowband noise 3-6 weeks after baseline gap detection testing. Six to 8 weeks later, each guinea pig was exposed a second time to the same narrowband noise. The remaining 6 guinea pigs were sham-exposed at the same time. Auditory brainstem response (ABR) thresholds were measured before beginning gap detection (B), immediately after the first and second noise exposures to assess threshold shift (E1 & E2), one week after each noise exposure to assess recovery of thresholds (R1 & R2), and immediately before unit recordings (F; FIG. 9, plot "C"). Four to six weeks after the 2nd noise exposure, single and multi-unit spontaneous activity, rate level functions, and bimodal stimulus-timing dependent plasticity were assessed in an acute DCN recording preparation and compared between sham and exposed groups and between tinnitus and no tinnitus groups (FIG. 9, plot "D").

Figure 10A:
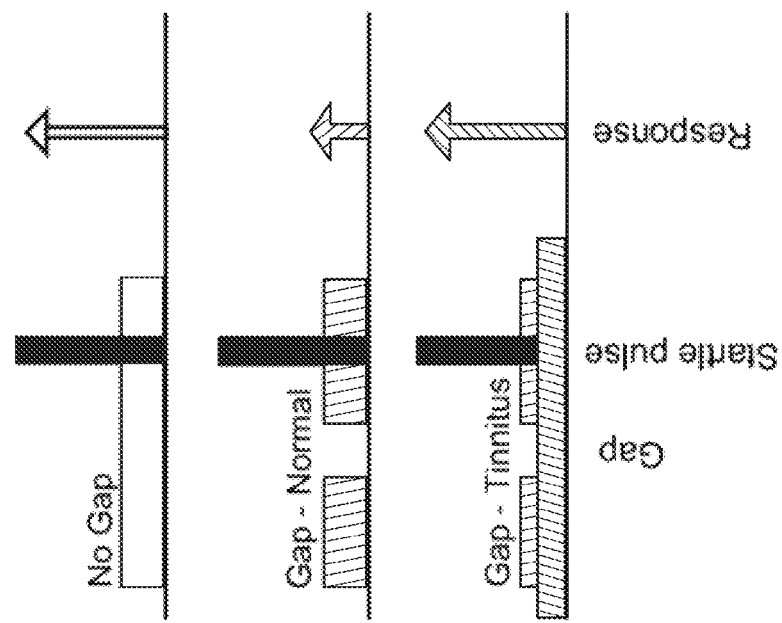
FIG. 10A illustrates a schematic of the startle based gap-detection assay text for tinnitus, illustrated no gap (top row) and gap trials (50 ms gap, 50 ms before the startle sound, bottom two rows). Each test included background sound (grey bar) with a 10 ms, 115 dB startle pulse embedded (black bar). The guinea pig startles in response to the startle stimulus, with the amplitude of the response shown by the height of each arrow. In animals without tinnitus, the gap introduces a suppression of the startle response (middle row). In animals with tinnitus, the gap is filled by the tinnitus (bottom row) and the startle response shows less reduction relative to the no gap startle response (top row arrow).
Figure 10B:
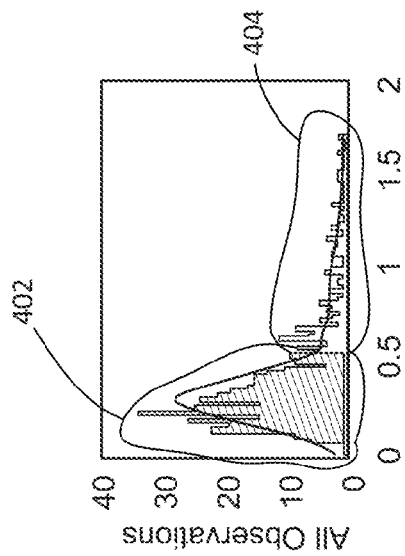
FIG. 10B illustrates a histogram of the normalized startle distribution (white line) partitioned into two distributions: no evidence for tinnitus (left bars) and evidence for tinnitus (right bars).
Figure 10C:
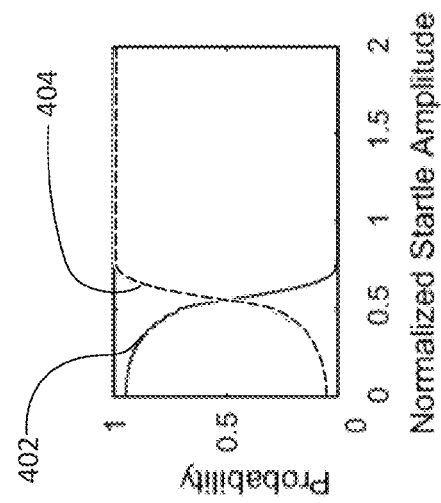
FIG. 10C illustrates a plot of the posterior probabilities that normalized startle values belong to the tinnitus or non-tinnitus distributions.
Figures 10D, 10E, 10F:
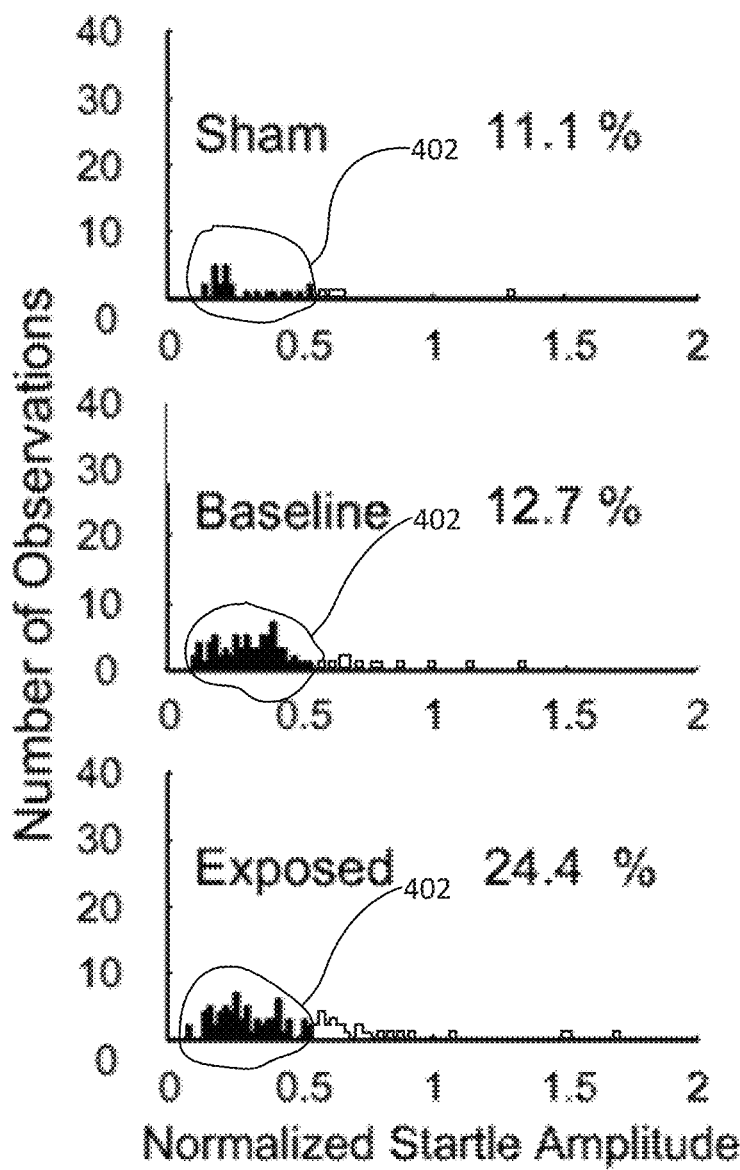
FIG. 10D illustrates a histogram of the partitioned distribution of post-exposure normalized startle observations for sham animals.
FIG. 10E illustrates a histogram of the partitioned distribution of normalized startle observations for baseline (pre-exposure) observations from sham and exposed animals.
FIG. 10F illustrates a histogram of the partitioned distribution of post-exposure normalized startle observations from exposed animals.

Gap detection testing for tinnitus: Guinea pigs were behaviorally tested with a startle-based gap detection assay for tinnitus two times per week following the previously described protocol (Dehmel et al., 2012b). In brief, guinea pigs were placed on top of a piezoelectric force measurement plate to measure movement elicited by a loud broadband noise (the startle stimulus; 115 dB, 200-20 kHz). Each trial consisted of a background noise with (Gap trials) or without (No-Gap trials) a 50 ms silent gap embedded 50 ms before the startle stimulus onset. The 60 dB background noise was either broad band noise or bandpass filtered noise with a 2 kHz band and lower cutoff frequencies of 4, 8, 12, 16, or 20 kHz. Intervals between trials randomly varied between 18 and 24 seconds. For each day of testing, an observation of the normalized startle response was computed as the ratio $[A_G/A_{NG}]$, where $A_G$ is the mean amplitude of the startle responses from 10 trials with gap on one day and $A_{NG}$ is the mean amplitude of the startle response from 10 trials with no gap on the same day (FIG. 10A). To assess the normalized startle responses within each frequency band for evidence of tinnitus for each frequency band (12 KHz is shown), the distribution of normalized startle trials from all observations from all animals was analyzed using Gaussian mixture modeling (Statistics Toolbox, Matlab release 2012b) assuming that the normalized startle observations were drawn from one of two distributions, the normal distribution (FIG. 10B, 402) and the tinnitus distribution (FIG. 10B, 404). The normalized startle observations were placed into the tinnitus group when the posterior probability was greater than 0.55 (FIG. 10C, 406). For each frequency band, using the threshold established by the Gaussian mixture model, the distributions of normalized startle responses from sham animals after noise exposure (Sham, FIG. 10D), all animals before noise exposure (Baseline, FIG. 10E), and exposed animals after noise exposure (Exposed, FIG. 10F) were partitioned into tinnitus and no tinnitus observations. Animals from the exposed group that demonstrated more tinnitus observations than were found during baseline testing were considered to have tinnitus within the tested frequency band. For FIGS. 10D-10F only the distribution 402 is labeled, corresponding to non-tinnitus; the other distribution values correspond to distribution 404, corresponding to tinnitus. For statistical evaluation, animals with no exposure were assigned to the sham group, noise-exposed animals with no evidence for tinnitus were assigned to the Exposed-No-Tinnitus (ENT) group, and noise-exposed animals with evidence for tinnitus were assigned to the Exposed-Tinnitus (ET) group. Pre-pulse inhibition was assessed in the same manner as gap-detection. All groups of animals showed no differences in pre-pulse inhibition before and after the noise damage. This result was taken to mean that baseline temporal processing was unchanged by the noise damage and therefore any changes in gap-detection were as a result of the tinnitus "filling the gap" and not because of a temporal processing dysfunction or hearing loss.

Surgical approach for neural recordings: Guinea pigs were anesthetized (subcutaneous injection of ketamine and xylazine, 40 mg/kg, 10 mg/kg; at the incision site a subcutaneous injection of lidocaine, 4 mg/kg) and ophthalmic ointment applied to their eyes. Their heads were fixed in a stereotaxic frame using a bite bar and hollow ear bars were placed into the ear canals. Core temperature was maintained at 38° C. A left craniotomy was performed and a small amount of cerebellum was aspirated (leaving paraflocculus intact) to allow for visual placement of the recording electrode. Supplemental doses of ketamine and xylazine (I.M.) were administered at least hourly when indicated by response to a toe pinch. The guinea pig's physiological condition was monitored by assessment of body temperature, respiration and heart rates, and unit thresholds. After the completion of neural recording, the guinea pig was sacrificed by I.P. injection of sodium pentobarbitol followed by decapitation.

Electrode placement: A concentric bipolar stimulating electrode (FHC, Bowdoin, Me.) was placed stereotaxically into Sp5 after being dipped in fluorogold; −10 degrees below horizontal, 0.28+/−0.03 cm lateral from midline; 0.25+/−0.02 cm caudal from transverse sinus; 0.9+/−0.1 cm below surface of cerebellum. Post-mortem reconstruction confirmed electrode locations. A four-shank, thirty two-channel silicon-substrate electrode (site spacing=100 um, shank pitch=250 um, site area=177 um2, impedance=1-3 mOhms, NeuroNexus, Ann Arbor, Mich.) was placed with the tips 0.80-1.0 um below the surface of the DCN with shanks rostral-to-caudal approximately within an iso-frequency layer. If the top site on each shank did not respond to sound, the electrode was lowered until they responded to noise.

Auditory and somatosensory stimulation: Cosine window-gated Tone signals (50 ms duration, 2 ms rise/fall time) were generated using Open Ex and an RX8 DSP (TDT, Alachula, Fla.) with 12 bit precision and sampling frequency set at 100 kHz. A shielded speaker (DT770, Beyer) driven by an HB7 amplifier (TDT, Alachula, Fla.) delivered sound through a hollow earbar to the left ear. The system response was measured using a condenser microphone attached to the hollow earbar by a ¼" long tube approximating the ear canal. Sound levels were adjusted to account for the system response using a programmable attenuator (PAS, TDT, Alachula, Fla.) to deliver calibrated levels (dB SPL) at frequencies from 200 Hz to 24 kHz. Neurons in somatosensory brainstem nuclei known to project to DCN were activated by three biphasic (100 us/phase) current pulses at 1000 Hz delivered to Sp5 through a concentric bipolar electrode. The current amplitude was set to the highest level (range: 50-70 μA) that did not elicit movement artifact.

Assessment of stimulus-timing dependent bimodal plasticity: Stimulus-timing dependent plasticity was assessed in all guinea pigs using an established in vivo bimodal plasticity induction protocol. In short, spontaneous activity and responses to unimodal tone stimuli were recorded at three time points: before, and 3 and 15 minutes after the bimodal stimulation protocol. The bimodal stimulation protocol in this example consisted of 300 trials of the 50 ms tones combined with Sp5 activation. The bimodal interval was defined as the Sp5 stimulus onset time minus the tone stimulus onset time. Thus, positive bimodal intervals indicate Sp5-leading tone stimulation and negative bimodal intervals indicate tone-leading Sp5 stimulation. Stimulus-timing dependence was assessed by varying the bimodal interval and measuring the change in unimodal tone-evoked firing rates before and after bimodal stimulation. The recording block was repeated with the bimodal interval between tone and somatosensory stimuli randomly selected from the following list: −40, −20, −10, 0, 10, 20, or 40 ms. Control recording blocks were also included in which unimodal tone or Sp5 stimuli replaced the bimodal stimuli. To assess recovery after bimodal stimulation, responses to unimodal tones were measured every 15-30 minutes for as long as possible to assess recovery after bimodal stimulation.

To assess recovery after bimodal stimulation, responses to unimodal tones were measured every 15-30 minutes after the final bimodal stimulation block for up to 2 hours. Timing rules for principal cell units (excluding units with type II receptive fields) were classified as Hebbian, anti-Hebbian, suppressing, or enhancing by comparing the mean change in firing rate (i.e., the firing rate before bimodal stimulation subtracted from the firing rate after bimodal pairing) when the Sp5 stimulus preceded the sound and when the Sp5 stimulus followed the sound. Timing rule classification corresponded to that used previously. For comparison between sham, ET, and ENT animals, spontaneous firing rates were measured from the first recording block before any bimodal stimulation.

Spike detection and sorting: Voltages from each site were digitized by a PZ2 preamp (Fs=12 kHz, TDT, Alachua, Fla., USA) and band-pass filtered (300 Hz-3 kHz). Online spike detection used a voltage threshold set 2.5 standard deviations above background noise (RZ2, TDT, Alachua, Fla., USA). Timestamps and waveform snippets were saved to a PC and sorted using principal components of the waveform shape and K-means cluster analysis with fixed variance (95%) and 5 clusters (Plexon Offline Sorter). Cluster distinctness was confirmed with pairwise cluster statistics (p>0.05; Plexon Offline Sorter) and visually by a trained observer. When a spike was present in a 1 ms window across 80% of channels, any spikes within that window were considered artifact and removed from further analysis. The waveform shapes, amplitudes, and response properties of multi-unit clusters in this study were consistent over the duration of the recording.

As discussed herein, the techniques may apply the auditory component of bimodal stimulation at frequencies identified as tinnitus frequencies or at other frequencies determined to reduce tinnitus. In further examples, the techniques may present timing intervals at, for example, +10 ms or +20 ms (i.e., somatosensory stimulation before auditory stimulation) at the tinnitus frequency, while timing intervals at, for example, −10 ms and −20 ms (i.e., auditory stimulation before somatosensory stimulation) for 'off-tinnitus' frequencies. This will have the effect of reducing hyperactivity seen at the tinnitus frequency regions of the cochlear nucleus and increasing activity in regions not associated with tinnitus, thus 'equalizing' the firing rates across all frequencies. Further still, in some examples, the treatment techniques herein may present a statistical distribution of bimodal intervals. For example, the tinnitus frequency could be paired with somatosensory stimulation at intervals pulled from a Gaussian distribution centered at −15 ms with a standard deviation of 2 ms. Non-tinnitus frequencies could be either paired at intervals pulled from a broad Gaussian or uniform distribution centered at 0 ms or could be paired at intervals pulled from a Gaussian distribution centered at +15 ms with a standard deviation of 2 ms. Having varied bimodal intervals, for example, over a statistical distribution, a few features may result. It may allow for fine tuning any initial bimodal interval, which may be useful for initial intervals that are estimates. Moreover, neurons may have varied preferred timings for suppression. Therefore, by varying the bimodal interval, on different trials, the techniques may more readily achieve the maximal suppression for some neurons and partial suppression for others. Further still, by applying a distribution of bimodal treatments, one can address the possibility that preferred intervals will drift over time with the state of the auditory system.

Figure 17A:
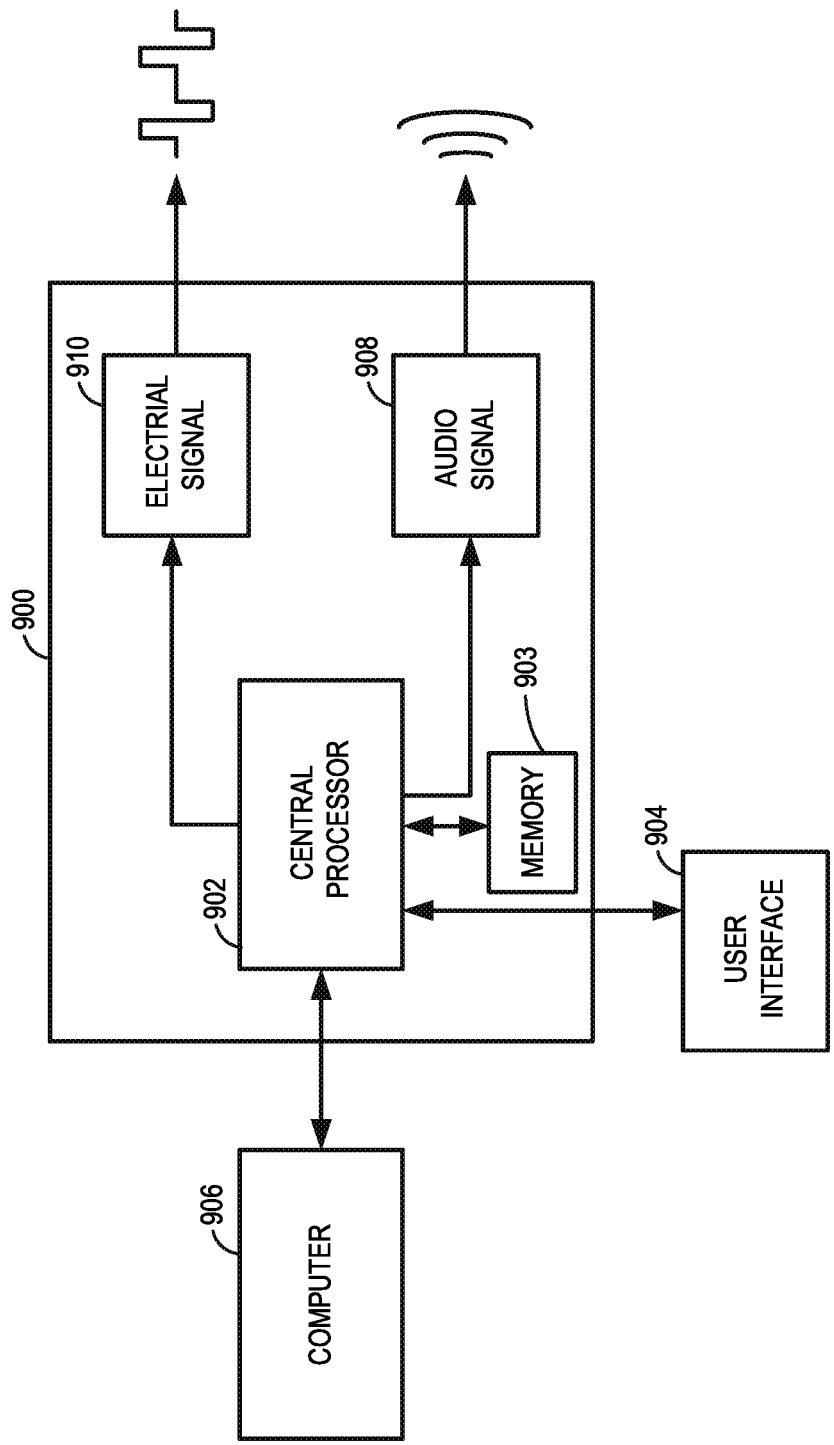
FIG. 17A illustrates an example hardware system for implementing the tinnitus reduction techniques described herein, in accordance with an example.
Figure 17B:
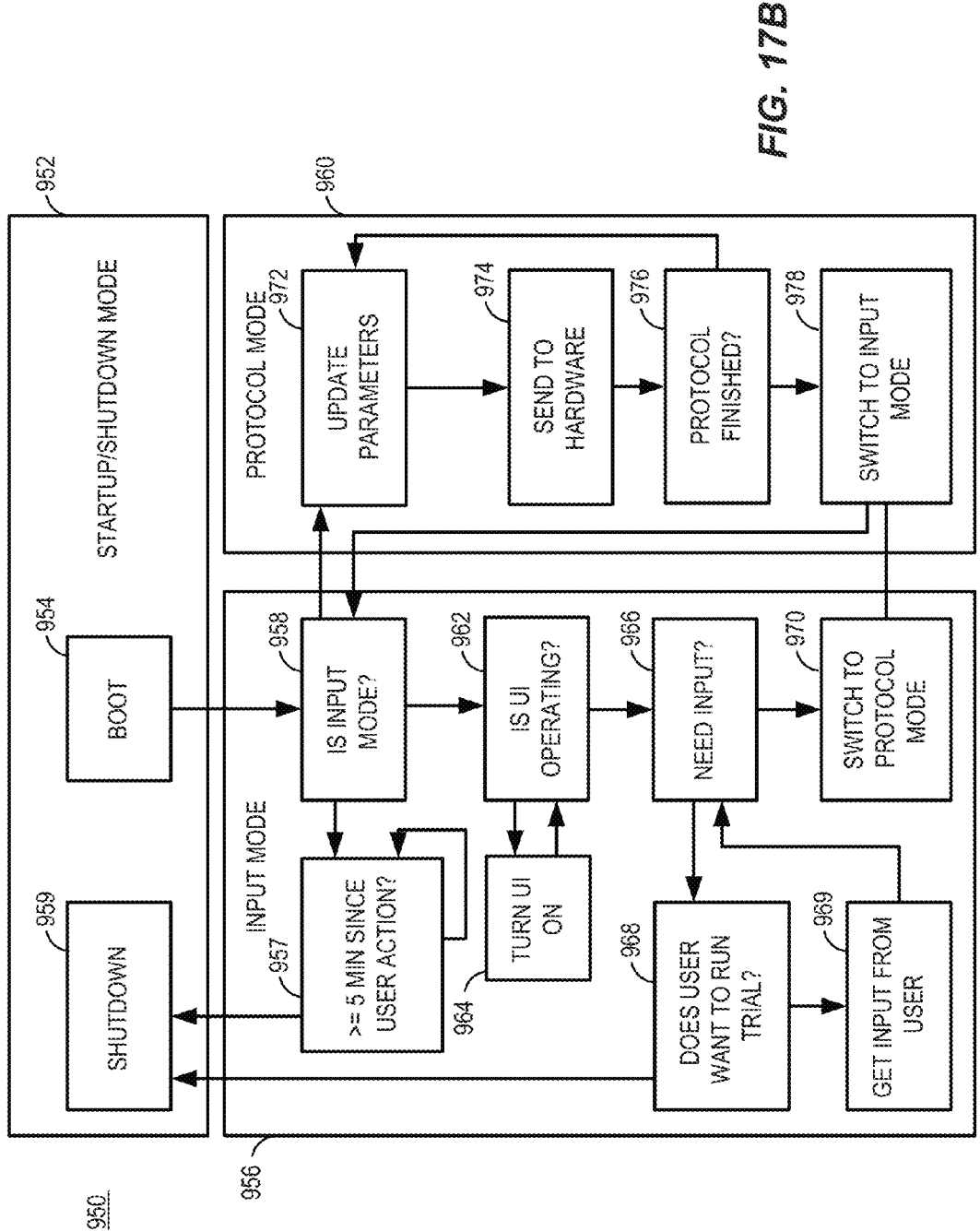
FIG. 17B illustrates a software platform that may be executed by instructions on a computer to implement techniques described herein, in accordance with an example.

FIGS. 17A and 17B illustrate an example hardware system and software diagram as may be used for implementing the tinnitus reduction techniques described herein. FIG. 17A illustrates a bimodal stimulation machine 900 having a processing unit 902 and memory 903 that executes instructions providing a user interface 904 to a user, for example through a display screen and that interfaces with a computer 906 that may provide instructions to the machine 900 for performing bimodal stimulation of a patient. As discussed in examples herein, the computer 906 may perform signal and data analysis to determine timing controls, e.g., determining the order, spacing, frequency, amplitudes, etc. for two stimulation signals, an auditory stimulation signal and a somatosensory stimulation signal, transmitted via an audio signal generator 908 (e.g., an audio transducer) and a somatosensory signal generator (e.g., an electrical signal generator 9101 in the illustrated example of FIG. 17A. While various features are described as performed by one or both of the machine 900 and the computer 906, it will be understand that any of the features described herein may be performed one or both of these, and that either individually or collected may be referred to herein as an example bimodal stimulation system, of which other examples are also provided herein, including in FIG. 18.

FIG. 17B illustrates a software platform 950 that may be executed by instruction on the machine 900, the computer 906, or some combination thereof, in various example implementations of the present techniques. A startup mode 952 initiates operation through a boot process 954, from which the machine 900 enters into an input mode 956. From the input mode 956, the machine 900 determines, at a decision block 958, whether the machine is to be in the input mode 956 or a protocol mode (also termed a treatment mode) 960, e.g., as may be selected by a user. An optional block 957 is shown a represents a user input waiting call instruction with a five minute limit before initiating system shutdown 959. In input mode 956, the platform 950 determines, at block 962, whether the user interface is on or not, where if it is not already one, then it is turned on at block 964. Either way, control is provide to an input awaiting block 966, which awaits input from the user via block 968 and more specifically may request from the use whether the user wants to run a trial bimodal stimulation procedure. If so, a user inputs a request at block 969 before passing control back to the block 966 and on to a protocol switching mode initiator 970. Otherwise the block 968 passes control to shutdown procedure 959.

Once, at block 958, a protocol mode exists, control is passed to the protocol model 960, and more specifically to an update parameters block 972 that determines the parameters for bimodal stimulation, including the order, spacing, frequency, amplitudes, of the auditory system and somatosensory system stimulation signals. In some examples, these parameters may be retrieved from a historical data of past treatment parameters. In some examples, these parameters may be prognostically determined from current and/or historical patient data, such as physiological data measured for a patient. In some examples, these parameters may be determined from patient input. For example, with the machine 900 implemented as point of care computer, such as a laptop, tablet computer, mobile smart phone, netbook, notebook computer, personal data assistant, handheld device, or desktop device, a user may be presented with a user interface that allows them to select the parameters for both the auditory system and somatosensory system stimulation signals, until the tinnitus or hyperacusis, etc. has been sufficiently treated. As such as smart device, the machine 900 may record the parameters as the user is identifying the optimum parameter settings for treatment, including recording the time and day of the treatment. In some examples, the smart device also automatically determines an optimum adjustment scale, selectively determining over which parameter ranges to apply a course tunability adjustment scale of the parameter value versus over which parameter ranges to apply a fine tunability adjustment scale. In this way, the smart device may allow a patient to do course adjustments on parameters, until those parameter values approach a predicted range, from which the smart device may switch to a fine adjustment scale to allow a patient better control in determining the exact parameters.

In any event, in the illustrated example, the block 972 updates the parameters for bimodal stimulation from stored data; and these parameters are sent to hardware such as to the signal generators (e.g., transducers) 908 and 910 through a block 974 and the bimodal stimulation treatment is provided to the patient. The treatment may be for a determined or predetermined period of time. Therefore, in some examples, a control loop is used to successively apply the bimodal stimulation treatment for the desired time period until it is determined at the block 976 that the treatment protocol is finished. The treatment duration may be automatically determined by the system, may be set by the patient or health care provider, may be determined from historical data on the patient, or may be determined from historical data across an identified patient population. These are provided by way of example. When the protocol mode set is finished (as determined at block 976) the mode is switched to an input mode, via a block 978. A user may modulate various parameters to affect the timing between an auditory system stimulus and a somatosensory system stimulus, such as repetition count, and stimulus parameters such as intensity, frequency, time separation, time delay, and duration, where such control may be achieved over a millisecond or smaller time control, in some examples.

Figure 18:
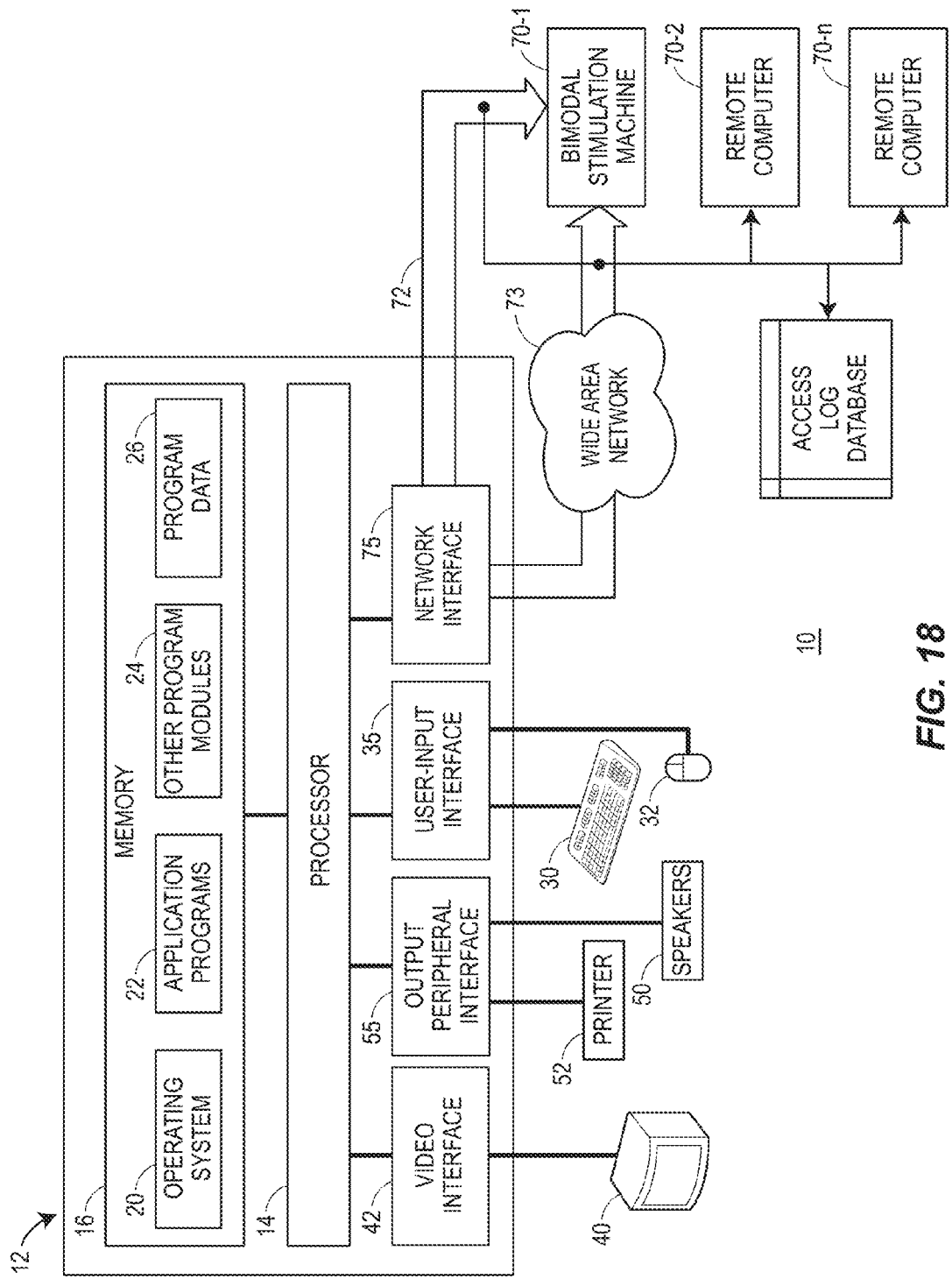
FIG. 18 illustrates an exemplary bimodal stimulation system for performing the techniques described herein, in accordance with an example.

FIG. 18 illustrates an exemplary bimodal stimulation system for implementing the blocks of the method and apparatus includes a general-purpose computing device in the form of a computer 12. Components of computer 12 may include, but are not limited to, a processing unit 14 and a system memory 16. The computer 12 may operate in a networked environment using logical connections to one or more remote computers, such as remote computers 70-1, 70-2, . . . 70-n, via a local area network (LAN) 72 and/or a wide area network (WAN) 73 via a modem or other network interface 75. These remote computers 70 may include other computers like computer 12, but in some examples, these remote computers 70 include one or more of (i) an auditory stimulation machine, (ii) a somatosensory stimulation machine, (iii) a signal records database systems, (iv) a scanner, and/or (v) a signal filtering system.

In the illustrated example, the computer 12 is connected to a bimodal stimulation machine, labeled machine 70-1. The bimodal stimulation machine 70-1 may be a stand-alone system, having multiple stimulation leads for transmitting bimodal stimulation signals in accordance with the techniques described herein. In other examples, a series of stimulation probes may be connected directly to the computer 12.

Computer 12 typically includes a variety of computer readable media that may be any available media that may be accessed by computer 12 and includes both volatile and nonvolatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. For example, the tinnitus detection, bimodal stimulation analysis, and bimodal stimulation treatment techniques described herein may be implemented as instructions stored in the application programs block 22 and executable by computer 12. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Generally, the techniques herein may be coded any computing language for execution on computer 12. Stimulation instruction data may be determined at the remote computers 70-1, 70-2, . . . 70-n or at any of the computer storage devices of computer 12. The instructions may be stored on any of these computers and devices as well. Furthermore, the remote computers 70-1, 70-2, . . . 70-n may receive instructions from a patient indicating perceived effectiveness the bimodal stimulation, for the computer 12 or the remote computers to adjust the stimulation control signals in response thereto.

A user may input or select the condition parameters through an input mechanism to set the applied bimodal stimulation. Although, in other examples, the parameters for bimodal stimulation may be pre-selected or automatically determined, for example, based on a particular type of analysis that is to be performed. The output of the executable program may be displayed on a display (e.g., a monitor 40), sent to a printer 52, stored for later use by the computer 12, or offloaded to another system, such as one of the remote computers 70. The output may be in the form of an image (such as the figures herein), a graph, a table or any combination thereof, by way of example. Operations of the system may be recorded in a log database for future reference as shown. This log database may be accessed at subsequent times.

With the systems described, by way of example herein (e.g., FIGS. 17A, 17B, and 18), techniques to treat tinnitus may be achieved. Further, it will be appreciated that examples described herein as achieved by any of the machines and/or software of these figures, may be achieved by any other of these machines and/or software, as well as by other systems. These techniques include generating an audible stimulation signal (e.g., a pure tone, a narrowband noise, a broadband noise, a harmonic complex, etc., or some combination thereof) having a first firing point and first firing period, stimulus onset, and/or duration. They may also include generating a somatosensory stimulation signal to stimulate a somatosensory system of a subject, the somatosensory stimulation signal having a second firing point and second firing period, stimulus onset, and/or duration. A timing order and timing difference between the first firing point and the second firing point may then be established to reduce the tinnitus. The first firing period and the second firing period may be maintained asynchronously to reduce tinnitus so that the onset of the first firing period does not overlap the onset of the second firing period. In some examples, the entire first and second firing periods do not overlap. In some examples, the first firing point will be before the second firing point, while in other examples, the firing point order will be reversed. The timing order may be changed to determine a desired reduction or illumination in tinnitus, for example, based on responses of subject.

The bimodal stimulation machine 70-1, for example, may be controlled to establish first and second firing conditions (e.g., firing points, firing periods, duration, stimulation signal pattern for both electrical and auditory signals, stimulation signal intensities) to reduce or remove tinnitus. In some examples, the machine 70-1 may include probes positioned to apply, to a subject, a somatosensory stimulation signal by applying stimulation to the brain to stimulate the somatosensory system. In some examples, the machine 70-1 may include probes that applying the somatosensory stimulation signal to the subject by applying stimulation to the trigeminal nerve via facial stimulation or the cervical spinal nerve of the subject to stimulate the somatosensory system. In some examples, the probes are deep brain region probes that stimulate the somatosensory system. Thus in some examples, the somatosensory stimulation signal to a subject results from applying stimulation to a surface region of the brain of the subject or to a surface structure on the face or a surface structure on the neck of the subject to stimulate the somatosensory system. These stimulations, whether auditory stimulation and somatosensory stimulation, may be provided through a mechanical or electrical stimulation.

In addition to applying the bimodal stimulation, the systems described may be used to determine a timing profile for a subject. The timing profile may contain timing data of different timing orders and timing differences between the first firing point and the second firing point and containing perceived tinnitus data for the different timing orders and timing differences. That data may be stored in the memory 16, for example, as timing profile data, which may be later used by the machine 12 to determine a suggested tinnitus treatment regimen for bimodal stimulation using the auditory stimulation signal and the somatosensory stimulation signal.

For example, different timing orders may be provided to a subject through the stimulation machine 70-1, while the subject responds, using the machine 70-1 (or other input device or verbally to a practitioner using the machine 12) with a perceived reduction in tinnitus. That perception data is recorded by the machine 12 along with the bimodal stimulation conditions to develop a timing profile for how to reduce tinnitus experienced by that particular subject. That profile may be developed over numerous tests, i.e., based on historically collected data for the patient.

Using this timing profile, the machine 12 can, in some examples, determine an initial timing profile for a subject, the timing profile containing an initial timing order and timing difference for the first firing point and the second firing point. The timing profile has been determined to reduce tinnitus after onset.

In this way the systems described herein can automatically establish a timing order and timing difference between first and second firing points to reduce tinnitus.

In some examples, the timing profile may be developed to include global time data, so that the timing profile includes project times of day, days in the week, etc. when tinnitus seems to occur more frequency for the patient. The machine 12 may use the timing profile to attempt to pre-empt onsets of tinnitus based on this timing profile example.

Thus, the machine 12 may adjust the timing order and timing difference between firing points to determine a tinnitus reduction profile for a period of time, where this profile may be accessed later for applying bimodal stimulation. For example, when a treatment time is identified (e.g., a future point in time or from an trigger such as subject activating the bimodal stimulation treatment upon perceiving tinnitus), this profile may be accessed to identify a timing order and timing difference for the treatment time, which may then be applied using the stimulation machine 70-1. In some examples, the machine 12 may periodically adjust the first and/or second firing periods to affect tinnitus reduction. In any event, as will be appreciated by the foregoing adjusting the timing order and the timing difference between the first firing point and the second firing point to selectively increase or decrease firing rates in an identified neurons.

While example implementations are described for treating tinnitus, the present techniques are not limited to the treatment of tinnitus. The techniques may be used to treat any number of auditory conditions, of which hyperacusis is an example. Moreover the application programs 22 may include other instructions for treating an auditory condition. These include: instructions for increasing firing rates for the neurons in the dorsal cochlear nucleus, ventral cochlear nucleus, and/or auditory cortex; instructions for decreasing firing rates for the neurons in the dorsal cochlear nucleus, ventral cochlear nucleus, inferior colliculus, auditory cortex and/or other nuclei associated with tinnitus.

In some examples, the computer 12 determines optimal parameter values for an audible stimulation signal and a somatosensory stimulation signal to alter firing rates for neurons in the dorsal cochlear nucleus, ventral cochlear nucleus, and/or auditory cortex.

In some examples, the computer 12 identifies initial parameters for timing and intervals of a bimodal stimulation for a subject by identifying stimulation parameters that in the subject produce a reduction in objective measures of neural correlates of tinnitus assessed by any of an electroencephalography test, auditory brainstem response (ABR) test, or psychophysical tinnitus matching test.

It will be appreciated that the techniques may be used to treat any number of auditory diseases, using targeted neural suppression or enhancement via specifically-timed auditory-somatosensory stimulation. These include cochlear implants and central auditory processing disorder. For cochlear implants, tonotopic remapping after implantation occurs gradually and likely plays a role in implant training. During training, cochlear implant stimulation followed by somatosensory stimulation would lead to enhanced responses, potentially accelerating tonotopic remapping. For auditory processing disorders, complex sounds that are poorly distinguished could be presented followed by somatosensory stimulation, leading to enhanced responses to those complex sounds, and better neural representation.

It will be appreciated that the above descriptions are provided by way of example and that numerous modifications may be made within context of the present techniques.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A computer-implementable method, for treating an auditory condition in a subject, the method comprising:
    determining, in a processor, optimal parameter values for an audible stimulation signal and a somatosensory stimulation signal to alter firing rates for neurons in the auditory and non-auditory pathways involved in the auditory condition, wherein the optimal parameter values comprise timing and/or ordering information for the audible stimulation signal and the somatosensory stimulation signal; and
    applying the audible stimulation signal to the auditory system of the subject, using an audible signal generator, and applying the somatosensory stimulation signal, using a somatosensory signal generator, in accordance with the timing and/or ordering information in the optimal parameters thereby treating the auditory condition of the subject,
    wherein the somatosensory signal generator is physically connected to the subject to apply the somatosensory stimulation signal electrically or mechanically to the somatosensory system of the subject, and wherein the audible signal generator is a sound generator positioned to apply the audible stimulation signal to the auditory system.

2. The method of claim 1, the method further comprising:
    increasing firing rates for the neurons in the auditory and non-auditory pathways involved in the auditory condition.

3. The method of claim 1, the method further comprising:
    decreasing firing rates for the neurons in the auditory and non-auditory pathways involved in the auditory condition.

4. The method of claim 1, the method further comprising:
    applying the somatosensory stimulation signal to the somatosensory system of the subject using deep brain probes connected to the subject for electrically stimulating the somatosensory system.

5. The method of claim 1, the method further comprising:
    applying the somatosensory stimulation signal to the somatosensory system of the subject using electrodes connected to a surface structure on the face or neck of the subject for stimulating the somatosensory system.

6. The method of claim 1, the method further comprising:
    applying the audible stimulation signal to the auditory system using a speaker adjacent to and providing the sound to an ear of the subject.

7. The method of claim 6, wherein the sound comprises one or more tones.

8. The method of claim 6, wherein the sound comprises a tone, a narrowband noise, a broadband noise, a harmonic complex, or a combination thereof.

9. A system for treating an auditory condition in a subject, the system comprising:
    a processor and a memory; and
    a bimodal stimulation system having a processor and a memory and configured to,
    determine, in the processor, optimal parameter values for an audible stimulation signal and a somatosensory stimulation signal to alter firing rates for neurons in the auditory and non-auditory pathways involved in the auditory condition, wherein the optimal parameter values comprise timing and/or ordering information for the audible stimulation signal and the somatosensory stimulation signal, and
    apply, using an audible signal generator, the audible stimulation signal to the auditory system of the subject and apply, using a somatosensory signal generator, the somatosensory stimulation signal to the somatosensory system of the subject in accordance with the timing and/or ordering information in the optimal parameters thereby treating the auditory condition of the subject,
    wherein the somatosensory signal generator is configured to physically connect to the subject to apply the somatosensory stimulation signal electrically or mechanically to the somatosensory system of the subject, and wherein the audible signal generator is a sound generator configured to apply the audible stimulation signal to the auditory system of the subject.

10. The system of claim 9, wherein the bimodal stimulation system is configured to
    increase firing rates for the neurons in the auditory and non-auditory pathways involved in the auditory condition.

11. The system of claim 9, wherein the bimodal stimulation system is configured to
    decrease firing rates for the neurons in the auditory and non-auditory pathways involved in the auditory condition.

12. The system of claim 9, wherein the bimodal stimulation system is configured to apply the somatosensory stimulation signal to the somatosensory system of the subject through deep brain probes connected to the subject for electrically stimulating the somatosensory system.

13. The system of claim 9, wherein the bimodal stimulation system is configured to apply the somatosensory stimulation signal to the somatosensory system of the subject using electrodes connected to a surface structure on the face or neck of the subject for stimulating the somatosensory system.

14. The system of claim 9, wherein the bimodal stimulation system is configured to apply the audible stimulation signal to the auditory system using a speaker configured to be placed adjacent to and provide the sound to an ear of the subject.

15. The system of claim 14, wherein the sound comprises one or more tones.

16. The system of claim 14, wherein the sound comprises a tone, a narrowband noise, a broadband noise, a harmonic complex, or a combination thereof.

* * * * *

UNITED STATES PATENT AND TRADEMARK OFFICE
CERTIFICATE OF CORRECTION

PATENT NO. : 9,682,232 B2
APPLICATION NO. : 14/977416
DATED : June 20, 2017
INVENTOR(S) : Susan Shore et al.

Page 1 of 1

It is certified that error appears in the above-identified patent and that said Letters Patent is hereby corrected as shown below:

In Figure 17A, Tag "910", Line 1, please delete "ELECTRIAL" and insert -- ELECTRICAL --.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*